(12) United States Patent
Kwon et al.

(10) Patent No.: US 9,416,352 B2
(45) Date of Patent: Aug. 16, 2016

(54) **MUTANT *NEQ* HS DNA POLYMERASE DERIVED FROM *NANOARCHAEUM EQUITANS* AND ITS APPLICATION TO HOT-START PCR**

(71) Applicant: Research & Business Foundation SUNGKYUNKWAN UNIVERSITY, Suwon-si (KR)

(72) Inventors: Suk Tae Kwon, Suwon-si (KR); Sung Suk Cho, Suwon-si (KR); Mi Yu, Suwon-si (KR); Kyung Min Kwon, Suwon-si (KR); Seung Hyun Kim, Suwon-si (KR)

(73) Assignee: Research & Business Foundation SUNGKYUNKWAN UNIVERSITY, Suwon-si (KR)

( * ) Notice: Subject to any disclaimer, the term of this patent is extended or adjusted under 35 U.S.C. 154(b) by 0 days.

(21) Appl. No.: 14/555,863

(22) Filed: Nov. 28, 2014

(65) Prior Publication Data
US 2015/0159146 A1   Jun. 11, 2015

(30) Foreign Application Priority Data
Nov. 29, 2013   (KR) .................. 10-2013-0147812

(51) Int. Cl.
| | | |
|---|---|---|
| *C12P 19/34* | (2006.01) | |
| *C12N 9/12* | (2006.01) | |
| *C12N 15/00* | (2006.01) | |
| *C12N 1/21* | (2006.01) | |
| *C12Q 1/68* | (2006.01) | |

(52) U.S. Cl.
CPC ............ *C12N 9/1252* (2013.01); *C12Q 1/686* (2013.01); *C07K 2319/00* (2013.01); *C07K 2319/21* (2013.01)

(58) Field of Classification Search
None
See application file for complete search history.

(56) References Cited

U.S. PATENT DOCUMENTS

| | | | |
|---|---|---|---|
| 5,677,152 A | 10/1997 | Birch et al. | |
| 6,183,998 B1 | 2/2001 | Ivanov et al. | |
| 7,749,732 B2 | 7/2010 | Kwon et al. | |
| 2011/0086387 A1* | 4/2011 | Kwon .................. | C12N 9/1252 435/69.1 |
| 2012/0135472 A1 | 5/2012 | Kwon et al. | |
| 2013/0131315 A1* | 5/2013 | Su .......................... | C12P 21/00 530/350 |

FOREIGN PATENT DOCUMENTS

| | | |
|---|---|---|
| KR | 10-0793007 B1 | 1/2008 |
| KR | 10-2009-0043282 A | 5/2009 |
| KR | 10-1105271 B1 | 1/2012 |
| KR | 10-1230362 B1 | 2/2013 |
| WO | WO 00/44926 A1 | 8/2000 |

OTHER PUBLICATIONS

Bateman, D., obtained from www.researchgate.net on May 26, 2016; 4 pages.*
Barnes, Wayne M., and Katherine R. Rowlyk. "Magnesium precipitate hot start method for PCR." Molecular and cellular probes 16.3 (2002): pp. 167-171.
Choi, Jeong Jin, et al. "Unique Substrate Spectrum and PCR Application of Nanoarchaeum equitans Family B DNA Polymerase." Applied and environmental microbiology 74.21 (Sep. 12, 2008): pp. 6563-6569.
Lebedev, Alexandre V., et al. "Hot Start PCR with heat-activatable primers: a novel approach for improved PCR performance." Nucleic acids research vol. 36, No. 20 (Sep. 16, 2008): pp. e131-e131.
Mary C. Longo., et al. "Use of uracil DNA glycosylase to control carry-over contamination in polymerase chain reactions" Life Technologies, Inc., 1990 Elsevier Science Publishers B.V. Gene, 93 (1990) pp. 125-128.
Kelly S. Lundberg., et al. "High-fidelity amplification using a thermostable DNA polymerase isolated from Pyrococcus furiosus" 1991 Elsevier Science Publishers B.V. Gene, 108 (1991) 1-6.
Miozzari, Giuseppe, and Charles Yanofsky. "Naturally occurring promoter down mutation: Nucleotide sequence of the trp promoter/operator/leader region of Shigella dysenteriae 16." Proceedings of the National Academy of Sciences 75.11 (Nov. 1978): pp. 5580-5584.
Reikofski, Julia, and Bernard Y. Tao. "Polymerase chain reaction (PCR) techniques for site-directed mutagenesis." Biotechnology advances vol. 10, No. 4 (1992): pp. 535-547.
Rys, P. N., and D. H. Persing. "Preventing false positives: quantitative evaluation of three protocols for inactivation of polymerase chain reaction amplification products." Journal of clinical microbiology 31.9 (1993): pp. 2356-2360.
Song, Jung Min, et al. "Characterization and PCR performance of a family B-type DNA polymerase from the hyperthermophilic crenarchaeon Staphylothermus marinus." Enzyme and Microbial Technology 40.6 (2007): pp. 1475-1483.

(Continued)

*Primary Examiner* — David J Steadman
(74) *Attorney, Agent, or Firm* — NSIP Law

(57) ABSTRACT

A DNA polymerase (Neq DNA polymerase) derived from *Nanoarchaeum equitans* is split into Neq L and Neq S fragments, each of which contains inteins. A Neq hot-start (HS) DNA polymerase in which the inteins of the Neq L and Neq S fragments are linked with each other is provided in the form of a precursor of Neq DNA polymerase. A purification method can be significantly improved by inserting a His-tag sequence composed of six histidine residues between the inteins of the Neq L and Neq S fragments at a gene level. As a result of effort to enhance PCR efficiency of the Neq HS DNA polymerase, a gene coding for the Neq HS DNA polymerase is mutated at specific positions to screen mutant Neq HS polymerases (M1, M2, and M3) having a highly improved PCR amplification rate and amplification level.

12 Claims, 15 Drawing Sheets

(56) References Cited

OTHER PUBLICATIONS

Choi, Jeong Jin, et al. "Protein Trans-splicing and Characterization of a Split Family B-type DNA Polymerase from the Hyperthermophilic Archaeal Parasite Nanoarchaeum equitans." 2006 Elsevier Ltd. Journal of molecular biology 356.5 (2006):pp. 1093-1106.

Fogg, Mark J., Laurence H. Pearl, and Bernard A. Connolly. "Structural basis for uracil recognition by archaeal family B DNA polymerases." Nature Structural & Molecular Biology 9.12 (2002): pp. 922-927.

Gill, Sukhvinder, et al. "Interaction of the Family-B DNA Polymerase from the Archaeon Pyrococcus furiosuswith Deaminated Bases." Journal of molecular biology 372.4 (2007): 855-863.

* cited by examiner

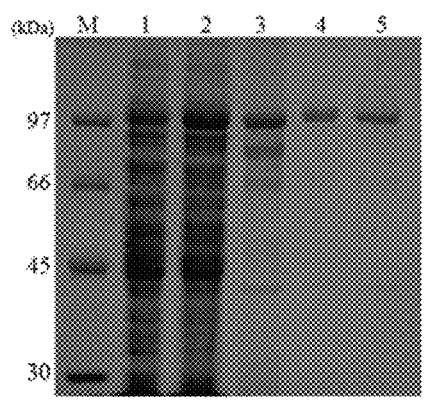 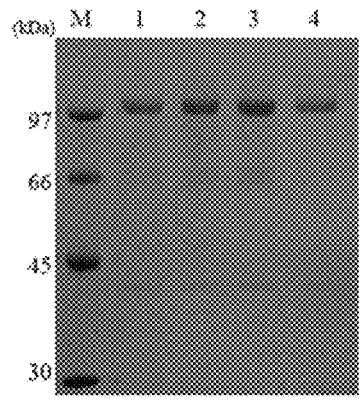
FIG. 4A
FIG. 4B

MUTANT *NEQ* HS DNA POLYMERASE DERIVED FROM *NANOARCHAEUM EQUITANS* AND ITS APPLICATION TO HOT-START PCR

CROSS-REFERENCE TO RELATED APPLICATION

This application claims priority to and the benefit under 35 U.S.C. 119 of Korean Patent Application No. 10-2013-0147812, filed on Nov. 29, 2013 in the Korean Intellectual Property Office, the entire disclosure of which is incorporated herein by reference in its entirety for all purposes.

BACKGROUND

1. Field

The following disclosure relates to a Neq hot-start (HS) DNA polymerase in which inteins of a Neq L fragment and a Neq S fragment derived from *Nanoarchaeum equitans* are linked, and more particularly, to development of mutant Neq HS DNA polymerases having a highly improved PCR amplification rate.

2. Discussion of Related Art

Deoxyribonucleic acid (DNA) polymerases (Enzyme Commission (E.C.) number 2.7.7.7) are enzymes which synthesize a DNA sequence complementary to a template DNA strand in a 5'→3' direction, and play the most important role in DNA replication or repair in living organisms. The DNA polymerases may be classified into at least six families (families A, B, C, D, X, and Y), based on their amino acid sequences. Most of the DNA polymerases belonging to the family B can initiate replication with high fidelity since they have a 3'→5' exonuclease activity referred to as proofreading activity. With the development of PCR techniques using thermostable DNA polymerases, attention has been directed to thermostable DNA polymerases. Thus, various thermostable DNA polymerases from thermophiles and hyperthermophiles have been developed. In particular, thermostable DNA polymerases from hyperthermophilic archaea such as *Thermococcus litoralis*, *Pyrococcus furiosus* and the like have been used in PCR requiring high-fidelity amplification since such thermostable DNA polymerases have a 3'→5' exonuclease activity referred to as proofreading activity as well as a DNA polymerization activity.

An intein is a protein insertion sequence that is present within a precursor protein sequence. Since an intein sequence is removed from a precursor protein through a self-splicing process, such intein sequence does not affect the structure and activities of the final protein made from the precursor protein. Protein splicing is a process occurring after translation of proteins. During this process, the intein sequences are consistently removed from the precursor protein by means of a self-splicing action, and extein—domains constituting the final protein exhibiting activities—are linked to each other through a normal peptide bond in the process.

*Nanoarchaeum equitans* is a nano-sized anaerobe initially isolated from a submarine hot vent at the Kolbeinsey ridge in Iceland. This strain is a living organism that parasitically grows on the surface of a specific host, *Ignicoccus* sp. strain KIN4/I, under strict anaerobic conditions.

It was reported that Neq DNA polymerase is present in the *N. equitans* genome and is composed of two genes, separated by 83,295 bp, coding for the Neq DNA polymerase. That is, the DNA polymerase is coded by an extein-coding region and a split mini-intein-coding region. Neq DNA polymerase is produced by two genes which code for a large fragment (Neq L) and a small fragment (Neq S) of the Neq DNA polymerase. That is, polypeptides are expressed from each of the two genes which are separately present on the genome, and are linked by a peptide bond through protein trans-splicing, thereby yielding an active DNA polymerase. The large fragment (Neq L) of the Neq DNA polymerase consists of an extein domain composed of 578 amino acid residues, and an intein domain composed of 98 amino acid residues, which participates in the protein trans-splicing, and corresponds to an amino-terminal part (N-terminal part) of the Neq DNA polymerase (Korean Patent No. 10-0793007 and U.S. Pat. No. 7,749,732). Also, the small fragment (Neq S) of the Neq DNA polymerase consists of an intein domain composed of 30 amino acid residues, and an extein domain composed of 223 amino acid residues, and corresponds to a carboxyl-terminal part (C-terminal part) of the Neq DNA polymerase. The genes coding for the large fragment and the small fragment of the Neq DNA polymerase were cloned into one expression vector, and expressed in *Escherichia coli*. Then, the *E. coli* strain was collected, and homogenized by sonication. Thereafter, it was confirmed that a trans-splicing reaction occurred at a high temperature through SDS-PAGE and enzymatic activities. That is, a protein in which inteins were removed through protein trans-splicing at a high temperature and having only exteins linked through a peptide bond was designated Neq C (in the protein trans-spliced form of Neq DNA polymerase). Also, a DNA polymerase produced by recombining an extein-coding region of the Neq L fragment gene, from which an intein-coding region was removed, with an extein-coding region of the Neq S fragment gene, from which an intein-coding region was removed, and expressing the recombinant as a single polypeptide chain was designated Neq P (in a genetically protein splicing-processed form of Neq DNA polymerase). It was reported that the Neq C and Neq P were prepared through different methods, but were enzymes exhibiting the same activities and biochemical characteristics.

Also, when the recombinant vectors expressing the Neq L and S fragments were constructed, and the Neq L and S fragments were expressed in *E. coli*, purified, and added together, it was found that a trans-splicing reaction occurred at a high temperature through SDS-PAGE and enzymatic activities (Korean Patent No. 10-0793007; and U.S. Pat. No. 7,749,732). Also, it has been reported that each of the Neq L and S fragments was purified, and applied to hot-start PCR, based on the fact that the Neq L and S fragments were trans-spliced at a high temperature (Korean Patent No. 10-1230362).

The N-terminal domain of an archaea-derived family-B DNA polymerase contains a specialized pocket that discriminates the deaminated bases such as uracil and hypoxanthine (Fogg M. J. et al., 2002, *Nat. Struct. Biol.* 9: 922-927; Gill S. et al., 2007, *J. Mol. Biol.* 372: 855-863). This specialized pocket scans for the presence of uracil; and, on encountering uracil, DNA synthesis is stalled. However, the Neq DNA polymerase has a different structure than the other family-B DNA polymerases. The Neq DNA polymerase is an archaea-derived family-B DNA polymerase that has no pocket recognizing a uracil base and thus can successfully utilize deaminated bases. In this regard, a method of preparing a Neq-plus DNA polymerase-which is a combination of Neq DNA polymerase and Taq DNA polymerase—and PCR applications using uracil-DNA glycosylase (UDG) and dUTP have been reported recently (see Choi J. J. et al., 2008, *Appl. Envirn. Microbio.* 74: 6563-6569).

As a method of preventing occurrence of crossover contamination in PCR, Longo M. C. et al. suggested a method of performing PCR using dUTP instead of dTTP (Longo M. C. et al., 1990, *Gene* 93: 125-128). Also, PCR methods, which include treating template DNA with UDG in order to remove a trace amount of contaminated uracil-containing DNA in a sample before initiation of PCR, and inactivating the UDG through heating, and performing PCR using dUTP instead of dTTP, have been reported (Rys P. N. and D. H. Persing. 1993. *J. Clin. Microbiol.* 31: 2356-2360). As a result, PCR products which are treated with UDG during a PCR procedure or include UDG tend to be currently commercially available.

In recent years, one of the most important techniques in the PCR-related industries is a hot-start (HS) PCR. HS PCR has been used in various fields such as identification of infectious diseases (e.g. HIV), amplification of DNA with low purity, real-time PCR, one-step RT-PCR, etc., and various studies of enzymes associated with the HS PCR have also been conducted. HS PCR is a PCR method in which DNA polymerase activities are inhibited at a low temperature in a procedure of mixing PCR reaction components or an initial PCR denaturation procedure. But DNA polymerase activities are allowed at a temperature greater than or equal to a primer annealing temperature (approximately 55 to 65° C.). That is, in typical PCR procedures non-specific primer binding takes place when a temperature increases during a procedure of mixing PCR components and an initial PCR denaturation procedure. In this case, undesired PCR products are produced by the activities of the polymerase, and thus the undesired PCR products compete with PCR products of interest in a subsequent PCR reaction and interfere with detection of the PCR product of interest. This non-specific amplification is an especially severe barrier in aspects of detecting target DNA present in a low number of copies, amplifying a low concentration of a DNA sample, and performing multiplex PCR using various primers at the same time. HS PCR was developed to avoid undesired PCR products produced by non-specific priming during this initial PCR procedure. In this case, since the DNA polymerase is active at a temperature greater than or equal to a primer annealing temperature, it is possible to enhance specificity of the PCR products.

An HS PCR method that has been used is a manual method. This method is to add one of the components necessary for PCR (for example, $MgCl_2$, Taq DNA polymerase, dNTP, and the like) at an elevated temperature at the beginning of the PCR procedure. However, the method has various problems in that it cannot be used when there are a large number of samples to be treated. A method subsequently developed includes separately preparing main components of PCR using wax and performing PCR while mixing the separately prepared components and melting the wax through heating. This method has problems in that the wax should be melted and added, and may serve as a barrier in separating the PCR products after a PCR reaction, and a total amount of a reaction solution may be increased by addition of the wax. Another method which was the most commercially successful and has been used by some companies such as Invitrogen is a method using an antibody against Taq DNA polymerase. The method may have an effect of inhibiting the activities of the polymerase since the antibody reacts with the enzyme at room temperature, and PCR proceeds due to the activities of the enzyme since the antibody is denatured due to a gradual increase in temperature, and thus is separated from the enzyme. That is, since an increase in temperature allows primers to bind to target DNA at an accurate position, only the target DNA of interest can be specifically amplified. However, this method has problems in that it requires an excessive amount of the antibody, and the antibody is also very expensive.

Still another method developed is a method using a chemically modified DNA polymerase. This technique was developed separately by Roche (U.S. Pat. No. 5,677,152) and Qiagen (U.S. Pat. No. 6,183,998), and has approximately 68% of the HS PCR market share in the U.S. In this method, the Taq DNA polymerase is inactive due to chemical modification, but becomes active again through an initial reactivation procedure (at 95° C. for 10 minutes) of the PCR reaction, thereby enabling PCR. However, this method also has problems in that only approximately 30% of the enzyme is reactivated at an initial stage of the PCR reaction, and it is impossible to amplify a long DNA sequence due to depurination of the template DNA upon reactivation at a high temperature. In spite of the problems of the method, the chemically modified enzyme is currently being used due to convenience of use. Other methods include a method of specifically designing heat-activated primers (Lebedev A. V. et al., 2008, *Nucleic Acids Research* 36: No. 20 e131), a magnesium precipitation method (see Barnes W M and Rowlyk K R. *Molecular and Cellular Probes* 16: 167-171) (using a high concentration of Mg, but it is impossible to use Mg at an accurate concentration), the use of pyrophosphatase and pyrophosphate (Bioneer, Korean Patent Application No. 10-2007-01090055), and the like. None of these methods was very successful since they all have critical problems.

There has been a demand for development of new techniques by which HS PCR can be performed effectively at a low manufacturing cost. Based on the fact that a trans-splicing reaction takes place at a high temperature when Neq L and Neq S fragments of the Neq DNA polymerase (both of which contain inteins) are added together, the present inventors have applied the trans-splicing reaction to HS PCR for the first time so as to satisfy these requirements (Korean Patent No. 10-1230362; and US Patent Publication No. 2012/0135472). That is, the HS PCR method referenced above is based on a new concept for explaining that a DNA polymerase has no activities since protein trans-splicing does not occur at a low temperature. But inteins are removed through trans-splicing at a high temperature (60° C. or more; an optimal temperature of 80° C.) and only exteins are linked by means of a peptide bond to form an active Neq DNA polymerase (Korean Patent No. 10-1230362). However, in such method, the Neq L and Neq S fragments should be separately purified, and should be added to a PCR reaction solution at accurate concentrations. Also, in the method, a PCR amplification rate is slow since wild-type Neq L and Neq S fragments are used.

SUMMARY

This Summary is provided to introduce a selection of concepts in a simplified form that are further described below in the Detailed Description. This Summary is not intended to identify key features or essential features of the claimed subject matter.

It is an object of the present disclosure to provide a method of preparing a Neq hot-start (HS) DNA polymerase in the form of a precursor of Neq DNA polymerase in which inteins of Neq L and Neq S fragments are linked so as to solve the problems caused when the Neq L and Neq S fragments are separately purified and added at an accurate mixing ratio in a conventional HS PCR method using trans-splicing. Also, it is an object of the present disclosure to develop mutant Neq HS DNA polymerases having a significantly improved PCR amplification rate by reinforcing a conventional HS PCR method using wild-type Neq L and Neq S fragments having a low PCR amplification rate.

However, the objects of the present disclosure are not limited thereto, and the features and aspects will become more apparent to those of ordinary skill in the art from the following detailed description, the drawings, and the claims.

In a general aspect, a thermostable hot-start DNA polymerase (Neq HS DNA polymerase) derived from a *Nanoarchaeum equitans* strain is provided wherein the Neq HS DNA polymerase includes a Neq L fragment and a Neq S fragment in which inteins of the Neq L fragment and the Neq S fragment are linked with each other, wherein the Neq HS DNA polymerase has an amino acid sequence set forth in SEQ ID NO: 6, SEQ ID NO: 32, SEQ ID NO: 34, or SEQ ID NO: 36.

The Neq HS DNA polymerase having the amino acid sequence set forth in SEQ ID NO: 32, SEQ ID NO: 34, or SEQ ID NO: 36 may be a mutant of the Neq HS DNA polymerase having an amino acid sequence set forth in SEQ ID NO: 6.

In a general aspect, a gene is provided having a base sequence selected from the group consisting of SEQ ID NO: 5, SEQ ID NO: 31, SEQ ID NO: 33, and SEQ ID NO: 35, which codes for the Neq HS DNA polymerase.

In a general aspect, a recombinant vector is provided carrying the gene coding for the Neq HS DNA polymerase, wherein the recombinant vector is a vector in which a T7 promoter is replaced with a tryptophan promoter.

The recombinant vector is provided wherein the recombinant vector is selected from the group consisting of pETRPNEQHS, pETRPNEQHSM1, pETRPNEQHSM2, and pETRPNEQHSM3.

In a general aspect, a transformant, *E. coli* W3110-RILYKT/pETRPNEQHS (Accession No.: KCCM1448P), obtained by transforming an *E. coli* W3110 strain with the recombinant vector pETRPNEQHS is provided.

In a general aspect, a transformant, *E. coli* W3110-RILYKT/pETRPNEQHSM3 (Accession No.: KCCM1449P), obtained by transforming an *E. coli* W3110 strain with the recombinant vector pETRPNEQHSM3 is provided.

In a general aspect, a method of preparing a thermostable Neq HS DNA polymerase includes i) preparing a recombinant vector expressing the Neq HS DNA polymerase; ii) transforming a host cell with the recombinant vector; iii) culturing the transformant; and iv) purifying the Neq HS DNA polymerase from the transformant.

In a general aspect, a method of performing a hot-start polymerase chain reaction (HS PCR) through intein splicing using the Neq HS DNA polymerase is provided, wherein the hot-start PCR exhibits activity at pH 6.0 to 9.0, a $Mg^{2+}$ concentration of 0.5 to 1.5 mM, and a KCl concentration of 60 to 100 mM.

In a general aspect, a method of performing a hot-start PCR at a temperature of about 50 to 100° C. through intein splicing is provided, wherein the hot-start PCR is performed using a thermostable chimeric Nefu HS DNA polymerase prepared by linking the N terminus and the full-length inteins of the Neq HS DNA polymerase with Pfu-C that is a C-terminal domain of the Pfu DNA polymerase.

BRIEF DESCRIPTION OF THE DRAWINGS

FIG. 4A shows the SDS-denatured gel electrophoresis results according to a step of purifying a Neq HS DNA polymerase expressed in *E. coli*. Here, Lane 1 represents a sonicated sample of an *E. coli* W3110-RILYKT/pETRPNEQHS strain cultured in an LB medium, Lane 2 represents a sonicated sample of the *E. coli* W3110-RILYKT/pETRPNEQHS strain cultured in an M9 defined medium supplemented with 0.1% glucose and 0.5% casamino acid, Lane 3 represents a sample after HisTrap™ HP column chromatography, Lane 4 represents a sample after HiTrap™ Q HP column chromatography, and Lane 5 represents a sample after HiTrap™ SP HP column chromatography. FIG. 4B is a purification image of mutant Neq HS DNA polymerases purified in the same manner as in the step of purifying a Neq HS DNA polymerase. Here, Lane 1 represents a Neq HS DNA polymerase, Lane 2 represents a Neq HS M DNA polymerase, Lane 3 represents a Neq HS M2 DNA polymerase, and Lane 4 represents a Neq HS M3 DNA polymerase.

Figure 1:
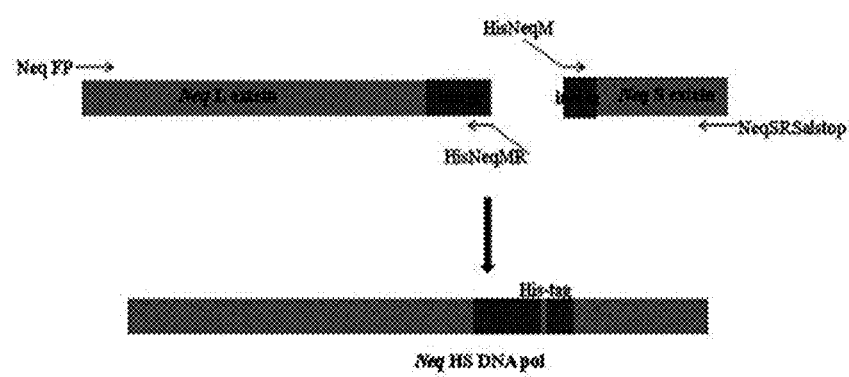
FIG. 1 is a diagram illustrating a Neq HS DNA polymerase in the form of a precursor of Neq DNA polymerase obtained by linking inteins of Neq L and Neq S fragments with each other.

Throughout the drawings and the detailed description, unless otherwise described or provided, the same drawing reference numerals will be understood to refer to the same elements, features, and structures. The drawings may not be to scale, and the relative size, proportions, and depiction of elements in the drawings may be exaggerated for clarity, illustration, and convenience.

DETAILED DESCRIPTION

The following detailed description is provided to assist the reader in gaining a comprehensive understanding of the methods, apparatuses, and/or systems described herein. However, various changes, modifications, and equivalents of the systems, materials and/or methods described herein will be apparent to one of ordinary skill in the art. The progression of processing steps and/or operations described is an example; however, the sequence of and/or operations is not limited to that set forth herein and may be changed as is known in the art, with the exception of steps and/or operations necessarily occurring in a certain order. Also, descriptions of functions and constructions that are well known to one of ordinary skill in the art may be omitted for increased clarity and conciseness.

The features described herein may be embodied in different forms, and are not to be construed as being limited to the examples described herein. Rather, the examples described herein have been provided so that this disclosure will be thorough and complete, and will convey the full scope of the disclosure to one of ordinary skill in the art.

Unless specifically stated otherwise, all the technical and scientific terms used in this specification have the same meanings as what are generally understood by a person skilled in the related art to which the present disclosure belongs. In general, the nomenclatures used in this specification and the experimental methods described below are widely known and generally used in the related art.

The present inventors have previously designed a new concept of an HS PCR method based on the fact that a trans-splicing reaction occurs at a high temperature when a Neq L fragment carrying an intein of a Neq DNA polymerase is added together with a Neq S fragment. In this method, the Neq L and Neq S fragments should be purified separately and added to a PCR reaction solution at an accurate mixing ratio. Also, in this method, the DNA of interest may be amplified from a human genome with more accuracy, and the manufacturing cost is low, compared to the products for HS PCR using monoclonal antibodies currently commercially available. However, in some cases it is difficult for a group of general researchers to use such method since the Neq L and Neq S fragments should be separately expressed and purified, and also may require constant adjustment of the ratios of the Neq L and Neq S fragments for PCR reaction.

Also, the Neq S fragment is produced in the form of an inclusion body when expressed in E. coli. It is difficult to obtain a large amount of Neq S fragment since the Neq S fragment purified from such an inclusion body easily precipitates during dialysis.

Therefore, an object of the present disclosure is to prepare a Neq HS DNA polymerase in the form of a precursor of Neq DNA polymerase by linking inteins of the Neq L and Neq S fragments with each other in order to solve the various challenges regarding the separate use of the Neq L and Neq S fragments in a PCR reaction. Another object of the present disclosure is to develop mutant Neq HS DNA polymerases having a significantly improved PCR amplification rate by reinforcing a conventional HS PCR method using wild-type Neq L and Neq S fragments having a low PCR amplification rate.

That is, the present disclosure provides a thermostable Neq HS DNA polymerases derived from a Nanoarchaeum equitans strain in which inteins of Neq L and Neq S fragments are linked with each other. Here, the Neq HS DNA polymerase has an amino acid sequence set forth in SEQ ID NO: 6, SEQ ID NO: 32, SEQ ID NO: 34, or SEQ ID NO: 36.

In particular, a purification method using a His-tag affinity column may be significantly improved by inserting a His-tag sequence composed of six histidine residues between the inteins of the Neq L and Neq S fragments at the gene level upon construction of a Neq HS DNA polymerase gene. In this manner, since the His-tag sequence of six histidine residues is inserted into the inteins, the His-tag sequence is autonomously removed during a splicing process of the Neq HS DNA polymerase. Therefore, the His-tag sequence does not affect the structure and activities of the Neq HS DNA polymerase at all. Then, the Neq HS DNA polymerase is added to an enzymatic reaction solution to analyze a protein-splicing effect according to a reaction temperature and a reaction time and compare the activities of the Neq HS DNA polymerases. As a result, it is revealed that the normal Neq DNA polymerases are produced only at a high temperature.

According to one exemplary embodiment of the present disclosure, the DNA polymerase exhibits optimal activities at pH 6.0 to 9.0, a $Mg^{2+}$ concentration of 0.5 to 1.5 mM, and a KCl concentration of 60 to 100 mM, but the present disclosure is not limited thereto.

Also, the present disclosure may provide a gene having a base sequence set forth in SEQ ID NO: 5, SEQ ID NO: 31, SEQ ID NO: 33, or SEQ ID NO: 35, which codes for the DNA polymerase.

According to one exemplary embodiment of the present disclosure, an RILYKT tRNA plasmid is constructed and introduced into an expression host to enhance an expression level of the Neq HS DNA polymerase. To improve PCR efficiency, mutations are also induced at specific positions of a Neq HS DNA polymerase gene to screen mutant Neq HS DNA polymerases (M1, M2, and M3) having a high PCR amplification rate and a high amplification level.

In an optimized HS PCR method using the Neq HS M3 DNA polymerase among the mutant Neq HS DNA polymerases, it is revealed that the Neq HS M3 DNA polymerase exhibits an excellent characteristic of selectively amplifying target DNA with high accuracy without amplification of non-specific products, compared to the commercially available HS Taq DNA polymerases and Pfu DNA polymerases. Also, it is revealed that the HS PCR using the Neq HS DNA polymerases may amplify the DNA of interest more selectively than the DNA polymerases used in other HS PCR methods using dUTP.

Accordingly, still another object of the present disclosure is to provide information on a base sequence coding for the Neq HS DNA polymerase including the intein. More particularly, the object of the present disclosure is directed to a DNA molecule coding for the Neq HS DNA polymerase having an amino acid sequence set forth in SEQ ID NO: 6. Here, the Neq HS DNA polymerase has a DNA sequence set forth in SEQ ID NO: 5. Also, the object of the present disclosure is to provide information on a base sequence coding for a mutant Neq HS M DNA polymerase including the intein (i.e., an enzyme obtained by substituting the alanine at position 523 of the Neq HS DNA polymerase with an arginine residue). More particularly, the object of the present disclosure is directed to a DNA molecule coding for the Neq HS M DNA polymerase. Preferably, the Neq HS M DNA polymerase having an amino acid sequence set forth in SEQ ID NO: 32 has a DNA sequence set forth in SEQ ID NO: 31.

According to another exemplary embodiment of the present disclosure, the present disclosure may also provide information on a base sequence coding for a mutant Neq HS M2 DNA polymerase including the intein (i.e., an enzyme obtained by doubly substituting the alanine at position 523 and the asparagine at position 540 of the Neq HS DNA polymerase with arginine residues, respectively). More particularly, the present disclosure is directed to a DNA molecule coding for the Neq HS M2 DNA polymerase. Preferably, the Neq HS M2 DNA polymerase having an amino acid sequence set forth in SEQ ID NO: 34 has a DNA sequence set forth in SEQ ID NO: 33.

According to still another exemplary embodiment of the present disclosure, the present disclosure may provide information on a base sequence coding for a mutant Neq HS M3 DNA polymerase including the intein (i.e., an enzyme obtained by triply substituting the alanine at position 523, the asparagine at position 540 and the serine at position 185 of the Neq HS DNA polymerase with arginine, arginine and aspartic acid residues, respectively). More particularly, the present disclosure is directed to a DNA molecule coding for the Neq HS M3 DNA polymerase. Preferably, the Neq M3 DNA polymerase having an amino acid sequence set forth in SEQ ID NO: 36 has a DNA sequence set forth in SEQ ID NO: 35.

Also, the present disclosure may provide a method of constructing a tRNA codon plasmid to increase expression levels of the Neq HS DNA polymerase including the intein and mutants thereof.

That is, the present disclosure may provide a recombinant vector containing a gene coding for the DNA polymerase. Here, the recombinant vector is characterized in that a T7 promoter is replaced with a tryptophan promoter.

According to one exemplary embodiment of the present disclosure, the recombinant vector may be pETRPNEQHS (a recombinant vector into which a Neq HS DNA polymerase gene is cloned), pETRPNEQHSM1 (a recombinant vector into which a Neq HS M DNA polymerase gene is cloned), pETRPNEQHSM2 (a recombinant vector into which a Neq HS M2 DNA polymerase gene is cloned), or pETRPNEQHSM3 (a recombinant vector into which a Neq HS M3 DNA polymerase gene is cloned).

Also, the present disclosure may provide a transformant obtained by transforming *E. coli* W3110 with the recombinant vector. Here, the transformant obtained by transforming *E. coli* W3110 with the pETRPNEQHS recombinant vector is *E. coli* W3110-RILYKT (Accession No.: KCCM1448P), and the transformant obtained by transforming *E. coli* W3110 with the pETRPNEQHSM3 recombinant vector is *E. coli* W3110-RILYKT (Accession No.: KCCM1449P).

Accordingly, the present disclosure may provide a method of preparing a thermostable HS DNA polymerase, which includes preparing the recombinant vector, transforming a host cell with the recombinant vector, culturing the transformant, and separating a DNA polymerase from the transformant.

According to still another exemplary embodiment of the present disclosure, the present disclosure provides a method of expressing genes of the Neq HS DNA polymerase including the intein and mutants thereof, and a method of purifying the recombinant Neq HS DNA polymerase and mutants thereof.

Still another object of the present disclosure is to provide a method of performing HS PCR at a high temperature (for example, 50 to 100° C.) using the inteins of the DNA polymerase.

In the present disclosure, when PCR is performed on a 1-actin gene, a 3-globin gene, and a hemoglobin gene in the presence of dNTP or dUTP using the human genomic DNA as a template, it is revealed that the Neq HS M3 DNA polymerase has an HS PCR effect of specifically amplifying only target DNA, compared to the other DNA polymerases.

In particular, since the Neq HS M3 DNA polymerase provided in the present disclosure as described above exhibits more excellent specificity than the commercially available sDNA polymerases (i.e., an HS Taq DNA polymerase) even in multiplex PCR using pairs of primers, the Neq HS DNA polymerase and variants thereof are very suitably used for real-time PCR performed for the purpose of diagnosing diseases.

The Neq HS DNA polymerase according to the present disclosure may be used as a component of a PCR kit when the Neq HS DNA polymerase is added to a PCR reaction solution. The PCR kit according to the present disclosure may include at least one component selected from the group consisting of a vessel, amplification reaction tube or container containing a detection primer, a reaction buffer, dNTPs, RNase, and sterile water in addition to the Neq HS DNA polymerase.

The kit including the Neq HS DNA polymerase according to the present disclosure may be more usefully used than the Taq DNA polymerase in various fields such as genetic engineering and molecular biology experiments, clinical diagnoses, forensics, and the like.

The DNA polymerase for HS PCR including an optimal mixture of the Neq HS M3 DNA polymerase according to the present disclosure exhibits higher PCR amplification specificity than the Taq DNA polymerase or the Pfu DNA polymerase in PCR using human genomic DNA as a template. Like the Taq DNA polymerase, the DNA polymerase including the optimal mixture of the Neq HS DNA polymerase may also be used to perform PCR in the presence of dUTP. Particularly, PCR may be performed in the presence of dUTP for a shorter reaction time with higher specificity, compared to the Taq DNA polymerase.

That is, the DNA polymerase including the optimal mixture of the Neq HS DNA polymerase may specifically amplify only a target DNA of interest in the presence of dUTP, and exhibits superior amplification efficiency. In particular, since the DNA polymerase including the optimal mixture of the Neq HS M3 DNA polymerase provided in the present disclosure as described above has higher polymerization activities and amplification specificity in the presence of dUTP than the conventional polymerases (i.e., a Taq DNA polymerase), the DNA polymerase is very suitably used for PCR performed in the presence of UDG and dUTP for the purpose of diagnosing diseases.

Further, the present disclosure provides a thermostable chimeric Nefu HS DNA polymerase in which the N terminus and the full-length inteins of the Neq HS DNA polymerase are linked with a C-terminal fragment (Pfu-C) of the Pfu DNA polymerase by linking the Neq DNA polymerase with another thermostable DNA polymerase, that is, a Pfu DNA polymerase. Here, the thermostable chimeric Nefu HS DNA polymerase has an amino acid sequence set forth in SEQ ID NO: 41.

Also, the present disclosure provides a gene having a base sequence set forth in SEQ ID NO: 40, which codes for the DNA polymerase.

In addition, the present disclosure provides a recombinant vector including the gene coding for the DNA polymerase.

According to one exemplary embodiment of the present disclosure, the recombinant vector is characterized in that it is pETRPNPHS.

Furthermore, the present disclosure provides a method of preparing chimeric DNA polymerases obtained by linking the intein of the DNA polymerase with other DNA polymerases, and a method of performing HS PCR at a high temperature (50 to 100° C.) using the chimeric DNA polymerases including the intein.

Hereinafter, preferred exemplary embodiments of the present disclosure will be described in order to aid in understanding the present disclosure. However, it should be understood that the description set forth herein is merely exemplary and illustrative of exemplary embodiments for the purpose of describing the present disclosure, and is not intended to limit the exemplary embodiments.

Example 1

Preparation of Nee HS DNA Polymerase in the Form of Precursor in which Inteins of Neq L and Neq S Fragments are Linked with Each Other In this Example, the inteins of Neq L and Neq S fragments of a Neq DNA polymerase were linked with each other to prepare a Neq HS DNA polymerase in the form of a precursor of Neq DNA polymerase. Especially as shown in FIG. 1, recombinant Neq HS DNA polymerases were designed to be easily purified through a His-tag affinity column by inserting a His-tag sequence composed of six histidine residues between the inteins of the Neq L and Neq S fragments at a gene level upon construction of a Neq HS DNA polymerase gene.

According to the method disclosed in Korean Patent No. 10-1230362, genes of the Neq L and Neq S fragments cloned into a pET-22b (+) expression vector were ensured, and 4 PCR primers (SEQ ID NOS: 1 to 4) were synthesized based on information on the gene sequence. The Neq L fragment gene and the Neq S fragment gene were linked through an overlap extension PCR method (Reikofski and Tao, 1992).

In this case, the primer set forth in SEQ ID NO: 1 (Neq FP) was prepared by synthesizing a base sequence coding for an amino acid sequence of the N terminus of the Neq L fragment in a 5'→3' direction. SEQ ID NO: 2 (HisNeqM) was prepared by synthesizing a portion of an amino acid sequence (an intein region) of the N terminus of the Neq S fragment, and a His-tag sequence, and a base sequence complementary to the base sequence coding for an amino acid sequence of the intein of the Neq L fragment in a 5'→3' direction. SEQ ID NO: 3 (HisNeqMR) was prepared by synthesizing a portion of an amino acid sequence of the intein of the Neq L fragment, a His-tag sequence, and an amino acid sequence (an intein region) of the N terminus of the Neq S fragment in a 5'→3' direction. SEQ ID NO: 4 (NeqSRSalstop) was prepared by synthesizing a base sequence complementary to a base sequence coding for an amino acid sequence of the C terminus of the Neq S fragment in a 5'→3' direction.

In addition, the primers set forth in SEQ ID NOS: 1 and 4 were synthesized so that the primers had NdeI and SalI sites, respectively, so as to facilitate cloning into the expression vector. First, primary PCR was performed using the Neq L fragment gene as a template after the primers set forth in SEQ ID NOS: 1 and 2 were added to a PCR reaction solution. The PCR reaction solution was composed of 200 μM dNTPs, a 10×PyroAce DNA polymerase buffer, and a 2.5 U Super PyroAce DNA polymerase. The PCR reaction was performed for one cycle of denaturation at 95° C. for 3 minutes, followed by 30 cycles of denaturation at 94° C. for 30 seconds, annealing at 60° C. for 30 seconds, and extension at 72° C. for 2 minutes, and one final cycle of extension at 72° C. for 10 minutes.

Also, the primer set forth in SEQ ID NOS: 3 and 4 were added, and primary PCR was performed in a PCR reaction solution including the Neq S fragment gene in the same manner as described above using the Neq S fragment gene as a template. The resulting PCR amplification products were recovered through agarose gel electrophoresis. The two fragments recovered thus were mixed at the same mixing ratio, added to the same PCR reaction solution as described above, and denatured at 95° C. for 3 minutes. Then the two fragments were annealed by cooling the resulting reaction solution to 50° C., thereby preparing a hybrid template in which overlapping base sequences corresponding to the inteins of the Neq L and Neq S fragments preferentially overlapped. The hybrid template was subjected to overlap extension at 72° C. for 10 minutes to link genes of the Neq L and Neq S fragments with each other. The primers set forth in SEQ ID NOS: 1 and 4 were added to the same PCR reaction solution as described above, and secondary PCR was performed using the linked gene as a template in the same manner as described above, thereby amplifying a full-length Neq HS DNA polymerase gene in which the inteins of the Neq L and Neq S fragments were linked with each other. The amplified Neq HS DNA polymerase gene was digested with restriction enzymes NdeI and SalI, and ligated between the same restriction enzyme sites of an expression vector pET-20b(+). *E. coli* DH5 was transformed with this mixed ligation solution, and plasmid DNA was separated from the resulting transformants using an alkaline lysis method, digested with restriction enzymes NdeI and SalI, and then electrophoresed in 0.8% agarose gel together with a DNA size marker to determine whether the Neq HS DNA polymerase gene was inserted into an exact position of the expression vector. Then, the full-length Neq HS DNA polymerase gene was sequenced. As a result, it was re-confirmed that the Neq HS DNA polymerase gene in which the intein regions of the Neq L and Neq S fragments were precisely linked had a base sequence set forth in SEQ ID NO: 5.

An amino acid sequence of the Neq HS DNA polymerase (SEQ ID NO: 6) was determined based on the base sequence of the Neq HS DNA polymerase gene (SEQ ID NO: 5). The expression vector obtained by precisely cloning the Neq HS DNA polymerase gene into pET-20b(+) was designated as pETNEQHS.

```
(Neq FP):
                                          SEQ ID NO: 1
5'-ATTATAGCATATGTTACACCAACTCCCCACG-3'

(HisNeqM):
                                          SEQ ID NO: 2
5'-ATGTGGTGATGGTGATGGTGATTATTTTTATT

TTCATATTCCTTGGC-3'

(HisNeqMR):
                                          SEQ ID NO: 3
5'-AATCACCATCACCATCACCACAATGCGCTATC

TTGGCAAAAAGAGAG-3'

(NeqSRSalstop):
                                          SEQ ID NO: 4
5'-NNNNNNGTCGACTTTAAAGAAATCTGTTA GTTTTTT-3'
```

To express the Neq HS DNA polymerase gene, *E. coli* BL21-CodonPlus (DE3)-RIL was transformed with the expression vector pETNEQHS. The *E. coli* BL21-CodonPlus (DE3)-RIL/pETNEQHS strain was seeded in an LB culture broth supplemented with ampicillin and chloramphenicol at final concentrations of 100 μg/ml and 34 μg/ml, respectively, and cultured at 37° C. When a concentration of the strain reached 0.6 at $OD_{600}$, isopropyl-D-thiogalactopyranoside (IPTG) was added at a final concentration of 0.5 mM to induce expression of proteins for 6 hours or more, and the expression of proteins was analyzed through SDS-PAGE. However, the Neq HS DNA polymerase gene was hardly expressed in the *E. coli* BL21-CodonPlus (DE3)-RIL/pETNEQHS carrying the pETNEQHS.

Figure 2A:
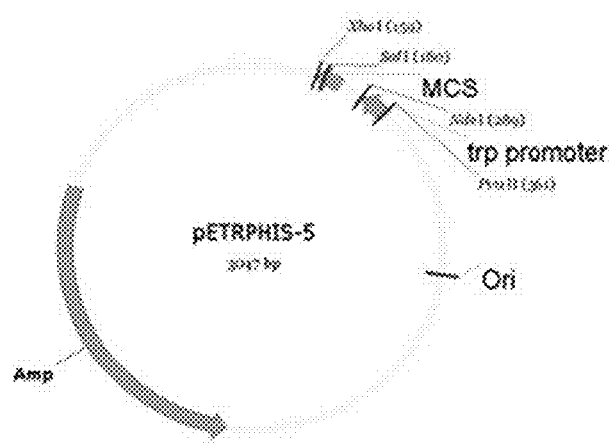
FIG. 2A is a diagram illustrating the construction of an expression vector pETRPHIS-5 (FIG. 2A, SEQ ID NO: 9). Here, a promoter is a tryptophan (trp) promoter derived from *E. coli* W3110.

Therefore, as another vector system used to express the Neq HS DNA polymerase gene, a vector in which a T7 promoter was replaced with a tryptophan (trp) promoter was constructed, as follows. Primers set forth in SEQ ID NO: 7 (TrpPFPvuII) and SEQ ID NO: 8 (TrpPRNdeI-2) were synthesized based on the base sequence of the *E. coli* trp promoter (Miozzari, G. and Yanofsky, C., 1978 *Proc. Natl. Acad Sci. USA* 75, 5580-5584). Together with the primers of SEQ ID NO: 7 and SEQ ID NO: 8, the genomic DNA of *E. coli* W3110 was added as template DNA to the same PCR reaction solution as described above, and a 69-bp-length trp promoter domain was amplified using a PCR method. Then, the amplified trp promoter domain was digested with PvuII and NdeI, and separated through agarose gel electrophoresis. The DNA fragment of the 69-bp-length trp promoter domain was digested with PvuII and NdeI, and ligated into a site of a 2978-bp-length vector pET-20b(+) from which a Ti promoter domain was removed. *E. coli* DH5a was transformed with the mixed ligation solution, and plasmid DNA was separated from the resulting transformants using an alkaline lysis method. Thereafter, the expression vector was sequenced to determine whether the trp promoter domain was exactly cloned into the expression vector. The expression vector with the trp promoter thus was designated as pETRPHIS-5 (SEQ ID NO: 9). For reference, a distance between a Shine-Dalgarno sequence (AAGGGT) and an initiation codon (ATG) was 5 bp (FIG. 2A).

```
(TrpPFPvuII):
                                          SEQ ID NO: 7
5'-NNNNNNCAGCTGATGAGCTGTTGACAATTA ATCATCG-3'

(TrpPRNdeI-2):
                                          SEQ ID NO: 8
5'-NNNNNNCATATGATACCCTTTTTACGTGA ACTTG-3'
```

Figure 2B:
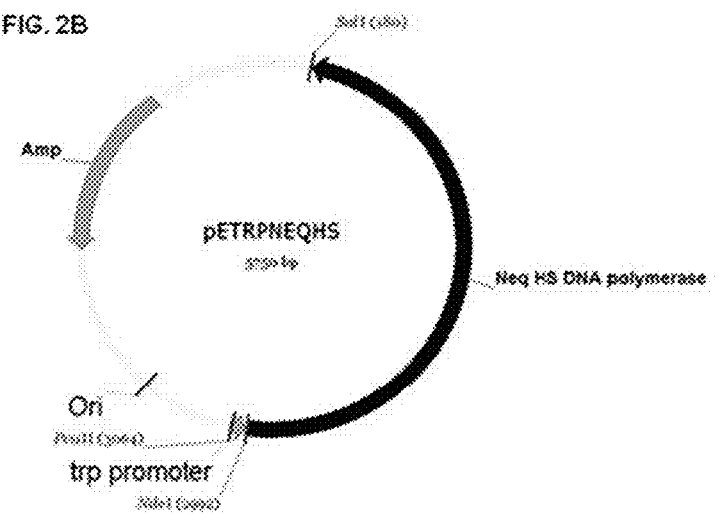
FIG. 2B shows a plasmid pETRPNEQHS obtained by cloning a gene coding for Neq HS DNA polymerase into an expression vector pETRPHIS-5.

The Neq HS DNA polymerase gene was amplified using a PCR method, and the resulting PCR product was digested with restriction enzymes NdeI and SalI, and ligated between the NdeI and SalI sites of the pETRPHIS-5 constructed thus. *E. coli* W3110 was transformed with the mixed ligation solution, and plasmid DNA was separated from the transformants using an alkaline lysis method, and then digested with NdeI and SalI. Clones with the correct construct were selected. The resultant expression vector carrying the Neq HS DNA polymerase gene was named pETRPNEQHS (FIG. 2B).

Example 2

Construction of tRNA Codon Plasmid RILYKT to Increase Expression Level of Neq HS DNA Polymerase Gene

Figure 3A:
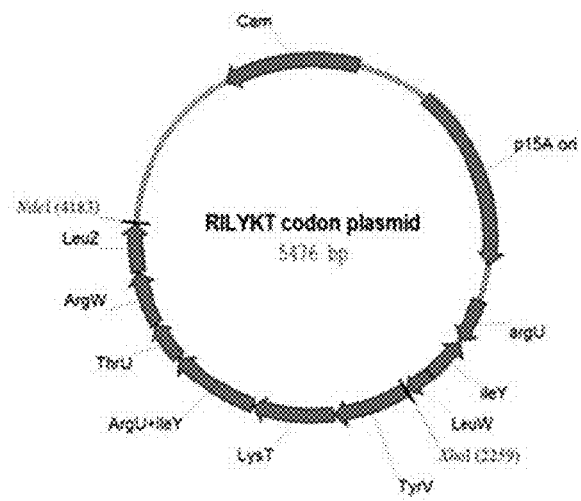
FIG. 3A is a diagram illustrating the construction of an RILYKT tRNA codon plasmid (SEQ ID NO: 24).
Figure 3B:
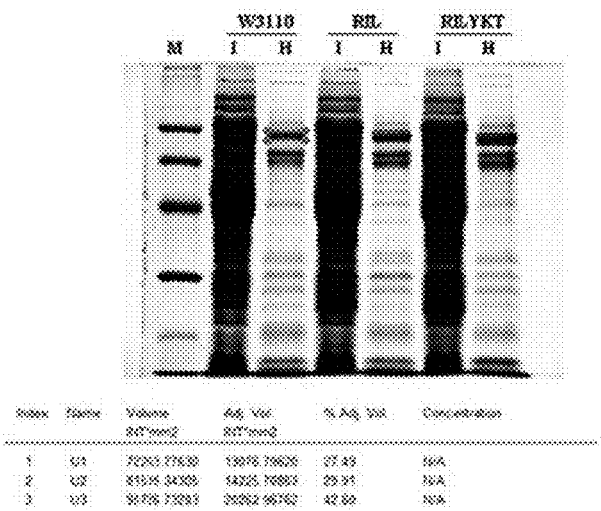
FIG. 3B shows an increase in expression level of Neq HS DNA polymerase when *E. coli* W3110 is transformed with an RILYKT tRNA codon plasmid and pETRPNEQHS.

*E. coli* W3110 was transformed with the newly constructed expression vector expressing the Neq HS DNA polymerase gene in the presence of ampicillin to screen transformants (*E. coli* W3110/pETRPNEQHS). Thereafter, the screened transformants were cultured at 37° C. for approximately 20 hours in an M9 minimal medium supplemented with 0.1% glucose and 0.5% casamino acid, and analyzed through SDS-PAGE. As a result, it was revealed that the Neq HS DNA polymerase gene was expressed (FIG. 3B). However, since the Neq HS DNA polymerase gene had a low expression level, the codon frequencies between the Neq HS DNA polymerase and an *E. coli* strain were examined to enhance an expression level of the gene. As a result, the codons exhibiting a significant difference in codon frequencies were compared and are summarized in the following Table 1.

TABLE 1

Comparative analysis of codons exhibiting a significant difference in codon frequency between Neq HS DNA polymerase and *E. coli* strain

| Codon | Amino acid | E. coli strain Frequency (%) | Neq DNA polymerase gene Frequency (%) | Number of amino acids | Neq/ E. coli (%) |
|---|---|---|---|---|---|
| AGA | Arg (R) | 0.2 | 2.24 | 21 | 11.2 |
| AUA | Ile (I) | 0.4 | 5.97 | 56 | 14.9 |
| CUA | Leu (L) | 0.3 | 1.6 | 15 | 5.3 |
| UAU | Tyr (Y) | 1.6 | 5.86 | 55 | 3.5 |
| AAA | Lys (K) | 3.8 | 10.13 | 95 | 2.67 |
| ACA | Thr (T) | 0.1 | 1.49 | 14 | 14.9 |
| AGG | Arg (R) | 0.2 | 1.49 | 14 | 7.45 |
| UUA | Leu (L) | 1 | 4.58 | 43 | 4.58 |

In particular, the usage frequencies of the codons (AGA (Arg), AUA (Ile), CUA (Leu), UAU (Tyr), AAA (Lys), ACA (Thr), AGG (Arg), and UUA (Leu)) of the Neq HS DNA polymerase were 2.67 to 14.9 times the corresponding frequencies of codons used in *E. coli* genes (see Table 1). Therefore, a pACYC-LIC vector (hereinafter referred to as an 'RIL codon plasmid,' see PCT/US2000/002002) carrying base sequences of tRNA genes for argU, ileY and leuW assigning the *E. coli* codons AGA (Arg), AUA (Ile), and CUA (Leu) was first separated from a commercially available *E. coli* BL21 codonPlus(DE3)-RIL strain (Stratagene), and *E. coli* W3110 was transformed with the pACYC-LIC vector, and grown in the presence of chloramphenicol to prepare *E. coli* W3110-RIL. This strain was transformed with the expression vector expressing the Neq HS DNA polymerase gene, pETRP-NEQHS, and the transformants (*E. coli* W3110-RILpETRP-NEQHS) were screened in the presence of ampicillin and chloramphenicol. In the case of the transformants (*E. coli* W3110-RIL/pETRPNEQHS), an RIL codon plasmid carrying tRNA genes (argU, ileY, and leuW) corresponding to three codons, that is, AGA (Arg), AUA (Ile), and CUA (Leu), was added into an *E. coli* W3110 host. The strain was cultured at 37° C. for approximately 20 hours in an M9 minimal medium supplemented with 0.1% glucose and 0.5% casamino acid (including ampicillin and chloramphenicol), and analyzed through SDS-PAGE. The SDS-PAGE analysis was performed using a Quantity One (Bio-rad) program. The analysis results showed that the expression level increased by approximately 8%, compared to the *E. coli* W3110/pETRP-NEQHS. Therefore, the tRNA genes (tyrV, lysT, argU-ileY, thrU, argW, and leuZ) assigning the other codons UAU (Tyr), AAA (Lys), AGA (Arg), AUA (Ile), ACA (Thr), AGG (Arg), and UUA (Leu), which exhibited a difference in codon frequencies, were further inserted into the RIL codon plasmid to construct an RILYKT codon plasmid (FIG. 3A) according to a method to be described below.

In particular, since a relatively large number of the codons AGA (Arg) and AUA (Ile) were required, the tRNA genes assigning argU and ileY were inserted once again. To understand information on RIL codon plasmid genes, first, an RIL codon plasmid was separated from *E. coli* BL21-CodonPlus (DE3)-RIL to perform DNA base sequencing. Thereafter, the positions of the restriction enzyme sites and the *E. coli* argU, ileY and leuW tRNA genes inserted into the expression vector were determined. Subsequently, the *E. coli* argU, ileY and leuW tRNA genes in the RIL codon plasmid were inserted into a SpeI/XhoI site under the control of a tet promoter (see PCT/US2000/002002). Therefore, an NdeI site was added 32 bp downstream from an XhoI site to be used as a cloning site in the future, as follows. An RIL-Nde codon plasmid having an NdeI site (underlined) inserted thereto was constructed through a PCR method using a QuikChange site-directed mutagenesis method using a primer set forth in SEQ ID NO: 10 and a primer complementary (SEQ ID NO: 11) to that primer set forth in SEQ ID NO: 10.

SEQ ID NO: 10
(tRNA Nde): 5'-CTGGCCACGGGTG<u>CATATG</u>ATCGTGCTCC-3'

SEQ ID NO: 11
(tRNA NdeR): 5'-GGAGCACGAT<u>CATATG</u>CACCCGTGGCCAG-3'

Next, to construct an RILYKT codon plasmid, PCR primers used to amplify *E. coli* tRNA genes such as tyrV, lysT, argU-ileY, thrU, argW, and leuZ assigning the codons UAU (Tyr), AAA (Lys), AGA (Arg), AUA (Ile), ACA (Thr), AGG (Arg), and UUA (Leu) were designed, as follows. To amplify DNA fragment (precursor of a tyrV gene) containing a tRNA gene tyrV of *E. coli* (Note: 370 bp: positions 128640 to 1286760 in the base sequence with GenBank Accession No. U00096) through PCR, the primers set forth in SEQ ID NOS: 12 and 13 were synthesized. For reference, an XhoI restriction site (underlined) was inserted into the primer set forth in SEQ ID NO: 12 to clone the tRNA gene into an RIL-Nde codon plasmid.

(tRNA YXhoF):
SEQ ID NO: 12
5'-NNNNNNN<u>CTCGAG</u>CCTTCCCCGCATGGGCAGAA-3'

(tRNA YKR):
SEQ ID NO: 13
5'-GTTAGCACCCGCCGTGCCACCACCATAATTCAC-3'

To amplify DNA fragment (precursor of a lysT gene) containing a tRNA gene lysT of *E. coli* (400 bp: positions 2726261 to 2725862 in the base sequence with GenBank Accession No. U00096) through PCR, the primers set forth in SEQ ID NOS: 14 and 15 were synthesized.

(tRNA YKF):
SEQ ID NO: 14
5'-GTGAATTATGGTGGTGGCACGGCGGGTGCTAAC-3'

(tRNA KRR):
SEQ ID NO: 15
5'-GAACGACCGCGTCTGATTGACTCACCCTGCCCCG-3'

To amplify DNA fragment containing a tRNA gene argU-ileY of *E. coli* (437 bp: positions 1674 to 2110 in the base sequence of a pACYC-LIC vector) through PCR, the primers set forth in SEQ ID NOS: 16 and 17 were synthesized.

(tRNA KRF):
SEQ ID NO: 16
5'-CGGGGCAGGGTGAGTCAATCAGACGCGGTCGTTC-3'

(tRNA ITR):
SEQ ID NO: 17
5'-TTGCATAATTTGTTTTATTGTCATCATGTTTATTGCGTGG-3'

To amplify DNA fragment (precursor of a thrU gene) containing a tRNA gene thrU of *E. coli* (200 bp: positions 4173340 to 4173539 in the base sequence with GenBank Accession No. U00096) through PCR, the primers set forth in SEQ ID NOS: 18 and 19 were synthesized.

(tRNA ITF):
SEQ ID NO: 18
5'-CCACGCAATAAACATGATGACAATAAAACAAATTATGCAA-3'

(tRNA TRR):
SEQ ID NO: 19
5'-CCATTTATGCCGGGTTTTGGCAGATTTACAGTCTGC-3'

To amplify DNA fragment (precursor of a argW gene) containing a tRNA gene argW of *E. coli* (270 bp: positions 2464242 to 2464511 in the base sequence with GenBank Accession No. U00096) through PCR, the primers set forth in SEQ ID NOS: 20 and 21 were synthesized.

(tRNA TRF):
SEQ ID NO: 20
5'-GCAGACTGTAAATCTGCCAAAACCCGGCATAAATGG-3'

(tRNA RLR):
SEQ ID NO: 21
5'-ATCACCAGCAAAGCCACGCGGCTGTCAACGATC-3'

To amplify DNA fragment (precursor of a leuZ gene) containing a tRNA gene leuZ of *E. coli* (240 bp: positions 1989717 to 1989956 in the base sequence with GenBank Accession No. U00096) through PCR, the primers set forth in SEQ ID NOS: 22 and 23 were synthesized. For reference, an NdeI restriction site (underlined) was inserted into the primer set forth in SEQ ID NO: 22 to clone the tRNA gene into an RIL-Nde codon plasmid.

(tRNA RLF):
SEQ ID NO: 22
5'-GATCGTTGACAGCCGCGTGGCTTTGCTGGTGAT-3'

(tRNA LNdeR):
SEQ ID NO: 23
5'-NNNNNNN<u>CATATG</u>ACTCCGGAACGCGCCTCCAC-3'

Each of the tRNA genes tyrV, lysT, argU-ileY, thrU, argW, and leuZ of *E. coli* was amplified through a PCR method using the respective pairs of PCR primers synthesized thus, and then recovered through 0.8% agarose gel electrophoresis. The four DNA fragments, tyrV, lysT, and argU-ileY, were mixed and annealed, and the primers set forth in SEQ ID NOS: 12 and 17 were then added to amplify a gene to which a tyrV-lysT-argU-ileY tRNA gene was bound. At the same time, the three DNA fragments, thrU, argW, and leuZ, were mixed and annealed, and a tRNA gene to which a thrU-argW-leuZ tRNA gene was bound was amplified using the primers set forth in SEQ ID NOS: 18 and 23. Also, the tyrV-lysT-argU-ileY fragment and the thrU-argW-leuZ fragment were mixed and annealed, and a tyrV-lysT-argU-ileY-thrU-argW-leuZ tRNA gene was amplified using the primers set forth in SEQ ID NOS: 12 and 23. These finally constructed tRNA genes were genes assigning the codons UAU (Tyr), AAA (Lys), AGA (Arg), AUA (Ile), ACA (Thr), AGG (Arg), and UUA (Leu) used to construct the RILYKT codon plasmid.

More particularly, to amplify DNA fragment containing a tRNA gene tyrV (Note: 370 bp: positions 128640 to 1286760 in the base sequence with GenBank Accession No. U00096) assigning the codon UAU (Tyr) of *E. coli* through PCR, the primer set forth in SEQ ID NO: 12 was synthesized such that the primer included a portion of 5' base sequence of a tyrV gene, and the primer set forth in SEQ ID NO: 13 was synthesized in a 5'→3' direction such that the primer had a base sequence complementary to the base sequence of a 3' terminal region of the tyrV gene. In this case, the primer set forth in SEQ ID NO: 13 included a portion of a 5' base sequence of the tRNA gene lysT assigning the codon AAA (Lys) to be constructed later. Also, to clone the tyrV gene into an XhoI site of the RIL-Nde codon plasmid, the primer set forth in SEQ ID NO: 12 had an XhoI restriction site at the 5' terminal region. Subsequently, *E. coli* genomic DNA used as the template, and primers set forth in SEQ ID NOS: 12 and 13 were added to a PCR reaction solution (200 μM dNTPs, a 10×PyroAce DNA polymerase buffer, and a 2.5 U Super PyroAce DNA polymerase) to amplify the tyrV gene. The PCR reaction was performed for one cycle of denaturation at 95° C. for 3 minutes, followed by 30 cycles of denaturation at 94° C. for 30 seconds, annealing at 55° C. for 30 seconds, and extension at 72° C. for 30 seconds, and one final cycle of extension at 72° C. for 5 minutes. The PCR reaction products were electrophoresed in 0.8% agarose gel to determine the presence of a DNA fragment containing tyrV gene having a molecular weight of 370 bp. The reaction mixture obtained through PCR was electrophoresed in 0.8% agarose gel, and a DNA product with a molecular weight of approximately 370 bp amplified through PCR was purified using a MEGA-Spin™ Agarose Gel extraction kit (iNtRON Biotechnology, Inc. Korea).

The tRNA gene lysT assigning the codon AAA (Lys) was amplified in a similar manner using *E. coli* genomic DNA as a template and the primers set forth in SEQ ID NOS: 14 and 15. The lysT gene was designed in consideration of the tRNA gene upstream and downstream from the lysT gene when the tRNA genes were linked upon synthesis of the primers. Therefore, the primer set forth in SEQ ID NO: 14 was synthesized by synthesizing a 5' base sequence of the lysT gene in a 5'→3' direction. In this case, the primer set forth in SEQ ID NO: 14 was synthesized such that a portion of the 3' base sequence of the tyrV gene was included upstream from a base sequence of the lysT gene. The primer set forth in SEQ ID NO: 15 was obtained by synthesizing a base sequence complementary to a base sequence of a 3' terminal region of the lysT gene. In this case, the primer set forth in SEQ ID NO: 15 included a portion of a 5' base sequence of an argU gene to be constructed later. Subsequently, PCR was performed under the same PCR reaction conditions as described above using *E. coli* genomic DNA as the template and the primers set forth in SEQ ID NOS: 14 and 15, and the DNA product of the lysT gene having a molecular weight of approximately 400 bp was purified in the same manner as described above.

The primers used to amplify DNA fragment containing a tRNA gene argU-ileY assigning two consecutive codons AGA (Arg) and AUA (Ile) to be inserted downstream from a lysT gene fragment were synthesized in consideration of the contents as described above. The primer set forth in SEQ ID NO: 16 was obtained by synthesizing a base sequence of the argU gene including a portion of the base sequence of the lysT gene in a 5'→3' direction. The primer set forth in SEQ ID NO: 17 was obtained by synthesizing a base sequence complementary to an ileY gene, which included a portion of a base sequence of a thrU gene to be constructed later, in a 5'→3' direction. Subsequently, an argU-ileY gene having a molecular weight of approximately 437 bp was amplified through PCR using the RIL codon plasmid as a template and the primers set forth in SEQ ID NOS: 16 and 17, and recovered in the same manner as described above.

The primers used to amplify DNA fragment containing a tRNA gene thrU assigning the codon ACA (Thr) were synthesized in consideration of the contents as described above. The primer set forth in SEQ ID NO: 18 was obtained by synthesizing a base sequence of the thrU gene including a portion of the base sequence of the ileY gene in a 5'→3' direction. The primer set forth in SEQ ID NO: 19 was obtained by synthesizing a base sequence complementary to the thrU gene, which included a portion of the base sequence of the argW gene assigning the codon AGG (Arg) to be constructed later, in a 5'→3' direction. Subsequently, PCR was performed in the same manner as described above using *E. coli* genomic DNA as a template and the primers set forth in SEQ ID NOS: 18 and 19, and the PCR product of the thrU gene having a molecular weight of approximately 200 bp was purified and recovered.

The primers used to amplify DNA fragment containing the tRNA gene argW assigning the codon AGG (Arg) were synthesized in consideration of the contents as described above. The primer set forth in SEQ ID NO: 20 was obtained by synthesizing a base sequence of the argW gene including a portion of the base sequence of the thrU gene in a 5'→3' direction. The primer set forth in SEQ ID NO: 21 was obtained by synthesizing a base sequence complementary to the argW gene including a portion of the base sequence of the leuZ gene in a 5'→3' direction. Subsequently, PCR was performed in the same manner as described above using *E. coli* genomic DNA as a template and the primers set forth in SEQ ID NOS: 20 and 21, and the PCR product of the argW gene having a molecular weight of approximately 270 bp was purified and recovered.

Finally, the primers used to amplify DNA fragment containing a tRNA gene leuZ assigning the codon UUA (Leu) were synthesized in consideration of the contents as described above. The primer set forth in SEQ ID NO: 22 was obtained by synthesizing a base sequence of the leuZ gene including a portion of the base sequence of the argW gene in *E. coli* in a 5'→3' direction. The primer set forth in SEQ ID NO: 23 was obtained by synthesizing a base sequence complementary to the base sequence of the leuZ gene in a 5'→3' direction. For reference, an NdeI restriction site (underlined) was inserted into the primer set forth in SEQ ID NO: 23 for the purpose of gene cloning. Subsequently, PCR was performed in the same manner as described above using *E. coli* genomic DNA as a template and the primers set forth in SEQ ID NOS: 22 and 23, and the PCR product of the argW gene having a molecular weight of approximately 240 bp was purified and recovered.

As a result, each of the tRNA gene DNA fragments of tyrV (370 bp), lysT (400 bp), argU-ileY (437 bp: amplified from the RIL codon plasmid), thrU (200 bp), argW (270 bp), and leuZ (240 bp) was amplified through a PCR method using the primers prepared thus, purified, and recovered. The recovered tyrV, lysT and argU-ileY DNA fragments were mixed in a ratio of 1:1:1, annealed, and then subjected to PCR in the same manner as described above using the primers set forth in SEQ ID NOS: 12 and 17 to amplify a tyrV-lysT-argU-ileY DNA fragment having a molecular weight of 1,207 bp. At the same time, the thrU, argW and leuZ DNA fragments were mixed in a ratio of 1:1:1, annealed, and then subjected to PCR using the primers set forth in SEQ ID NOS: 18 and 23 to amplify a thrU-argW-leuZ DNA fragment having a molecular weight of 700 bp. Thereafter, the tyrV-lysT-argU-ileY DNA fragment and the thrU-argW-leuZ DNA fragment were mixed with each other, annealed, and then subjected to PCR using the primers set forth in SEQ ID NOS: 12 and 23 to amplify a tyrV-lysT-argU-ileY-thrU-argW-leuZ gene having a molecular weight of 1,907 bp.

The amplified gene was electrophoresed in agarose gel, and purified using the agarose gel extraction kit. The purified tRNA gene fragment was digested with the restriction enzymes XhoI and NdeI, cloned into an RIL-Nde codon plasmid digested with the same restriction enzymes, and then ligated using a T4 DNA ligase. Then, *E. coli* W3110 was transformed with the resulting RIL-Nde codon plasmid. Plasmid DNA was separated from the transformants using an alkaline lysis method, digested with the restriction enzymes XhoI and NdeI, and then electrophoresed in 0.8% agarose gel together with a DNA size marker to re-confirm that the tRNA gene was exactly cloned into the expression vector. The expression vector for expression of the tRNA gene constructed thus was designated as an RILYKT codon plasmid (SEQ ID NO: 24), and the recombinant strain transformed with the RILYKT codon plasmid was designated as *E. coli* W3110-RILYKT.

Referring to FIG. 3B, each of *E. coli* W3110, *E. coli* W3110-RIL, and *E. coli* W3110-RILYKT was transformed with the pETRPNEQHS plasmid constructed according to the method of Example 1, and expression levels of the pETRPNEQHS plasmid in the *E. coli* strains were compared. As a result, it was revealed that the expression rate of the Neq HS DNA polymerase was slightly increased by approximately 8% in the *E. coli* W3110-RIL, compared to that of the *E. coli* W3110, but that the expression rate of the Neq HS DNA polymerase was highly increased by approximately 55% in the *E. coli* W3110-RILYKT, compared to that of the *E. coli* W3110 (FIG. 3B).

Example 3

Preparation of Mutant Neq HS DNA Polymerase Genes

Point mutations in the Neq HS DNA polymerase gene (SEQ ID NO: 5) were induced using a QuikChange site-directed mutagenesis method (see the Stratagene manual for QuikChange® Site-Directed Mutagenesis Kits). Alanine (Ala), asparagine (Asn), and serine (Ser) arranged at $523^{rd}$, $540^{th}$ and $185^{th}$ positions in the Neq DNA polymerase, respectively, were chosen as target residues to be mutated. The primers used to obtain the mutant Neq HS polymerase genes from the Neq HS DNA polymerase gene are listed in the following Table 2.

First, A523R, in which nucleic acids corresponding to the alanine (Ala) at the $523^{rd}$ position were replaced with those corresponding to the arginine (Arg), was prepared using the Neq HS DNA polymerase gene as a template. In this case, the A523R was selected since a mutant Neq A523R of the Neq DNA polymerase from which the intein was already removed had better PCR and amplification rates than the wild-type Neq DNA polymerase (see Korean Patent No. 10-1105271). PCR for constructing an Neq HS A523R DNA polymerase gene was performed in a reaction mixture including 0.05 µg of the pETRPNEQHS plasmid as the template, 20 pmol of each of a 5' terminal primer A523RF (SEQ ID NO: 25) and a 3' terminal primer A523RR (SEQ ID NO: 26) (see Table 2), 200 µM dNTPs, a 10×PyroAce DNA polymerase buffer and a 2.5 U Super PyroAce DNA polymerase for one cycle of denaturation at 95° C. for 3 minutes, followed by 12 cycles of denaturation at 94° C. for 30 seconds, annealing at 55° C. for 60 seconds, and extension at 68° C. for 7 minutes, and one final cycle of extension at 68° C. for 10 minutes. The resulting PCR products were treated at 37° C. for an hour with a restriction enzyme DpnI specifically digesting only methylated DNA to remove the original template DNA. *E. coli* DH5a (Stratagene, USA) was then transformed with the undigested PCR-amplified DNA mutants (the PCR products were not methylated). Plasmid DNA was separated from the transformants using an alkaline lysis method, the PCR-amplified DNA mutants were sequenced to determine whether the alanine (Ala) at position 523 was replaced with the arginine (Arg) (A523R: SEQ ID NO: 31). The Neq HS A523R DNA polymerase in which the alanine (Ala) at position 523 of the Neq HS DNA polymerase gene was replaced with arginine (Arg) (A523R) was simply designated as Neq HS M DNA polymerase. An amino acid sequence of the Neq HS M DNA polymerase was determined based on the base sequence of the Neq HS M1 DNA polymerase gene (SEQ ID NO: 32). The expression vector containing the Neq HS M DNA polymerase gene was designated as pETRPNEQHSM1.

Second, a double-mutant Neq HS A523R/N540R DNA polymerase in which asparagine (Asn) at a 540$^{th}$ position was replaced with arginine (Arg) was prepared using the Neq HS A523R DNA polymerase (i.e., Neq HS M DNA polymerase) gene as a template. In the case of the composition of the PCR reaction solution and the PCR method, the PCR reaction solution had the same composition as described above, except that 0.05 μg of the pETRPNEQHSM1 was used as the template plasmid and 20 pmol of each of a 5' terminal primer N540RF (SEQ ID NO: 27) and a 3' terminal primer N540RR (SEQ ID NO: 28) were used (see Table 2), and the PCR method was performed in the same manner as described above. Thereafter, the resulting PCR products were treated with DpnI, and E. coli DH5a was transformed with the mutant plasmids. The PCR products were sequenced to screen the transformants in which the asparagine (Asn) at position 540 was doubly replaced with the arginine (Arg) (N540R: SEQ ID NO: 33). The Neq HS A523R/N540 DNA polymerase in which the asparagine (Asn) at position 540 of the Neq HS DNA polymerase gene was replaced with the arginine (Arg) (N540R) was simply designated as Neq HS M2 DNA polymerase. An amino acid sequence of the Neq HS M2 DNA polymerase (i.e., Neq HS DNA polymerase including A523R/N540R double substitutions) was determined based on the base sequence of the Neq HS M2 DNA polymerase gene (SEQ ID NO: 34). The expression vector containing the Neq HS M2 DNA polymerase gene was designated as pETR-PNEQHSM2.

Third, a triple-mutant Neq HS A523R/N540R/S185D DNA polymerase in which serine (Ser) at a 185$^{th}$ position was replaced with aspartic acid (Asp) was prepared using the Neq HS A523R/N540R DNA polymerase (i.e., a Neq HS M2 DNA polymerase) gene as a template. In the case of the composition of the PCR reaction solution and the PCR method, the PCR reaction solution had the same composition as described above, except that 0.05 μg of the pETRP-NEQHSM2 was used as the template plasmid and 20 pmol of each of a 5' terminal primer S185DF (SEQ ID NO: 29) and a 3' terminal primer S185DR (SEQ ID NO: 30) were used (see Table 2), and the PCR method was performed in the same manner as described above. Thereafter, the resulting PCR products were treated with DpnI, and E. coli DH5a was transformed with the mutant plasmids. The PCR products were sequenced to screen the transformants in which the serine (Ser) at position 185 was replaced with the aspartic acid (Asp) (S185D: SEQ ID NO: 35). The Neq HS DNA polymerase including A523R/N540R/S185D triple substitutions was simply designated as Neq HS M3 DNA polymerase. Also, an amino acid sequence of the Neq HS M3 DNA polymerase was determined based on the base sequence of the Neq HS M3 DNA polymerase gene (SEQ ID NO: 36). The expression vector containing the Neq HS M3 DNA polymerase gene was designated as pETRPNEQHSM3.

Also, the target proteins expressed from the E. coli W3110-RILYKT/pETRPNEQHS, the E. coli W3110-RILYKT/pETRPNEQHSM1, the E. coli W3110-RILYKT/pETRP-NEQHSM2 and the E. coli W3110-RILYKT/pETRPNEQHSM3 were equally designated as a Neq HS DNA polymerase, a Neq HS M1 DNA polymerase, a Neq HS M2 DNA polymerase and a Neq HS M3 DNA polymerase, respectively.

Among these, the E. coli strain carrying the expression vector pETRPNEQHS were deposited in the Korean Culture Center of Microorganisms (KCCM; 361-221, Hongje 1-dong, Seodaemun-gu, Seoul) under the deposition name E. coli W3110-RILYKT/pETRPNEQHS (Accession No.: KCCM1448P) on Aug. 29, 2013. Also, the E. coli strain carrying the expression vector pETRPNEQHSM3 were deposited in the KCCM under the deposition name E. coli W3110-RILYKT/pETRPNEQHSM3 (Accession No.: KCCM1449P).

TABLE 2

Sequences of primers used to prepare mutants in the present disclosure

| Amino acid substitution | Primer name | Base sequences of mutant primers |
|---|---|---|
| A523R (Ala → Arg) | A523RF | 5'-ATAAATGCTAAGCAA<u>AGA</u>GTATTGAAAATAATA-3' (SEQ ID NO: 25) |
| | A523RR | 5'-TATTATTTTCAATAC<u>TCT</u>TTGCTTAGCATTTAT-3' (SEQ ID NO: 26) |
| N540R (Asn → Arg) | N540RF | 5'-TATATGGGTTTCCC<u>AAGA</u>GCGAGATGGGATTGC-3' (SEQ ID NO: 27) |
| | N540RR | 5'-GCAATCCCATCTCGC<u>TCT</u>TGGGAAACCCATATA-3' (SEQ ID NO: 28) |
| S185D (Ser → Asp) | S185DF | 5'-GATATAGAAGTTTAC<u>GAT</u>GAGGCTTTCCCTAAT-3' (SEQ ID NO: 29) |
| | S185DR | 5'-ATTAGGGAAAGCCT<u>CATCG</u>TAAACTTCTATATC-3' (SEQ ID NO: 30) |

Example 4

The Expression and Purification of Recombinant Neq HS DNA Polymerase and Mutant Neq HS DNA Polymerases The Neq HS DNA polymerase and the mutant DNA polymerases M1, M2 and M3 were expressed from the recombinant strains, E. coli W3110-RILYKT/pETRPNEQHS, E. coli W3110-RILYKT/pETRPNEQHSM1, E. coli W3110-RILYKT/pETRPNEQHSM2 and E. coli W3110-RILYKT/pETRPNEQHSM3, in which the E. coli W3110-RILYKT host prepared by the method of Example 2 was transformed with the plasmids constructed in each of Examples 1 and 3. Thereafter, the 4 kinds of Neq HS DNA polymerases were purified from the expressed proteins at a low temperature to prevent splicing of the intein.

The E. coli W3110-RILYKT strain carrying each recombinant plasmid prepared in Example 1 was seeded in an LB liquid medium supplemented with ampicillin and chloramphenicol at final concentrations of 100 μg/ml and 34 μg/ml, respectively, and cultured overnight at 37° C. Thereafter, 5 ml of a culture broth was taken, and seeded in 500 ml of an M9 defined medium (including 0.1% glucose and 0.5% casamino acid) supplemented with ampicillin and chloramphenicol at final concentrations of 100 μg/ml and 34 μg/ml, respectively, and cultured at 37° C. for 20 hours. The resulting culture broth was centrifuged at 6,000 rpm for 20 minutes to recover a pellet of the strain (3.0 g/wet weight). Then, the pellet was suspended in 20 ml of buffer A (20 mM Tris-HCl (pH 7.4), 0.3

M NaCl) including 1 mM phenylmethanesulfonylfluoride (PMSF), homogenized by sonication, and then centrifuged at 15,000 rpm for 30 minutes to remove the *E. coli* cell debris. The resulting supernatant was attached to a HisTrap™ HP column (GE Healthcare) equilibrated with buffer A, and then washed thoroughly with the same buffer A. The proteins attached to the column were eluted with the same buffer with a 0 to 0.5 M imidazole gradient. The peak fractions expected to contain the DNA polymerase were selected, and sufficiently dialyzed in buffer B (20 mM Tris-HCl (pH 8.8), 0.1 M NaCl, 1 mM dithiothreitol (DTT)). For reference, the DNA polymerases might precipitate when the 1 mM DTT was not present in the buffer B. The sufficiently dialyzed sample was allowed to flow through an anion-exchange column, HiTrap™ Q column (GE Healthcare), which was equilibrated with the buffer B. In this case, the DNA polymerases themselves passed through the column without being attached to the column, and a small quantity of *E. coli*-derived proteins which were attached to the HisTrap™ HP column and eluted together were removed since the *E. coli*-derived proteins were attached to the HiTrap™ Q column. The samples of DNA polymerases eluted without attaching to the HiTrap™ Q column were collected, adjusted to pH 7.0 using a 0.2 N HCl solution, and immediately attached to a cation-exchange column, HiTrap™ SP column (GE Healthcare), which was equilibrated with buffer C (20 mM Tris-HCl (pH 7.0), 0.1 M NaCl). The column was thoroughly washed with buffer C, and the DNA polymerases attached to the column were then eluted with the same buffer with a 0.1 to 1 M NaCl gradient. The DNA polymerases finally purified through the above-described method were dialyzed in a storage buffer (20 mM Tris-HCl (pH 7.4), 0.1 mM EDTA, 0.1% Tween 20, 0.1% Nonidet P40, 50 mM KCl, 1 mM DTT, 50% Glycerol), and stored at −20° C. The dialyzed DNA polymerases were used whenever PCR were performed. The purified proteins were quantified using a Bradford assay. For reference, the purification results obtained in the respective purification steps of purifying the DNA polymerases from the *E. coli* W3110-RILYKT strain carrying the recombinant plasmid pETRP-NEQHS are listed in the following Table 3. The specific activities of the purified Neq HS DNA polymerases were 2.27 U/mg.

TABLE 3

Purification of Neq HS DNA polymerases derived from *E. coli* W3110-RILYKT/pETRPNEQHS

| | Total protein (mg) | Total activity (U) | Specific activity (U/mg) | Recovery (%) |
|---|---|---|---|---|
| Crude extract | 265.3 | 69.7 | 0.26 | 100.0 |
| HisTrap ™ HP | 38.8 | 41.8 | 1.08 | 59.9 |
| HiTrap ™ Q HP | 3.6 | 8.0 | 2.21 | 11.5 |
| HiTrap ™ SP HP | 2.0 | 4.6 | 2.27 | 6.6 |

The Neq HS mutant DNA polymerases were purified in the same manner as described above. The specific activities of the Neq HS M DNA polymerase, the Neq HS M2 DNA polymerase and the Neq HS M3 DNA polymerase were 2.33 U/mg, 2.32 U/mg, and 2.55 U/mg, respectively.

In this case, one unit (U) was defined as an amount of DNA polymerase required to insert 10 nmol dNTP at 75° C. for 30 minutes in an acid-insoluble form.

The amount of the protein in each purification step was determined using a Bradford assay. Also, denaturing gel electrophoresis (i.e., sodium dodecyl sulfate-polyacrylamide gel electrophoresis, SDS-PAGE) was performed to determine a degree of purification of the Neq HS DNA polymerase according to the purification steps, and degrees of purification of the mutant Neq HS DNA polymerases purified through the same purification procedures (see FIG. 4). FIG. 4A shows the results of some steps of purifying a Neq HS DNA polymerase derived from pETRPNEQHS. Here, Lane 1 represents a sonicated sample of an *E. coli* W3110-RILYKT/pETRPNEQHS strain cultured in an LB medium, Lane 2 represents a sonicated sample of the *E. coli* W3110-RILYKT/pETRPNEQHS strain cultured in an M9 defined medium supplemented with 0.1% glucose and 0.5% casamino acid, Lane 3 represents a sample after HisTrap™ HP column chromatography, Lane 4 represents a sample after HiTrap™ Q HP column chromatography, and Lane 5 represents a sample after HiTrap™ SP HP column chromatography. The Neq HS DNA polymerase gene was more effectively expressed under the control of the trp promoter in an M9 defined medium (including 0.1% glucose and 0.5% casamino acid) which was completely deficient in tryptophan than in an LB medium containing a small amount of tryptophan. The Neq HS DNA polymerase gene was proven to have a molecular weight of approximately 110 kDa which was similar to the molecular weight (Mw: 110,306.24 Da) calculated from the DNA sequence of the Neq HS DNA polymerase observed through SDS-PAGE. FIG. 4B shows the results obtained by finally purifying the mutant DNA polymerases in the same manner as in the method of purifying the pETRPNEQHS-derived Neq HS DNA polymerase and analyzing the mutant DNA polymerases through SDS-PAGE. Here, Lane 1 represents a Neq HS DNA polymerase, Lane 2 represents a Neq HS M DNA polymerase, Lane 3 represents a Neq HS M2 DNA polymerase, and Lane 4 represents a Neq HS M3 DNA polymerase. It was revealed that these mutant DNA polymerases had a substantially similar molecular weight of approximately 110 kDa. Lane M represents a low molecular weight protein marker.

Example 5

Figure 5A:
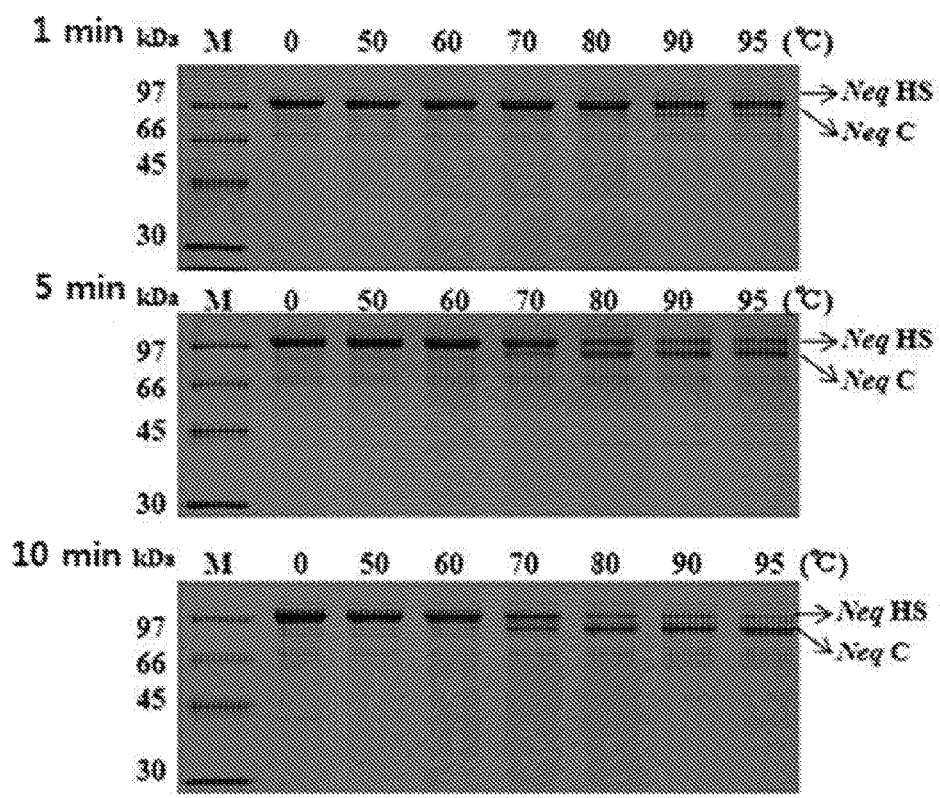
FIG. 5A shows the results obtained by comparatively analyzing an effect on a protein splicing reaction according to a reaction temperature and a reaction time when the Neq HS DNA polymerase is added at a concentration of 30 pmol. These comparative analyses are performed through SDS-denatured gel electrophoresis after the Neq HS DNA polymerase is allowed to react at a reaction temperature of 50 to 95° C. for 1, 5, and 10 minutes.

Comparison of Protein-Splicing Effects of Neq HS DNA Polymerase According to Temperature and Reaction Time To examine an effect of a high temperature on protein splicing, the purified Neq HS DNA polymerase prepared in Example 4 was added to a protein splicing reaction solution (20 mM Tris-HCl (pH 8.0), 50 mM NaCl) at a concentration of 30 pmol, reacted at temperature of 50 to 95° C. for 1, 5 and 10 minutes, and analyzed through SDS-PAGE. The results are shown in FIG. 5A. It was revealed that the amount of a protein-spliced product, Neq C (a Neq DNA polymerase having a molecular weight of approximately 94 kDa), was increased while the amount of the purified Neq HS DNA polymerase (having a molecular weight of approximately 110 kDa) was decreased. Also, it could be seen that the protein splicing occurred at a temperature of 70° C. or higher, and that the protein splicing reached the maximum at 95° C. Also, it could be seen that the protein splicing increasingly occurred with the passage of a reaction time. FIG. 5A shows the results obtained by analyzing a protein splicing effect of the purified Neq HS DNA polymerase according to a reaction temperature and a reaction time. In FIG. 5A, Lane M represents a low molecular weight protein marker loaded in gel.

Figure 5B:
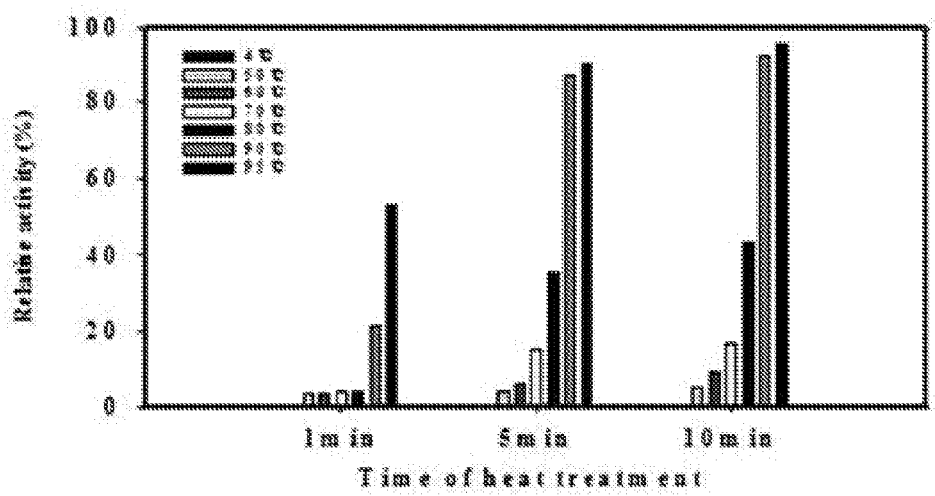
FIG. 5B shows the results obtained by measuring the activities of the Neq HS DNA polymerase in a reaction solution for splicing a Neq HS DNA polymerase protein according to the temperature and the reaction time.

FIG. 5B shows the results obtained by measuring the activities of the Neq HS DNA polymerase in a reaction solution for protein splicing the Neq HS DNA polymerase according to the temperature and the reaction time. The activities of the Neq HS DNA polymerase were measured as follows (see Choi, J. J. et al., 2006, *J. Mol. Biol.* 356, 1093-1106). A reaction mixture (50 µl) including the purified protein, 1 µg of activated calf *thymus* DNA, 20 mM Tris-HCl (pH 8.0), 1.5 mM MgCl$_2$, 50 mM KCl, 100 µM dATP, 100 µM dCTP, 100 µM dGTP, 10 µM dTTP and 0.25 µCi [methyl-$^3$H] TTP was reacted at 75° C. for 10 minutes, quenched on ice, and then dripped on a DE81 filter paper disc (23 mm, Whatman Co., UK). The DE81 filter paper disc on which the reaction solution was dripped was dried at 65° C., and sequentially washed with a 0.5 M sodium phosphate (pH 7.0) buffer for 10 minutes and 70% ethanol for 5 minutes, and dried again at 65° C. The incorporated radioactivity of the DE81 filter paper disc prepared thus was measured using an LS6500 scintillation counter (Beckman Co., UK) to determine the activities of the DNA polymerases. In this case, the activity of Neq P (a DNA polymerase obtained by recombining an extein-coding region of a Neq L fragment gene with an extein-coding region of a Neq S fragment gene, except the intein-coding region, and expressing the extein-coding regions of the Neq L and Neq S fragment genes in the form of one polypeptide) when present at concentration of 30 pmol was set to 100%. The activities of the DNA polymerases in a protein splicing reaction solution of Neq HS DNA polymerase were measured. The measurement results are shown in FIG. 5B. Accordingly, it could be seen that the activities of the DNA polymerases in the protein splicing reaction solution of Neq HS DNA polymerase according to the reaction temperature and time was at a very low level of 70° C. or less, but reached a maximum of 95° C. (FIG. 5B). Such results coincided well with the results analyzed through the denaturing gel electrophoresis shown in FIG. 5A.

Example 6

Examination of Protein-Splicing Effect of Neq HS DNA Polymerase According to the Number of PCR Reaction Cycles To examine a protein-splicing effect under general PCR conditions using a PCR machine, each of the purified Neq HS DNA polymerases prepared in Example 4 was added at a concentration of 30 pmol to a protein splicing reaction solution (20 mM Tris-HCl (pH 8.0), 50 mM NaCl), and a PCR reaction was performed for 0, 1, 2, 3, 4, 5, 10, 20 and 30 cycles, and the resulting PCR products were analyzed through denaturing gel electrophoresis. In this case, the PCR reaction conditions included one cycle of denaturation at 94° C. for 20 seconds, annealing at 63° C. for 20 seconds and extension at 72° C. for 20 seconds, and a pre-denaturing procedure was performed for one cycle of 95° C. for 0 minutes, 95° C. for 1 minute, and 95° C. for 3 minutes prior to the PCR cycles.

Figure 6A:
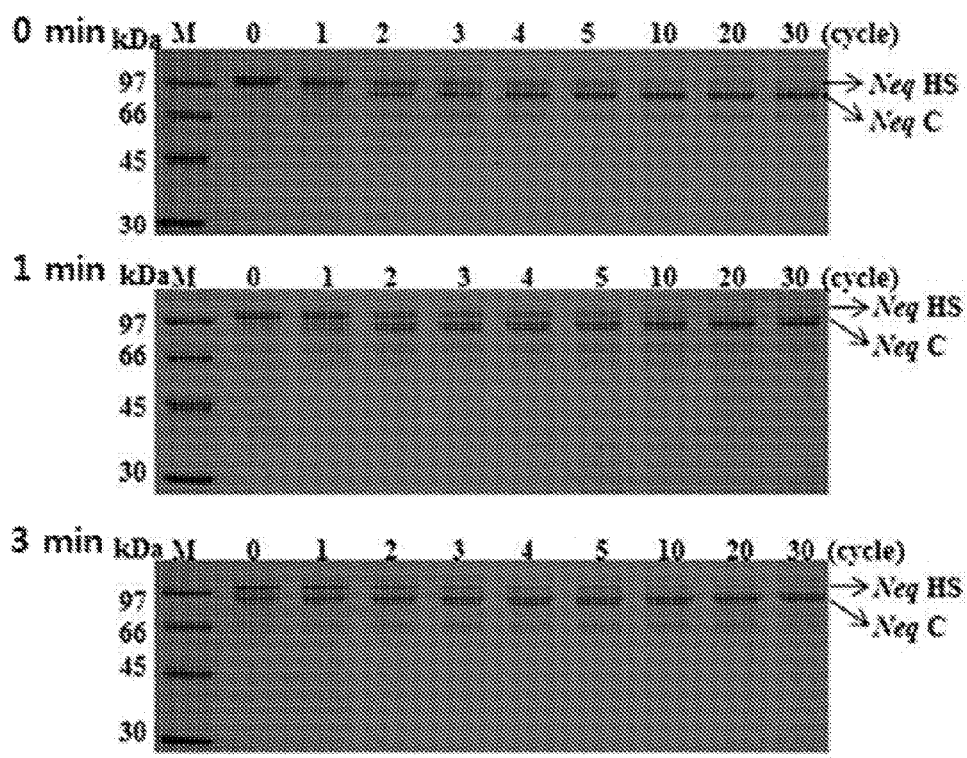
FIG. 6A shows the results obtained by determining a protein-splicing effect of the Neq HS DNA polymerase according to a pre-denaturing procedure and the number of PCR reaction cycles using SDS-denatured gel electrophoresis. The pre-denaturing procedure is performed at 95° C. for 0 minutes, 1 minute, and 3 minutes, and the PCR reaction is performed for 1, 2, 3 4, 5, 10, 20, and 30 cycles.
Figure 6B:
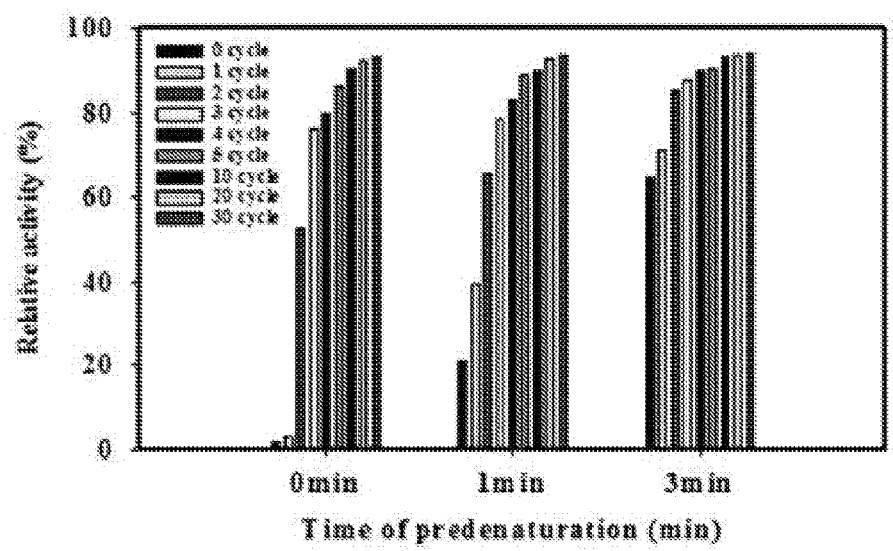
FIG. 6B shows the results obtained by measuring the activities of the Neq HS DNA polymerase in a reaction solution for splicing a Neq HS DNA polymerase protein according to the number of PCR reaction cycles shown in FIG. 5A.

As a result, it could be seen that the amount of the protein-spliced product, Neq C (a Neq DNA polymerase having a molecular weight of approximately 94 kDa), was increased while the amount of the purified Neq HS DNA polymerase (approximately 110 kDa) was decreased, indicating that the protein splicing readily occurred with an increase in the number of PCR cycles (see FIG. 6A). Also, the protein splicing was easily affected by the pre-denaturing time in the early stage of the PCR cycles, but was not affected by the pre-denaturing time with the increasing number of the PCR cycles, and thus the protein splicing occurred readily (see FIG. 6A). FIG. 6B shows the results obtained by measuring the activities of the DNA polymerase according to the number of PCR reaction cycles as described above in Example 5. In this case, the activity of Neq P when present at a concentration of 30 pmol was set to 100%, and the activities of the HS DNA polymerase in a protein splicing reaction solution of Neq HS DNA polymerase were measured. The measurement results were similar to those of FIG. 6A (see FIG. 6B). It could be seen that smearing occurred when a large amount of the Neq C was produced at the early stage, but that the smearing was prevented in the case of the Neq HS DNA polymerase since the intein-removed activated Neq C was produced.

Example 7

Determination of Optimal PCR Conditions for Neq HS DNA Polymerase and Mutant Neq HS DNA Polymerases To apply Neq HS DNA polymerase, Neq HS M polymerase, Neq HS M2 polymerase and Neq HS M3 DNA polymerase to PCR, the compositions of an optimal PCR reaction solution should be determined. First, a basic PCR reaction mixture was set as follows, and optimized while slightly adjusting a pH value or a concentration of each component. That is, the basic reaction mixture (50 µl) contained 40 mM Tricine-KOH (pH 8.0), 50 ng of human genomic DNA as a template, 20 pmol of each of a β-globin-derived 5' terminal primer (MP_β_globin_F: 5'-TCCCTCTCAACCCTACAGT-CACCCATTTGG-3') (SEQ ID NO: 42) and a 3' terminal primer (MP_β_globin_R: 5'-CAGTCATGGACAATAAC-CCTCCTCCCAGGT-3') (SEQ ID NO: 43), 200 µM dNTPs, the purified Neq HS DNA polymerase, 1 mM MgCl$_2$, 80 mM KCl, 0.15% BSA and 1 mM DTT. For reference, the enzymes were added at different quantities according to the characteristics of the enzymes, that is, the Neq HS DNA polymerase and the Neq HS M DNA polymerase were added at a concentration of 50 ng to 50 µl of the PCR reaction mixture, and the Neq HS M2 DNA polymerase and the Neq HS M3 DNA polymerase were added at concentrations of 40 ng and 90 ng, respectively. The reaction mixture was reacted for one cycle of denaturation at 95° C. for 3 minutes, followed by 30 cycles of denaturation at 95° C. for 30 seconds, annealing at 65° C. for 30 seconds, and extension at 72° C. for 60 seconds. Thereafter, the PCR results were confirmed through 0.8% agarose gel electrophoresis.

Figure 7A:
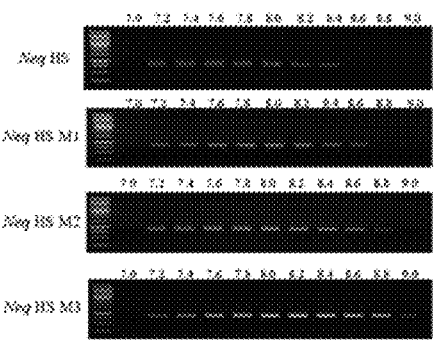
FIGS. 7A to 7C show the PCR results of the Neq HS DNA polymerase, the Neq HS M DNA polymerase, the Neq HS M2 DNA polymerase, and the Neq HS M3 DNA polymerase obtained according to the pH (FIG. 7A), the concentration of $MgCl_2$ (FIG. 7B) and the concentration of KCl (FIG. 7C) in PCR performed in the presence of dNTP.

The effects of pH on the Neq HS DNA polymerase and mutants thereof in PCR were examined. As a result, it was revealed that the optimal pH value of the PCR reaction buffer was pH 7.6 for the Neq HS DNA polymerase, was similar as pH 7.8 for the Neq HS M1 and Neq HS M2 DNA polymerases, and was somewhat different as pH 8.6 for the Neq HS M3 DNA polymerase (see FIG. 7A). In FIG. 7A, M represents a GeneRuler™ 1 kb DNA ladder (Fermentas), and each lane represents a pH value. The PCR amplification size was 850 bp.

Figure 7B:
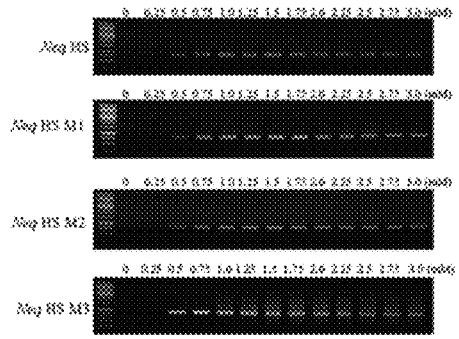

The effects of divalent cation Mg$^{2+}$ on the Neq HS DNA polymerase and mutants thereof in PCR were examined. As a result, it was revealed that the optimal concentration of the divalent cation was 1.0 mM for the Neq HS DNA polymerase, 1.25 mM for the Neq HS M DNA polymerase, 1.5 mM for the Neq HS M2 DNA polymerase, and was somewhat low as 0.75 mM for the Neq HS M3 DNA polymerase (FIG. 7B). Each lane represents a MgCl$_2$ concentration.

Figure 7C:
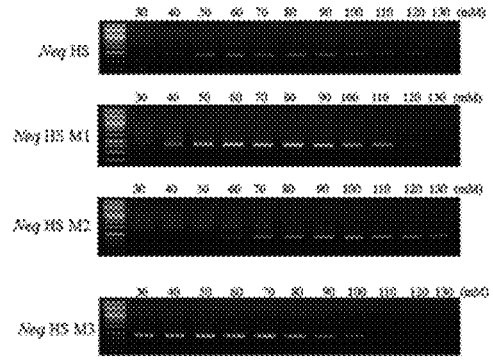

The effects of KCl on the Neq HS DNA polymerase, and the Neq HS M1, Neq HS M2 and mutant Neq HS M3 DNA polymerases in PCR were examined. As a result, it was revealed that the optimal concentration of KCl was somewhat different as 80, 70, 90 and 80 mM for the Neq HS DNA polymerase, and the Neq HS M1, Neq HS M2 and mutant Neq HS M3 DNA polymerases, respectively (see FIG. 7C). Each lane represents a KCl concentration.

From these facts, it could be seen that all of the Neq HS DNA polymerase and the Neq HS M1, Neq HS M2 and Neq HS M3 DNA polymerases were able to be used in PCR. Accordingly, the optimal PCR buffer compositions of the Neq HS DNA polymerase and mutants thereof were set to include stabilizing agents, 0.015% BSA and 1 mM DTT. For PCR using the Neq HS DNA polymerase, the optimal PCR buffer composition was set to include 40 mM Tricine-HCl (pH 7.6), 80 mM KCl, 1 mM $MgCl_2$, 0.015% BSA, and 1 mM DTT. For PCR using the Neq HS DNA M DNA polymerase, the optimal PCR buffer composition was also set to include 40 mM Tricine-HCl (pH 7.8), 70 mM KCl, 1.25 mM $MgCl_2$, 0.015% BSA, and 1 mM DTT. For PCR using the Neq HS M2 DNA polymerase, the optimal PCR buffer composition was set to include 40 mM Tricine-HCl (pH 7.8), 90 mM KCl, 1.5 mM $MgCl_2$, 0.015% BSA, and 1 mM DTT. For PCR using the Neq HS M3 DNA polymerase, the optimal PCR buffer composition was set to include 40 mM Tricine-HCl (pH 8.6), 80 mM KCl, 0.75 mM $MgCl_2$, 0.015% BSA, and 1 mM DTT.

Example 8

Analysis of PCR Efficiency of DNA Polymerases

First, to verify the DNA amplification fidelity and efficiency of the Neq HS DNA polymerase and mutant Neq HS DNA polymerases (M1, M2, and M3), PCR was performed using the human genome as a template DNA to target a 194 bp fragment of a hemoglobin gene, an 850 bp fragment of a 3-globin gene, and 2.7 kb and 6.25 kb fragments of a hypoxanthine-guanine phosphoribosyltransferase gene.

Figure 8A:
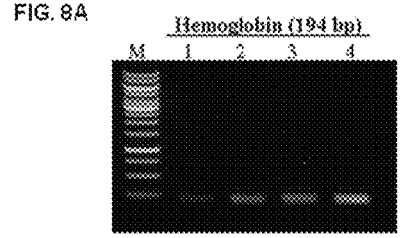
FIGS. 8A to 8D show the results obtained by performing PCR on a hemoglobin gene (FIG. 8A, a target molecular weight of 194 bp), a β-globin gene (FIG. 8B, a target molecular weight of 850 bp), a hypoxanthine-guanine phosphoribosyltransferase gene (FIG. 8C, a target molecular weight of 2.7 kb) and a hypoxanthine-guanine phosphoribosyltransferase gene (FIG. 8D, a target molecular weight of 6.25 kb) as PCR targets in the presence of dNTP using the Neq HS DNA polymerase (Lane 1), the Neq HS M DNA polymerase (Lane 2), the Neq HS M2 DNA polymerase (Lane 3), and the Neq HS M3 DNA polymerase (Lane 4), respectively.

First, a PCR reaction mixture (50 µl) used to amplify the 194 bp fragment of the hemoglobin gene in the human genome was composed, as follows. A 50 ul PCR reaction mixture contained 10 pmol of each of a forward primer (Hgb194_F: 5'-ACATTTGCTCTGACACAACTG-3') (SEQ ID NO: 44) and a reverse primer (Hgb194_R: 5'-TCCACAT-GCCCAGTTTCTATT-3') (SEQ ID NO: 45) for targeting the 194 bp fragment of the hemoglobin gene, 50 ng of human genomic DNA, 250 µM dNTPs, the DNA polymerase, and the optimal PCR buffer for each DNA polymerase whose composition was set as described above. For reference, the DNA polymerase were added at different quantities according to the characteristics of the enzymes, that is, the Neq HS DNA polymerase and the Neq HS M1 DNA polymerase were added at a concentration of 50 ng to 50 µl of the PCR reaction solution, and the Neq HS M2 DNA polymerase and the Neq HS M3 DNA polymerase were added at concentrations of 40 ng and 90 ng, respectively. The compositions of the optimal PCR buffer were slightly different according to the enzymes. The PCR reaction was performed for one cycle of denaturation at 95° C. for 3 minutes, followed by 30 cycles of denaturation at 95° C. for 30 seconds, annealing at 60° C. for 30 seconds, and extension at 72° C. for 30 seconds. Thereafter, the resulting PCR products were finally subjected to agarose gel electrophoresis in order to determine the length of the PCR products (FIG. 8A). Lane 1 represents the Neq HS DNA polymerase, Lane 2 represents the Neq HS M DNA polymerase, Lane 3 represents the Neq HS M2 DNA polymerase, and Lane 4 represents the Neq HS M3 DNA polymerase. Lane M represents the GeneRuler™1 kb DNA ladder (Fermentas). In this case, it was revealed that the Neq HS M3 DNA polymerase had a higher amplification level of target DNA than the other DNA polymerases.

Figure 8B:
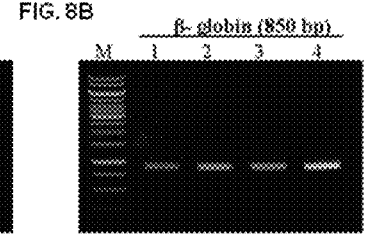

Next, the 850 bp fragment of the β-globin gene in the human genome was selected as another PCR-amplified target, and the PCR efficiencies of the Neq HS DNA polymerase and the mutants thereof were compared. 10 pmol of each of a forward primer (5'-TCCCTCTCAACCCTACAGTCAC-CCATTTGG-3') (SEQ ID NO: 42) and a reverse primer (5'-CAGTCATGGACAATAACCCTCCTCCCAGGT-3') (SEQ ID NO: 43) for targeting the 850 bp fragment of the β-globin gene was used. The primers added to the PCR reaction mixture were different, and the PCR reaction mixture and PCR conditions were identical to those used in the method. The resulting PCR products were finally subjected to electrophoresis in order to determine the length of the PCR products (FIG. 8B). In this case, it was also revealed that the Neq HS M3 DNA polymerase had a higher amplification level of target DNA than the other DNA polymerases.

Figure 8C:
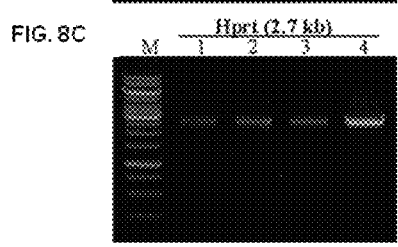
Figure 8D:
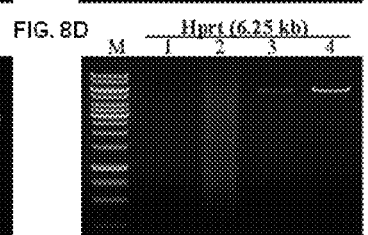

Finally, the 2.7 kb and 6.25 kb fragments of the hypoxanthine-guanine phosphoribosyltransferase gene in the human genome were selected as still another PCR-amplified target. First, a forward primer (HGPRT_F1: 5'-TGGGATIA-CACGTGTAACCAACC-3') (SEQ ID NO: 44) and a reverse primer (HGPRT_R: 5'-TGTGACACAGGCAGACTGTG-GATC-3') (SEQ ID NO: 45) were used to amplify the 2.7 kb target fragment, and a forward primer (HGPRT_F2: 5'-TGTGGCAGAAGCAGTGAGTAACTG-3') (SEQ ID NO: 46) and the same reverse primer as the reverse primer used to amplify the 2.7 kb target fragment were used to amplify the 6.25 kb target fragment. PCR was performed in the above-described PCR reaction mixture using the pair of primers. The PCR reaction for amplifying the 2.7 kb target fragment was repeatedly performed for one cycle of denaturation at 95° C. for 3 minutes, followed by 30 cycles of denaturation at 95° C. for 30 seconds, annealing at 65° C. for 30 seconds, and extension at 72° C. for 3 minutes. Also, the PCR reaction for amplifying the 6.25 kb target fragment was repeatedly performed for one cycle of denaturation at 95° C. for 3 minutes, followed by 30 cycles of denaturation at 95° C. for 30 seconds, annealing at 65° C. for 30 seconds, and extension at 72° C. for 6 minutes. The resulting PCR products were finally subjected to electrophoresis in order to determine the length of the PCR products (FIGS. 8C and 8D). In this case, it was also revealed that the Neq HS M3 DNA polymerase had a higher amplification level of target DNA than the other DNA polymerases. Lane 1 represents the Neq HS DNA polymerase, Lane 2 represents the Neq HS M DNA polymerase, Lane 3 represents the Neq HS M2 DNA polymerase, and Lane 4 represents the Neq HS M3 DNA polymerase. Lane M represents a GeneRuler™ 1 kb DNA ladder (Fermentas).

Figure 9:
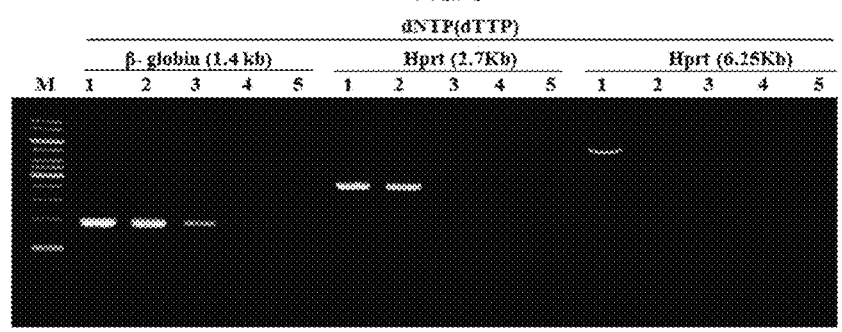
FIG. 9 shows the results obtained by performing PCR on a β-globin gene (a target molecular weight of 1.4 kb), a hypoxanthine-guanine phosphoribosyltransferase gene (a target molecular weight of 2.7 kb) and a hypoxanthine-guanine phosphoribosyltransferase gene (a target molecular weight of 6.25 kb) as PCR targets in the presence of dNTP using each of the Neq HS M3 DNA polymerase (Lane 1), the HS Taq DNA polymerase (Roche) (Lane 2), the HS Taq DNA polymerase (Takara) (Lane 3), the Taq DNA polymerase (Takara) (Lane 4), and the Pfu DNA polymerase (Promega) (Lane 5).

To verify the DNA amplification fidelity and efficiency of the Neq HS M3 DNA polymerase and commercially available DNA polymerases, PCR was also performed using the human genome as a template DNA to target a 1.4 kb fragment of a β-globin gene, and 2.7 kb and 6.25 kb fragments of a hypoxanthine-guanine phosphoribosyltransferase gene. The Neq HS M3 DNA polymerase, 1.25 U HS Taq DNA polymerase (Takara, Roche), 1.25 U Taq DNA polymerase (Takara) and 1.5 U Pfu DNA polymerase (Promega) were used as the DNA polymerases. The PCR reaction solution was composed of 10 pmol of a forward primer (3_globin_F: 5'-TCTAATCTC-CCTCTCAACCCTACAGTCACC-3') (SEQ ID NO: 47) and a reverse primer (β_globin_R: 5'-TGGAAATGATCAGGCT-TGGATTCAAAG-3') (SEQ ID NO: 48) for targeting the 1.5 kb fragment of the β-globin gene in the human genome, 50 ng of human genomic DNA, and 250 µM dNTPs, and PCR was performed in a reaction mixture obtained by adding each DNA polymerase to the optimized buffer. The PCR reaction was repeatedly performed for one cycle of denaturation at 95° C. for 3 minutes, followed by 30 cycles of denaturation at 95° C. for 30 seconds, annealing at 60° C. for 30 seconds, and extension at 72° C. for 90 seconds. Also, the primers as described above were used as primers used to amplify the 2.7 kb and 6.25 kb target fragments of the hypoxanthine-guanine phosphoribosyltransferase gene. The PCR reaction for amplifying the 2.7 kb target fragment was repeatedly performed for one cycle of denaturation at 95° C. for 3 minutes, followed by 30 cycles of denaturation at 95° C. for 30 seconds, annealing at 65° C. for 30 seconds, and extension at 72° C. for 3 minutes. Also, the PCR reaction for amplifying the 6.25 kb target fragment was repeatedly performed for one cycle of denaturation at 95° C. for 3 minutes, followed by 30 cycles of denaturation at 95° C. for 30 seconds, annealing at 65° C. for 30 seconds, and extension at 72° C. for 6 minutes. The resulting PCR products were finally subjected to electrophoresis in order to determine the length of the PCR products (FIG. 9). Lane 1 represents the Neq HS M3 DNA polymerase, Lane 2 represents the HS Taq DNA polymerase (Roche), Lane 3 represents the HS Taq DNA polymerase (Takara), Lane 4 represents the Taq DNA polymerase (Takara), and Lane 5 represents the Pfu DNA polymerase (Promega). Lane M represents a GeneRuler™ 1 kb DNA ladder (Fermentas). In this case, it was also revealed that the Neq HS M3 DNA polymerase had a higher amplification level of target DNA than the other DNA polymerases (including the HS DNA polymerases). Also, it was also revealed that the Neq HS M3 DNA polymerase had a high amplification level of long target DNA (6.25 kb) (FIG. 9).

Figure 10:
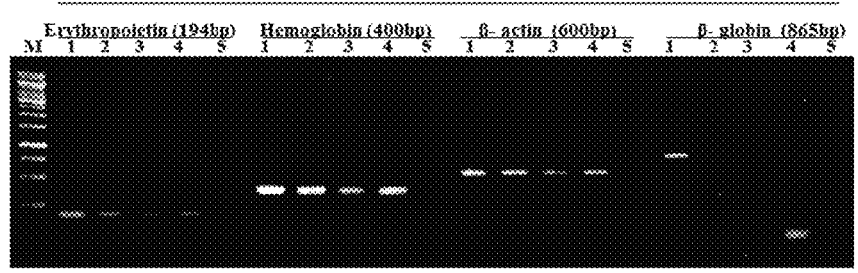
FIG. 10 shows the results obtained by performing PCR on an erythropoietin gene (a target molecular weight of 194 bp), a hemoglobin gene (a target molecular weight of 400 bp), a β-actin gene (a target molecular weight of 600 bp), and a β-globin gene (a target molecular weight of 865 bp) in the presence of dUTP rather than dTTP using each of the Neq HS M3 DNA polymerase (Lane 1), the HS Taq DNA polymerase (Roche) (Lane 2), the HS Taq DNA polymerase (Takara) (Lane 3), the Taq DNA polymerase (Takara) (Lane 4) and the Pfu DNA polymerase (Promega) (Lane 5).

As a method of preventing carry-over contamination caused in PCR, a method of performing PCR using dUTP instead of dTTP was proposed by Longo M. C. et al. (Longo M. C. et al., 1990, Gene 93:125-128). Therefore, the applicability of the Neq HS M3 DNA polymerase and the other commercially available DNA polymerases to the PCR reaction using dUTP instead of dTTP was verified. The PCR reaction was performed using the human genome as a template in the same PCR reaction solution, except that primers for targeting fragments of erythropoietin, hemoglobin, β-actin and β-globin genes, and dUTP rather than dTTP were added to the reaction solution. The sizes of the target fragments and the sequences of the primers were as follows: erythropoietin (194 bp, a forward primer Epo_F: 5'-TTGGG-GATGGCAAAAACCTGACCTGTG-3' (SEQ ID NO: 49) and a reverse primer Epo_R: 5'-GCATCCACTTCTCCGGC-CAAACTTCAAT-3' (SEQ ID NO: 50)), hemoglobin (400 bp, a forward primer Hgb400_F: 5'-TCAAACAGACAC-CATGGTGCATCTGACTCC-3' (SEQ ID NO: 51) and a reverse primer Hgb400_R: 5'-AAGGTGCCCTTGAGCT-GTCCAGGTGAG-3' (SEQ ID NO: 52)), β-actin (600 bp, a forward primer β_actin_F: 5'-TCTTGTCCTTCCTTTC-CCAGGGCGTG-3' (SEQ ID NO: 53) and a reverse primer β_actin_R: 5'-CTGGGGTCTTGGGATGGGGAGTCT-GTT-3' (SEQ ID NO: 54)), and β-globin (865 bp, a forward primer; 5'-TCCCTCTCAACCCTACAGTCAC-CCATTTGG-3' (SEQ ID NO: 42) and a reverse primer, 5'-CAGTCATGGACAATAACCCTCCTCCCAGGT-3' (SEQ ID NO: 43)). The PCR reaction was repeatedly performed for one cycle of denaturation at 95° C. for 3 minutes, followed by 30 cycles of denaturation at 95° C. for 30 seconds, annealing at 64° C. for 30 seconds, and extension at 72° C. for 60 seconds. The resulting PCR products obtained by amplifying the target fragments were confirmed through electrophoresis (FIG. 10). In this case, it was also revealed that the Neq HS DNA polymerase more specifically amplified the target DNA than the other DNA polymerases. In particular, since the Pfu DNA polymerase did not use dUTP, no target fragments were amplified. Lane 1 represents the Neq HS M3 DNA polymerase, Lane 2 represents the HS Taq DNA polymerase (Roche), Lane 3 represents the HS Taq DNA polymerase (Takara), Lane 4 represents the Taq DNA polymerase (Takara), and Lane 5 represents the Pfu DNA polymerase (Promega). Lane M represents a GeneRuler™ 1 kb DNA ladder (Fermentas).

Figure 11:
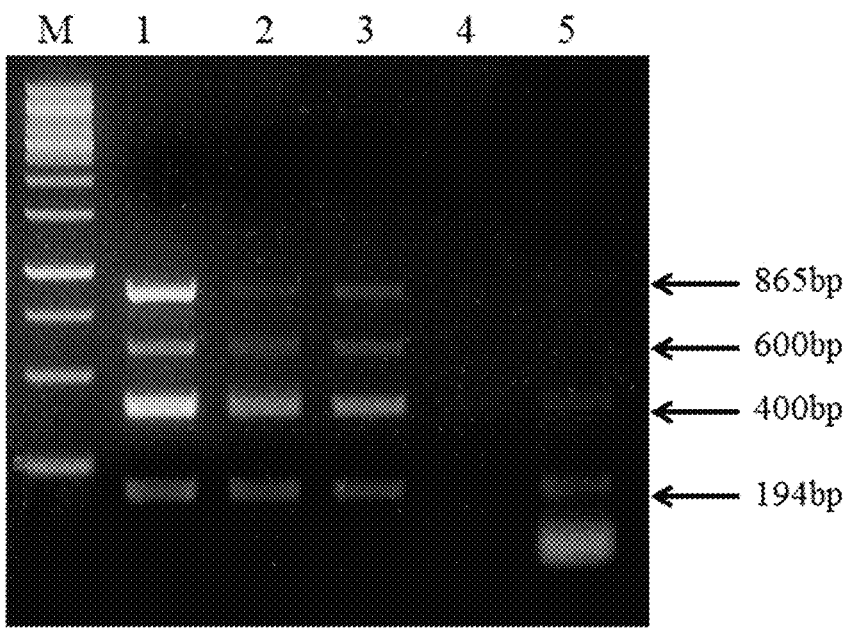
FIG. 11 shows the results obtained by adding 8 primers, which are used to amplify an erythropoietin gene (a target molecular weight of 194 bp), a hemoglobin gene (a target molecular weight of 400 bp), a β-actin gene (a target molecular weight of 600 bp), and a β-globin gene (a target molecular weight of 865 bp) in the presence of dNTP in a PCR method and performing multiplex PCR using each of the Neq HS M3 DNA polymerase (Lane 1), the HS Taq DNA polymerase (Roche) (Lane 2), the HS Taq DNA polymerase (Takara) (Lane 3), the Taq DNA polymerase (Takara) (Lane 4), and the Pfu DNA polymerase (Promega) (Lane 5).

Finally, multiplex PCR was performed to verify the DNA amplification fidelity and clinical diagnostic probability. 5 pmol of each of the primers targeting erythropoietin (194 bp), hemoglobin (400 bp), β-actin (600 bp) and β-globin (865 bp) genes in PCR was added to a reaction mixture, and each DNA polymerase, the optimal PCR buffer, 50 ng of human genomic DNA, and 250 µM dNTPs (dATP, dCTP, dGTP, dTTP) were further added to prepare a PCR reaction mixture. The PCR reaction was repeatedly performed for one cycle of denaturation at 95° C. for 3 minutes, followed by 30 cycles of denaturation at 94° C. for 30 seconds, annealing at 64° C. for 30 seconds, and extension at 72° C. for 60 seconds. The resulting PCR products were confirmed through electrophoresis (FIG. 11). As a result, it was revealed that the Neq HS M3 DNA polymerase was able to accurately amplify a larger amount of target DNA than the other DNA polymerases. Lane 1 represents the Neq HS M3 DNA polymerase, Lane 2 represents the HS Taq DNA polymerase (Roche), Lane 3 represents the HS Taq DNA polymerase (Takara), Lane 4 represents the Taq DNA polymerase (Takara), and Lane 5 represents the Pfu DNA polymerase (Promega). Lane M represents a GeneRuler™ 1 kb DNA ladder (Fermentas). In the above-described multiplex PCR, only the DNA polymerase for HS PCR was able to amplify the four target genes.

Example 9

Examination of PCR Fidelity of DNA Polymerases

The PCR fidelities of the Neq HS DNA polymerase and the mutant Neq HS M1, Neq HS M2 and Neq M3 HS DNA polymerases were compared to the PCR fidelity of the Pfu DNA polymerase. A method of measuring the PCR fidelity was performed in the same manner as in the method by Song J. M. et al. (Song J. M. et al., 2007, Enzyme Microbe. Technol. 40, 1475-1483; Choi J. J. et al., 2008, Appl. Environ. Microbiol. 74, 6563-6569) according to a modified Lundberg's method (Lundberg et al., 1991, Gene 108(1), 1-6), as follows. First, an 835 bp fragment of a 5' terminal region of an expression vector pJR2-lacZ carrying a lacZ gene was amplified with DNA polymerases to be measured for PCR fidelity. In this case, an optimal PCR buffer for each of the DNA polymerases was used. Next, the PCR-amplified products were digested with the restriction enzymes BamHI and ClaI, and then re-cloned into the expression vector pJR2-lacZ digested with the same restriction enzymes. Thereafter, the PCR-amplified products were ligated overnight with DNA ligase, and transformed into E. coli DH5a. Then, the resulting transformants were evenly spread on an agar plate medium supplemented with antibiotic ampicillin, IPTG and 5-bromo-4-chloro-3-indolyl 13-D-galactopyranoside (X-gal), and cultured at 37° C. for 16 hours. Subsequently, the agar plate was stored at 4° C. for 2 hours, and blue colonies and white colonies were counted. The mutation frequencies and error rates were calculated based on the numbers of the blue and white colonies. The results are listed in the following Table 4. In the PCR using the Neq M2 DNA polymerase, the PCR error rate of the Neq M2 DNA polymerase was approximately 1.7-fold lower than that of the Pfu DNA polymerase, and similar to that that of the Neq M DNA polymerase. Also, in the PCR using the Neq M3 HS DNA polymerase, the PCR error rate of the Neq M3 HS DNA polymerase was approximately 1.6 times that of the Pfu DNA polymerase.

TABLE 3

Comparison of error rates of PCR products between Neq HS DNA polymerase and mutant Neq HS M1, Neq HS M2, Neq HS M3 DNA polymerase, and Pfu DNA polymerase

| | Numbers of colonies | | Mutation frequency[a] | Template doublings[b] | Error rate[c] ($\times 10^{-6}$) |
|---|---|---|---|---|---|
| | Blue | Pale blue and white | | | |
| Neq HS | 4965 | 254 | 0.049 | 6.97 | 8.39 |
| Neq HS M1 | 4006 | 105 | 0.026 | 7.61 | 4.03 |
| Neq HS M2 | 5223 | 97 | 0.018 | 8.02 | 2.73 |
| Neq HS M3 | 2864 | 167 | 0.055 | 8.53 | 7.76 |
| Pfu | 3672 | 105 | 0.028 | 7.04 | 4.75 |

[a]Mutation frequency is expressed as the proportion of mutant colonies (pale blue and white) to the total number of colonies.
[b]Template doublings were calculated according to the equation: $2d$ = amount of PCR products/amount of starting target.
[c]Error rate was calculated according to the equation: $ER = mf/(bp \times d)$. Here, mf represents the mutation frequency, bp represents the size of a lacZ target size (=832 bp), and d represents the number of template doublings.

Example 10

Figure 12:
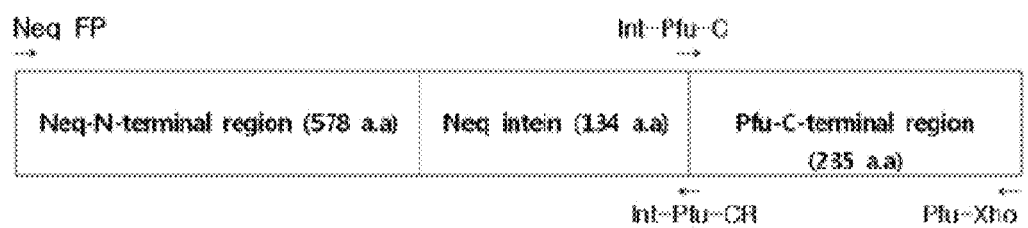
FIG. 12A shows an amino acid sequence (Neq pol) including a split intein and neighboring regions of exteins of the Neq DNA polymerase, and an amino acid sequence (Neq HS pol) including an intein and exteins of the Neq HS DNA polymerase, and 6 histidine residues inserted between and linked with the exteins. The intein is not present in the Pfu DNA polymerase, but the Pfu DNA polymerase has the same amino acid sequence as a junction region of the exteins of the Neq DNA polymerase.
FIG. 12B is a diagram illustrating positions of four primers used to construct a chimeric Nefu HS DNA polymerase by linking a gene coding for a domain including a Neq N terminus and an intein with a gene corresponding to a C-terminal region of the Pfu DNA polymerase.

Preparation of Chimeric Nefu HS DNA Polymerase Using Intein of Neq DNA Polymerase The full-length intein of the Neq HS DNA polymerase was introduced into another thermostable DNA polymerase to examine the applicability to HS PCR. By way of example, the Pfu DNA polymerase had no intein, but the amino acids of an extein junction region of the Neq DNA polymerase were highly conserved (FIG. 12A). FIG. 12A shows Neq N-extein junction region KVIYGD SIMDTEI (SEQ ID NO: 55), Neq C-extein junction region VNGLVLHN TDSLFI (SEQ ID NO: 56), Pfu N-extein junction region KVLYID (SEQ ID NO: 57), and Pfu C-extein junction region TDSLFI (SEQ ID NO: 58). In this Example, a domain including the N terminus and full-length intein of the Neq HS DNA polymerase was ligated with Pfu-C that was a C-terminal domain of the Pfu DNA polymerase to prepare a chimeric Nefu HS DNA polymerase capable of being used in HS PCR. In the present disclosure, the inventors have already ensured the expression vector into which the Pfu DNA polymerase gene was cloned, and information on its gene sequence (GenBank accession No. D12983). Also, the inventors have already ensured the gene of the intein from the Neq HS DNA polymerase and information on its gene sequence (SEQ ID NO: 5, Choi J. J. et al., 2006, J. Mol. Biol. 356:1093-106). Based on these kinds of information, each of primers was synthesized, and a gene corresponding to a Pfu-C fragment was ligated with the rear of the Neq intein through overlap extension PCR to prepare a DNA polymerase for HS PCR (FIG. 12B). Four primers were required to ligate a gene including the Neq N terminus and intein with a gene corresponding to the C-terminal region of the Pfu DNA polymerase. First, the primer set forth in SEQ ID NO: 1 (Neq FP) included a 5' base sequence of the Neq HS DNA polymerase gene. The primer set forth in SEQ ID NO: 37 (Int-Pfu-CR) was obtained by synthesizing a base sequence complementary to a base sequence, which included a 3' base sequence of the intein of the Neq HS DNA polymerase and a portion of a base sequence the Pfu-C fragment of the Pfu DNA polymerase, in a 5'-3' direction (FIG. 12B).

Therefore, the primers set forth in SEQ ID NO: 38 (Int-Pfu-C) and SEQ ID NO: 39 (Pfu-Xho) were synthesized to amplify the Pfu-C fragment (FIG. 12B). That is, the primer set forth in SEQ ID NO: 38 was prepared by synthesizing a base sequence corresponding to a portion of the amino acid sequence of the C-terminal region of the Neq intein and the amino acid sequence of the N terminus of the Pfu-C fragment in a 5'→3' direction. The primer set forth in SEQ ID NO: 39 was prepared by synthesizing a base sequence complementary to a base sequence corresponding to the amino acid sequence of the C-terminal region of the Pfu-C fragment in a 5'-3' direction. For reference, the primer set forth in SEQ ID NO: 39 was synthesized to have an XhoI site in order to facilitate cloning of the expression vector. First, the primers set forth in SEQ ID NOS: 1 and 37 were added to a PCR reaction mixture, and primary PCR was performed in the same manner as in Example 1 using a Neq HS DNA gene as a template, thereby amplifying a gene including the N terminus and intein of the Neq HS. Also, the primers set forth in SEQ ID NOS: 38 and 39 were added to a PCR reaction mixture, and primary PCR was performed in the same manner as in Example 1 using the Pfu DNA polymerase gene as a template, thereby amplifying a gene Pfu-C corresponding to the C-terminal region of the Pfu DNA polymerase. These PCR-amplified products were recovered through agarose gel electrophoresis. The two fragments recovered thus were mixed at the same ratio, denatured at 95° C. for 3 minutes, and annealed again at 50° C. As a result, the gene including the N terminus and intein of the Neq HS partially overlapped a portion of the base sequence of the gene fragment corresponding to the Pfu-C to form a hybrid template. Then, dNTP and the Pfu DNA polymerase were added to the PCR reaction mixture including the hybrid template, and then subjected to overlap extension at 60° C. for 10 minutes. The primers set forth in SEQ ID NOS: 1 and 39 were added, and secondary PCR was performed in the same manner as in Example 1 using the PCR-amplified product as a template to amplify the full-length chimeric Nefu HS DNA polymerase gene in which the N-terminal and intein fragments of the Neq HS was linked with the Pfu-C fragment. Thereafter, the chimeric Nefu HS DNA polymerase gene was digested with the restriction enzymes NdeI/XhoI, and cloned into the restriction site of the expression vector pETRPHIS-5 digested with the same restriction enzymes. Then, E. coli DH5a was transformed with the mixed ligation solution, and plasmid DNA was then separated from the transformants through an alkaline lysis method. The separated plasmid DNA was digested with the restriction enzymes NdeI and XhoI, and electrophoresed in 0.8% agarose gel together with a DNA size marker to re-confirm whether the chimeric Nefu HS DNA polymerase gene was exactly inserted into the expression vector. The expression vector for expression of the chimeric Nefu HS DNA polymerase gene (SEQ ID NO: 40) constructed thus was designated as pETRPNPHS. Also, the amino acid sequence of the Nefu HS DNA polymerase was determined based on the base sequence of the Nefu HS DNA polymerase gene (SEQ ID NO: 41).

SEQ ID NO: 37 (Int-Pfu-CR): 5'-accatcagtattgtgtaaaac-tagcccattaa-3'

SEQ ID NO: 38 (Int-Pfu-C): 5'-gttttacacaatactgatggtctctat-gcaactat-3'

SEQ ID NO: 39 (Pfu-Xho): 5'-NNNNNNCTCGAGctag-gatttttaatgttaagcc-3'

To express the chimeric Nefu HS DNA polymerase gene, E. coli W3110-RILYKT was transformed with the expression vector pETRPNPHS. The E. coli W3110-RILYKT/pETRP-NPHS was seeded in an LB liquid medium supplemented with ampicillin and chloramphenicol at final concentrations of 100 μg/ml and 34 μg/ml, respectively, and cultured overnight at 37° C. Subsequently, 5 ml of the culture broth was taken, seeded in 500 ml of an M9 defined medium (including 0.1% glucose and 0.5% casamino acid) supplemented with ampicillin and chloramphenicol at final concentrations of 100 μg/ml and 34 μg/ml, respectively, and then cultured at 37° C. for 20 hours. The culture broth was centrifuged at 6,000 rpm for 20 minutes to recover a pellet of the strain (3.0 g/wet weight). Then, the pellet was suspended in 20 ml of buffer A (20 mM Tris-HCl (pH 7.4), 0.3 M NaCl) including 1 mM PMSF, homogenized by sonication, and then centrifuged at 18,000 rpm for 30 minutes to remove the E. coli cell debris. The resulting supernatant was attached to a HisTrap™ HP column (GE Healthcare) equilibrated with buffer A, and then washed thoroughly with the same buffer A. The proteins attached to the column were eluted with the same buffer with a 0 to 0.5 M imidazole gradient. The peak fractions expected to contain the DNA polymerase were selected, and sufficiently dialyzed in buffer B (20 mM Tris-HCl (pH 8.8), 0.1 M NaCl, 1 mM DTT). The sufficiently dialyzed sample was attached to an anion-exchange column, HiTrap™ Q column (GE Healthcare), which was equilibrated with the buffer B. The column was washed thoroughly with buffer B, and the DNA polymerase attached to the column was then eluted with the same buffer with a 0.1 to 1 M NaCl gradient. The DNA polymerases finally purified through the above-described method were dialyzed in a storage buffer (20 mM Tris-HCl (pH 7.4), 0.1 mM EDTA, 0.1% Tween 20, 0.1% Nonidet P40, 50 mM KCl, 1 mM DTT, 50% Glycerol), and stored at −20° C. The dialyzed DNA polymerases were used whenever PCR were performed. The purified proteins were quantified using a Bradford assay. The amount of the finally purified chimeric Nefu HS DNA polymerase was 0.9 mg.

Figure 13:
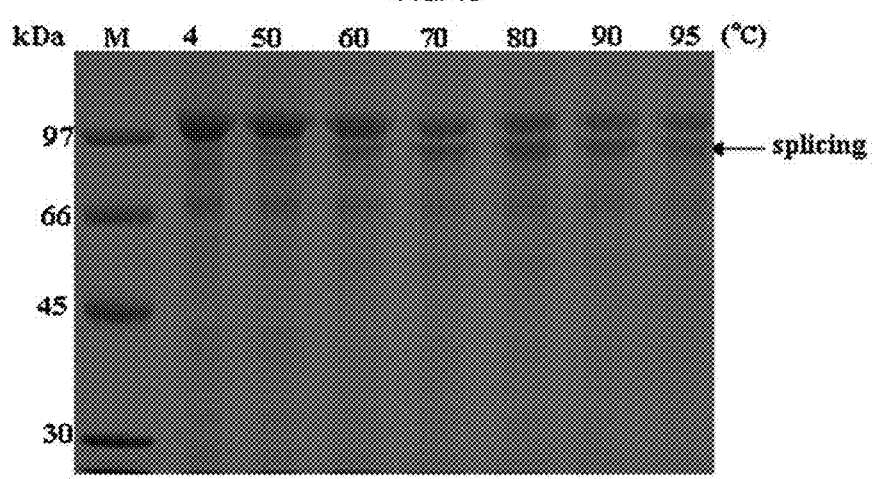
FIG. 13 shows the results obtained by analyzing an effect of a protein splicing reaction according to a reaction temperature after 12 μg of a chimeric Nefu HS DNA polymerase is added. The protein splicing reaction is performed at a reaction temperature of 50 to 95° C., and the resulting reaction solution is analyzed through SDS-denatured gel electrophoresis.

To examine an effect of the chimeric Nefu HS DNA polymerase on protein splicing at a high temperature, first, the purified Nefu HS DNA polymerase (12 μg) was added to a protein splicing reaction solution (20 mM Tris-HCl (pH 8.0), 50 mM NaCl), reacted at temperature of 50 to 95° C. for 30 minutes, and analyzed through SDS-PAGE (FIG. 13). As a result, it could be seen that the amount of the purified chimeric Nefu HS DNA polymerase (having a molecular weight of approximately 110 kDa) was decreased as the reaction temperature increased, while the amount of the protein-spliced product, chimeric Nefu (chimeric Nefu DNA polymerase having a molecular weight of approximately 90 kDa) was increased (FIG. 13). Also, it could be seen that the protein splicing occurred only at 70° C. or over. FIG. 13 shows the results obtained by analyzing the protein splicing according to a reaction temperature using the purified chimeric Nefu HS DNA polymerase. In FIG. 13, Lane M represents a low molecular weight protein marker loaded in gel.

Figure 14:
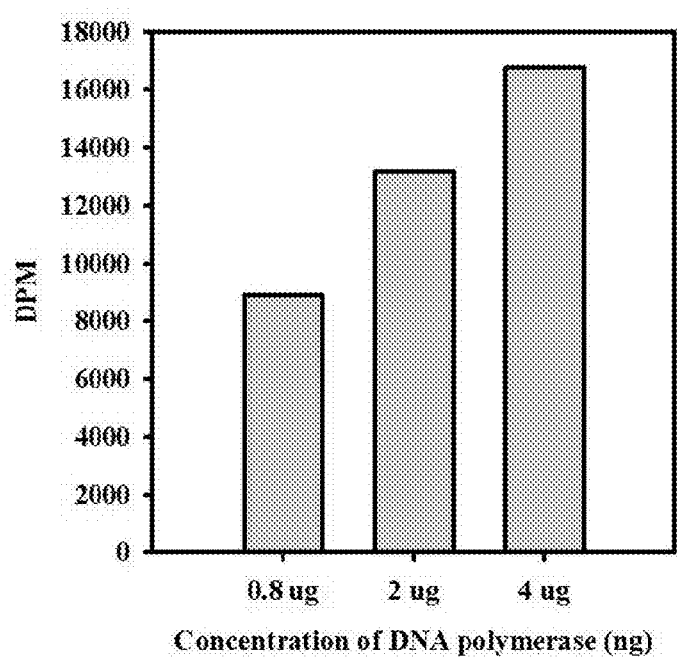
FIG. 14 shows the results obtained by measuring the activities of the chimeric Nefu HS DNA polymerase in a reaction solution for splicing a chimeric Nefu HS DNA polymerase protein, depending on the concentration of enzyme.

FIG. 14 shows the results obtained by measuring the activities of the chimeric Nefu HS DNA polymerase in a reaction solution for protein splicing a chimeric Nefu HS DNA polymerase according to the concentration of the enzyme. The activities of the DNA polymerase were measured in the same manner as in Example 5 in the reaction solution in which the chimeric Nefu HS DNA polymerase was reacted at 80° C. for 30 minutes in the protein splicing reaction solution (20 mM Tris-HCl (pH 8.0), 50 mM NaCl). The results obtained by measuring the activities of the DNA polymerase in the protein splicing reaction solution according to the amount of the chimeric Nefu HS DNA polymerase are shown in FIG. 14. As a result, it could be seen that the activities of the DNA polymerase increased with dpm values as the amount of the enzyme increased, indicating that the chimeric Nefu HS DNA polymerase was active.

Figure 15:
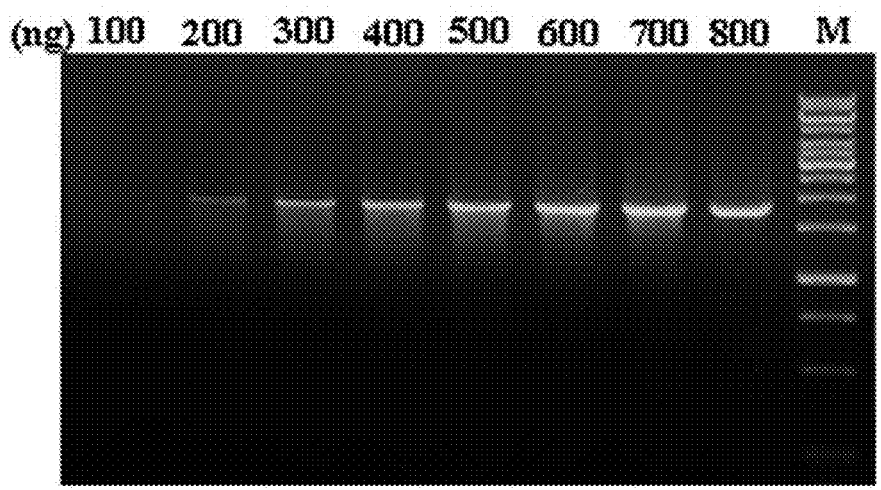
FIG. 15 shows the results obtained by performing PCR on Lambda DNA (2 kb) as a PCR target in the presence of dNTP using the chimeric Nefu HS DNA polymerase.

FIG. 15 shows the results obtained by performing PCR of the chimeric Nefu HS DNA polymerase using Lambda DNA as a template. Here, the PCR target fragment was a 2 kb fragment of the Lambda DNA. First, a PCR reaction solution (50 μl) for amplifying the 2 kb fragment of Lambda DNA was composed as follows. 10 pmol of each of a forward primer (Lambda_DNA_F: 5'-CCTGCTCTGCCGCTCACGC-3' (SEQ ID NO: 55)) and a reverse primer (Lambda_DNA_R: 5'-CCATGATTCAGTGTGCCCGTCTGG-3' (SEQ ID NO: 56)) for targeting the 2 kb fragment of Lambda DNA, 25 ng of human genomic DNA, 250 μM dNTPs, the chimeric Nefu HS DNA polymerase, 30 mM Tricine-KOH (pH 8.6), 1.5 mM MgCl$_2$, 70 mM KCl, and 0.05% Tween 20 were added to prepare a PCR reaction solution. For reference, the DNA polymerase added was present at an amount of 100 to 800 ng in 50 μl of the PCR reaction solution. The PCR reaction was repeatedly performed for one cycle of denaturation at 80° C. for 10 minutes, followed by 30 cycles of denaturation at 95° C. for 30 seconds, annealing at 60° C. for 30 seconds, and extension at 72° C. for 2 minutes. Thereafter, the resulting PCR products were finally subjected to agarose gel electrophoresis in order to determine the length of the PCR products (FIG. 15). Each Lane represents the amount of a chimeric Nefu HS DNA polymerase, and Lane M represents a GeneRuler™ 1 kb DNA ladder (Fermentas). In this case, it was confirmed that the 2 kb fragment of Lambda DNA was amplified by the chimeric Nefu HS DNA polymerase (FIG. 15). Accordingly, it was proven that the intein of the Neq DNA polymerase was introduced into other DNA polymerases so that the intein of the Neq DNA polymerase was applicable to HS PCR.

According to the present disclosure, a Neq hot-start (HS) DNA polymerase in the form of a precursor of Neq DNA polymerase was prepared by linking the inteins of Neq L and Neq S fragments with each other. The Neq HS DNA polymerases including the intein were expressed under the control of a tryptophan promoter of the newly constructed expression vector pETRPHIS-5. To facilitate an increase in expression level, a tRNA codon plasmid was constructed, and an expression host, E. coli W3110, was transformed with the tRNA codon plasmid. As a result, it was revealed that the expression rate increased. A His-tag sequence composed of six histidine residues was inserted between the inteins of the Neq L and Neq S fragments at a gene level. As a result, the recombinant Neq HS DNA polymerases could be easily purified. Also, a variety of mutant Neq HS DNA polymerases (M1, M2, M3) were prepared to facilitate an increase in PCR efficiency. When PCR was performed using these mutants, the mutant Neq HS DNA polymerases had more excellent PCR efficiency than the wild-type Neq HS DNA polymerase. In particular, when PCR was performed using human chromosomal DNA as a template and the Neq HS M3 DNA polymerase, the PCR-amplified products could be obtained with higher specificity that those of the other DNA polymerases. Also, the mutant Neq HS DNA polymerases had better amplification efficiency and specificity in the presence of deoxy-UTP (dUTP) than the Taq DNA polymerase. Accordingly, the present disclosure can be effectively used for prevention of carry-over contamination of nucleic acid samples including dUTP together with uracil-DNA glycosylase (UDG), and used in multiplex PCR.

It will be apparent to those skilled in the art that various modifications can be made to the above-described exemplary embodiments of the present disclosure without departing from the scope of the disclosure. Thus, it is intended that the present disclosure covers all such modifications provided they come within the scope of the appended claims and their equivalents.

While this disclosure includes specific examples, it will be apparent to one of ordinary skill in the art that various changes in form and details may be made in these examples without departing from the spirit and scope of the claims and their equivalents. The examples described herein are to be considered in a descriptive sense only, and not for purposes of limitation. Descriptions of features or aspects in each example are to be considered as being applicable to similar features or aspects in other examples. Suitable results may be achieved if the described techniques are performed in a different order, and/or if components in a described system are combined in a different manner and/or replaced or supplemented by other components or their equivalents. Therefore, the scope of the disclosure is defined not by the detailed description, but by the claims and their equivalents, and all variations within the scope of the claims and their equivalents are to be construed as being included in the disclosure.

What is claimed is:

1. A thermostable hot-start DNA polymerase, wherein the thermostable hot-start DNA polymerase comprises the amino acid sequence set forth in SEQ ID NO: 6, SEQ ID NO: 32, SEQ ID NO: 34, or SEQ ID NO: 36.

2. The thermostable hot-start DNA polymerase of claim 1, wherein the thermostable hot-start DNA polymerase comprises the amino acid sequence set forth in SEQ ID NO: 6.

3. An isolated polynucleotide comprising a nucleotide sequence that encodes the thermostable hot-start DNA polymerase of claim 1.

4. A recombinant vector comprising the polynucleotide of claim 3.

5. An isolated host cell transformed with the recombinant vector of claim 4.

6. The host cell of claim 5, wherein the host cell is an *Escherichia* coli.

7. A method of preparing the thermostable hot-start DNA polymerase of claim 1, comprising:
preparing a recombinant expression vector comprising a nucleotide sequence encoding the thermostable hot-start DNA polymerase of claim 1;
preparing a transformant by transforming an isolated host cell with the recombinant expression vector;
producing the thermostable hot-start DNA polymerase by culturing the transformant; and purifying the thermostable hot-start DNA polymerase from the transformant.

8. A method of performing a hot-start polymerase chain reaction (HS PCR) comprising:
 combining the thermostable hot-start DNA polymerase of claim 1 with components necessary for HS PCR to produce a HS PCR reaction mixture;
 heating the reaction mixture for protein trans-splicing of the thermostable hot-start DNA polymerase to form an active DNA polymerase; and
 performing HS PCR.

9. The method of performing a hot-start PCR of claim 8, wherein the heating is at a temperature of 50 to 100° C.

10. The thermostable hot-start DNA polymerase of claim 1, wherein the thermostable hot-start DNA polymerase comprises the amino acid sequence set forth in SEQ ID NO: 32.

11. The thermostable hot-start DNA polymerase of claim 1, wherein the thermostable hot-start DNA polymerase comprises the amino acid sequence set forth in SEQ ID NO: 34.

12. The thermostable hot-start DNA polymerase of claim 1, wherein the thermostable hot-start DNA polymerase comprises the amino acid sequence set forth in SEQ ID NO: 36.

* * * * *

SEQUENCE LISTING

```
<160> NUMBER OF SEQ ID NOS: 58

<210> SEQ ID NO 1
<211> LENGTH: 31
<212> TYPE: DNA
<213> ORGANISM: Artificial Sequence
<220> FEATURE:
<223> OTHER INFORMATION: Neq FP

<400> SEQUENCE: 1
attatagcat atgttacacc aactccccac g                              31

<210> SEQ ID NO 2
<211> LENGTH: 47
<212> TYPE: DNA
<213> ORGANISM: Artificial Sequence
<220> FEATURE:
<223> OTHER INFORMATION: HisNeqM

<400> SEQUENCE: 2
atgtggtgat ggtgatggtg attattttta ttttcatatt ccttggc             47

<210> SEQ ID NO 3
<211> LENGTH: 47
<212> TYPE: DNA
<213> ORGANISM: Artificial Sequence
<220> FEATURE:
<223> OTHER INFORMATION: HisNeqMR

<400> SEQUENCE: 3
aatcaccatc accatcacca caatgcgcta tcttggcaaa aagagag             47

<210> SEQ ID NO 4
<211> LENGTH: 36
<212> TYPE: DNA
<213> ORGANISM: Artificial Sequence
<220> FEATURE:
<223> OTHER INFORMATION: NeqSRSalstop
<220> FEATURE:
<221> NAME/KEY: misc_feature
<222> LOCATION: (1)..(6)
<223> OTHER INFORMATION: n is a, c, g, or t

<400> SEQUENCE: 4
nnnnnngtcg actttaaaga aatctgttag tttttt                         36

<210> SEQ ID NO 5
<211> LENGTH: 2808
<212> TYPE: DNA
<213> ORGANISM: Artificial Sequence
<220> FEATURE:
<223> OTHER INFORMATION: Neq HS DNA polymerase

<400> SEQUENCE: 5
atgttacacc aactccccac gatggttgta gaagaaaagg cggtaaaaga ggaagaaggg    60
tatagcgtgc taaaatgtta ttggattaat atagagaaca cccctttaga cgaggtaatt   120
ttaataggta aagacgaaaa taatagagct tgtgaagtta taattccata caatggtat    180
```

```
ttctattttg aaggcgatat aaaggattta gaagaattcg ctaacaacaa aaaaataaaa      240
atcgaatata caaggagca aaagaaatat atagaaaaac caaagatgt ttataaagta       300 tatgttttgc ataaacatta tccaatacta aaagaattca ttaaagaaaa gggctataaa     360
aaatacgaaa ccgatataaa tgtttatagg aagttttaa tagataaagg datagagcct     420
tttgaatggt ttgaggtaga aggcaaaatt ttattatcta cctctaacaa agttagaata    480
aaagcacaaa gtataaaaag attgtatgaa aagactaagc catcggtttt agcttttgat    540
atagaagttt acagtgaggc tttccctaat cctgaaaaag acaaaataat atctatagcc    600
ctttatggag acaattacga aggggttatc tcttacaaag gagaaccaac tataaaagtt    660
aataccgaat atgaattaat tgagaaattt gtcgaaataa tagaaagctt aaaaccagac    720
ataatagtta catacaatgg ggataatttc gatatagact ttttagtgaa aagggcttct    780
ttatacaata taaggctacc aataaaattg gttaacaaaa aagagcctac ttataatttt    840
agggaaagcg cacatgtaga tttgtataaa acaattacta ccatatataa aacccaattg    900
tctacccaaa catattcatt aaatgaagta gctaaagaaa ttcttggaga ggagaaaatt    960
tatgattatg aaaacatgtt atatgattgg gccataggca attataacaa agtgttcgaa   1020
tacaatttaa aagatgccga attaacatat aagctattca aatactatga aaatgattta   1080
ttggaattag caagattggt taaccaacca ttatttgatg tatctaggtt tagctatagt   1140
aatatagttg aatggtatct aatcaaaaaa agcagaaaat ataatgaaat tgtgcctaac   1200
aaaccaaaaa tggaagaagt agagagaaga aaattaaata cctatgcagg agcattcgtt   1260
tacgaaccaa aacccggttt gtatgagaat ttagctgtac tggatttcgc ttctctgtat   1320
ccttcaatta tattagagca taatgtttct ccaggcacaa tatattgtga gcatgatgat   1380
tgtaaacaaa atggggtaga agcgataata aataatgaga aaaatatgt gtggttttgc    1440 aaaaaagtaa aagggtttat tccaacggta ttagagcatt tgtatacaaa aaggctagaa   1500
cttaagagaa aactgaaaga actagatagg gatagtgaag aatatataaat tataaatgct  1560 aagcaagcag tattgaaaat aataattaat gcaacctatg ctatatgggg tttcccaaat   1620
gcgagatggt attgcataga ctgtgctgcg gcagtagcag cttggggcag gaaatacatt   1680
aattatatat taaaaagggc cgaagaagaa ggattcaaag taatttatgg agattctata   1740
atggatactg aaatagaggt tatagaaaat ggtataaaaa agaaagaaaa gctaagcgat   1800
ttgtttaaca aatactatgc cggttttcaa ataggggaga acattatgc tttccctcca    1860 gatttgtatg tatatgatgg agaaagatgg gttaaagtat attcaataat aaaacatgaa   1920
accgagaccg atttatatga aataaatggg ataacattaa gtgcaaacca tttagtttta   1980
agcaaaggca attgggttaa agccaaggaa tatgaaaata aaaataatca ccatcaccat   2040
caccacatgc gctatcttgg caaaaagaga gttatttat atgatttatc tactgaatcg    2100
ggtaaatttt atgttaatgg gctagtttta cacaataccg attcattatt catttctggg    2160
gacaaagaca agtattagaa attttagag aaagtaaata aagaattacc cggtaaaata    2220
caattagatt tagaagattt ctatgttaga gggatattcg taaaaagag gggtgaacaa    2280 aaggggcaa aaagaaata tgctttatta gcgaacaag gttacataaa gctaaggggc      2340
ttcgaagcag taagaacaga ctgggctccc atagttaaag aagtccaaac aaagctattg    2400
gaaattttgc taaagaagg taacatagaa aaagcaagac aatacataaa agaaattatt    2460
agaaagctaa gaaatagaga aataccatgg gagaagcttt taattacaga aacgataaga    2520
aagcctttag aaaaatacaa agttgaagct cctcatgtgg cagcagcaaa aaaatataaa    2580
```

```
aggttgggct ataaagttat gcctggcttt agagttagat atttagtggt aggtagcact    2640
ggaagggttt cagatagaat taaaatagac aaagaagtta ggggtaatga atatgacccc    2700
gaatactaca tagaaaaaca actattgcct gcagtagagc aaatattaga atctgtaggt    2760
attaaagaca cattcacagg caaaaaacta acagatttct ttaaatga                2808
```

<210> SEQ ID NO 6
<211> LENGTH: 935
<212> TYPE: PRT
<213> ORGANISM: Artificial Sequence
<220> FEATURE:
<223> OTHER INFORMATION: Neq HS DNA polymerase

<400> SEQUENCE: 6

| | | | | | | | | | | | | | | | |
|---|---|---|---|---|---|---|---|---|---|---|---|---|---|---|---|
| Met | Leu | His | Gln | Leu | Pro | Thr | Met | Val | Val | Glu | Glu | Lys | Ala | Val | Lys |
| 1 | | | | 5 | | | | | 10 | | | | | 15 | |
| Glu | Glu | Glu | Gly | Tyr | Ser | Val | Leu | Lys | Cys | Tyr | Trp | Ile | Asn | Ile | Glu |
| | | | 20 | | | | | 25 | | | | | 30 | | |
| Asn | Thr | Pro | Leu | Asp | Glu | Val | Ile | Leu | Ile | Gly | Lys | Asp | Glu | Asn | Asn |
| | | 35 | | | | | 40 | | | | | 45 | | | |
| Arg | Ala | Cys | Glu | Val | Ile | Ile | Pro | Tyr | Lys | Trp | Tyr | Phe | Tyr | Phe | Glu |
| | 50 | | | | | 55 | | | | | 60 | | | | |
| Gly | Asp | Ile | Lys | Asp | Leu | Glu | Glu | Phe | Ala | Asn | Asn | Lys | Lys | Ile | Lys |
| 65 | | | | | 70 | | | | | 75 | | | | | 80 |
| Ile | Glu | Tyr | Thr | Lys | Glu | Gln | Lys | Lys | Tyr | Ile | Glu | Lys | Pro | Lys | Asp |
| | | | | 85 | | | | | 90 | | | | | 95 | |
| Val | Tyr | Lys | Val | Tyr | Val | Leu | His | Lys | His | Tyr | Pro | Ile | Leu | Lys | Glu |
| | | | | 100 | | | | | 105 | | | | | 110 | |
| Phe | Ile | Lys | Glu | Lys | Gly | Tyr | Lys | Lys | Tyr | Glu | Thr | Asp | Ile | Asn | Val |
| | | | 115 | | | | | 120 | | | | | 125 | | |
| Tyr | Arg | Lys | Phe | Leu | Ile | Asp | Lys | Gly | Ile | Glu | Pro | Phe | Glu | Trp | Phe |
| | 130 | | | | | 135 | | | | | 140 | | | | |
| Glu | Val | Glu | Gly | Lys | Ile | Leu | Leu | Ser | Thr | Ser | Asn | Lys | Val | Arg | Ile |
| 145 | | | | | 150 | | | | | 155 | | | | | 160 |
| Lys | Ala | Gln | Ser | Ile | Lys | Arg | Leu | Tyr | Glu | Lys | Thr | Lys | Pro | Ser | Val |
| | | | | 165 | | | | | 170 | | | | | 175 | |
| Leu | Ala | Phe | Asp | Ile | Glu | Val | Tyr | Ser | Glu | Ala | Phe | Pro | Asn | Pro | Glu |
| | | | 180 | | | | | 185 | | | | | 190 | | |
| Lys | Asp | Lys | Ile | Ile | Ser | Ile | Ala | Leu | Tyr | Gly | Asp | Asn | Tyr | Glu | Gly |
| | | | 195 | | | | | 200 | | | | | 205 | | |
| Val | Ile | Ser | Tyr | Lys | Gly | Glu | Pro | Thr | Ile | Lys | Val | Asn | Thr | Glu | Tyr |
| | 210 | | | | | 215 | | | | | 220 | | | | |
| Glu | Leu | Ile | Glu | Lys | Phe | Val | Glu | Ile | Ile | Glu | Ser | Leu | Lys | Pro | Asp |
| 225 | | | | | 230 | | | | | 235 | | | | | 240 |
| Ile | Ile | Val | Thr | Tyr | Asn | Gly | Asp | Asn | Phe | Asp | Ile | Asp | Phe | Leu | Val |
| | | | | 245 | | | | | 250 | | | | | 255 | |
| Lys | Arg | Ala | Ser | Leu | Tyr | Asn | Ile | Arg | Leu | Pro | Ile | Lys | Leu | Val | Asn |
| | | | 260 | | | | | 265 | | | | | 270 | | |
| Lys | Lys | Glu | Pro | Thr | Tyr | Asn | Phe | Arg | Glu | Ser | Ala | His | Val | Asp | Leu |
| | | | 275 | | | | | 280 | | | | | 285 | | |
| Tyr | Lys | Thr | Ile | Thr | Ile | Tyr | Lys | Thr | Gln | Leu | Ser | Thr | Gln | Thr |
| | 290 | | | | | 295 | | | | | 300 | | | | |
| Tyr | Ser | Leu | Asn | Glu | Val | Ala | Lys | Glu | Ile | Leu | Gly | Glu | Glu | Lys | Ile |
| 305 | | | | | 310 | | | | | 315 | | | | | 320 |

```
Tyr Asp Tyr Glu Asn Met Leu Tyr Asp Trp Ala Ile Gly Asn Tyr Asn
            325                 330                 335

Lys Val Phe Glu Tyr Asn Leu Lys Asp Ala Glu Leu Thr Tyr Lys Leu
            340                 345                 350

Phe Lys Tyr Tyr Glu Asn Asp Leu Leu Glu Leu Ala Arg Leu Val Asn
            355                 360                 365

Gln Pro Leu Phe Asp Val Ser Arg Phe Ser Tyr Ser Asn Ile Val Glu
370                 375                 380

Trp Tyr Leu Ile Lys Lys Ser Arg Lys Tyr Asn Glu Ile Val Pro Asn
385                 390                 395                 400

Lys Pro Lys Met Glu Glu Val Glu Arg Arg Lys Leu Asn Thr Tyr Ala
                405                 410                 415

Gly Ala Phe Val Tyr Glu Pro Lys Pro Gly Leu Tyr Glu Asn Leu Ala
                420                 425                 430

Val Leu Asp Phe Ala Ser Leu Tyr Pro Ser Ile Ile Leu Glu His Asn
                435                 440                 445

Val Ser Pro Gly Thr Ile Tyr Cys Glu His Asp Asp Cys Lys Gln Asn
                450                 455                 460

Gly Val Glu Ala Ile Ile Asn Asn Glu Lys Lys Tyr Val Trp Phe Cys
465                 470                 475                 480

Lys Lys Val Lys Gly Phe Ile Pro Thr Val Leu Glu His Leu Tyr Thr
                485                 490                 495

Lys Arg Leu Glu Leu Lys Arg Lys Leu Lys Glu Leu Asp Arg Asp Ser
                500                 505                 510

Glu Glu Tyr Lys Ile Ile Asn Ala Lys Gln Ala Val Leu Lys Ile Ile
                515                 520                 525

Ile Asn Ala Thr Tyr Gly Tyr Met Gly Phe Pro Asn Ala Arg Trp Tyr
530                 535                 540

Cys Ile Asp Cys Ala Ala Ala Val Ala Ala Trp Gly Arg Lys Tyr Ile
545                 550                 555                 560

Asn Tyr Ile Leu Lys Arg Ala Glu Glu Gly Phe Lys Val Ile Tyr
                565                 570                 575

Gly Asp Ser Ile Met Asp Thr Glu Ile Glu Val Ile Glu Asn Gly Ile
                580                 585                 590

Lys Lys Lys Glu Lys Leu Ser Asp Leu Phe Asn Lys Tyr Tyr Ala Gly
                595                 600                 605

Phe Gln Ile Gly Glu Lys His Tyr Ala Phe Pro Pro Asp Leu Tyr Val
                610                 615                 620

Tyr Asp Gly Glu Arg Trp Val Lys Val Tyr Ser Ile Ile Lys His Glu
625                 630                 635                 640

Thr Glu Thr Asp Leu Tyr Glu Ile Asn Gly Ile Thr Leu Ser Ala Asn
                645                 650                 655

His Leu Val Leu Ser Lys Gly Asn Trp Val Lys Ala Lys Glu Tyr Glu
                660                 665                 670

Asn Lys Asn Asn His His His His His Met Arg Tyr Leu Gly Lys
                675                 680                 685

Lys Arg Val Ile Leu Tyr Asp Leu Ser Thr Glu Ser Gly Lys Phe Tyr
                690                 695                 700

Val Asn Gly Leu Val Leu His Asn Thr Asp Ser Leu Phe Ile Ser Gly
705                 710                 715                 720

Asp Lys Asp Lys Val Leu Glu Phe Leu Glu Lys Val Asn Lys Glu Leu
                725                 730                 735

Pro Gly Lys Ile Gln Leu Asp Leu Glu Asp Phe Tyr Val Arg Gly Ile
```

```
                740                 745                 750
Phe Val Lys Lys Arg Gly Glu Gln Lys Gly Ala Lys Lys Tyr Ala
            755                 760                 765

Leu Leu Ser Glu Gln Gly Tyr Ile Lys Leu Arg Gly Phe Glu Ala Val
        770                 775                 780

Arg Thr Asp Trp Ala Pro Ile Val Lys Glu Val Gln Thr Lys Leu Leu
785                 790                 795                 800

Glu Ile Leu Leu Lys Glu Gly Asn Ile Glu Lys Ala Arg Gln Tyr Ile
                805                 810                 815

Lys Glu Ile Ile Arg Lys Leu Arg Asn Arg Glu Ile Pro Trp Glu Lys
            820                 825                 830

Leu Leu Ile Thr Glu Thr Ile Arg Lys Pro Leu Glu Lys Tyr Lys Val
        835                 840                 845

Glu Ala Pro His Val Ala Ala Lys Lys Tyr Lys Arg Leu Gly Tyr
                850                 855                 860

Lys Val Met Pro Gly Phe Arg Val Arg Tyr Leu Val Val Gly Ser Thr
865                 870                 875                 880

Gly Arg Val Ser Asp Arg Ile Lys Ile Asp Lys Glu Val Arg Gly Asn
                885                 890                 895

Glu Tyr Asp Pro Glu Tyr Tyr Ile Glu Lys Gln Leu Leu Pro Ala Val
                900                 905                 910

Glu Gln Ile Leu Glu Ser Val Gly Ile Lys Asp Thr Phe Thr Gly Lys
            915                 920                 925

Lys Leu Thr Asp Phe Phe Lys
        930                 935

<210> SEQ ID NO 7
<211> LENGTH: 37
<212> TYPE: DNA
<213> ORGANISM: Artificial Sequence
<220> FEATURE:
<223> OTHER INFORMATION: TrpPFPvuII
<220> FEATURE:
<221> NAME/KEY: misc_feature
<222> LOCATION: (1)..(6)
<223> OTHER INFORMATION: n is a, c, g, or t

<400> SEQUENCE: 7
nnnnnncagc tgatgagctg ttgacaatta atcatcg                    37

<210> SEQ ID NO 8
<211> LENGTH: 34
<212> TYPE: DNA
<213> ORGANISM: Artificial Sequence
<220> FEATURE:
<223> OTHER INFORMATION: TrpPRNdeI-2
<220> FEATURE:
<221> NAME/KEY: misc_feature
<222> LOCATION: (1)..(6)
<223> OTHER INFORMATION: n is a, c, g, or t

<400> SEQUENCE: 8
nnnnnncata tgataccctt tttacgtgaa cttg                       34

<210> SEQ ID NO 9
<211> LENGTH: 2987
<212> TYPE: DNA
<213> ORGANISM: Artificial Sequence
<220> FEATURE:
<223> OTHER INFORMATION: pETRPHIS-5

<400> SEQUENCE: 9
```

```
atccggatat agttcctcct ttcagcaaaa aaccccctcaa gacccgttta gaggccccaa      60
ggggttatgc tagttattgc tcagcggtgg cagcagccaa ctcagcttcc tttcgggctt     120
tgttagcagc cggatctcag tggtggtggt ggtggtgctc gagtgcggcc gcaagcttgt     180
cgacggagct cgaattcgga tccgaattaa ttccgatatc catggccatc gccggctggg     240
cagcgaggag cagcagacca gcagcagcgg tcggcagcag gtatttcata tgatacccctt    300
tttacgtgaa cttgcgtact agttaactag ttcgatgatt aattgtcaac agctcatcag     360
ctgcctcgcg cgtttcggtg atgacggtga aaacctctga cacatgcagc tcccggagac     420
ggtcacagct tgtctgtaag cggatgccgg gagcagacaa gcccgtcagg gcgcgtcagc     480
gggtgttggc gggtgtcggg gcgcagccat gacccagtca cgtagcgata gcggagtgta     540
tactggctta actatgcggc atcagagcag attgtactga gagtgcacca tatatgcggt     600
gtgaaatacc gcacagatgc gtaaggagaa ataccgcat  caggcgctct ccgcttcct     660
cgctcactga ctcgctgcgc tcggtcgttc ggctgcggcg agcggtatca gctcactcaa     720
aggcggtaat acggttatcc acagaatcag gggataacgc aggaaagaac atgtgagcaa     780
aaggccagca aaaggccagg aaccgtaaaa aggccgcgtt gctggcgttt ttccataggc     840
tccgcccccc tgacgagcat cacaaaaatc gacgctcaag tcagaggtgg cgaaacccga     900
caggactata aagataccag gcgtttcccc ctggaagctc cctcgtgcgc tctcctgttc     960
cgaccctgcc gcttaccgga tacctgtccg cctttctccc ttcgggaagc gtggcgcttt    1020
ctcatagctc acgctgtagg tatctcagtt cggtgtaggt cgttcgctcc aagctgggct    1080
gtgtgcacga accccccgtt cagcccgacc gctgcgcctt atccggtaac tatcgtcttg    1140
agtccaaccc ggtaagacac gacttatcgc cactggcagc agccactggt aacaggatta    1200
gcagagcgag gtatgtaggc ggtgctacag agttcttgaa gtggtggcct aactacggct    1260
acactagaag gacagtattt ggtatctgcg ctctgctgaa gccagttacc ttcggaaaaa    1320
gagttggtag ctcttgatcc ggcaaacaaa ccaccgctgg tagcggtggt ttttttgttt    1380
gcaagcagca gattacgcgc agaaaaaaag gatctcaaga agatcctttg atcttttcta    1440
cggggtctga cgctcagtgg aacgaaaact cacgttaagg gattttggtc atgagattat    1500
caaaaaggat cttcacctag atccttttaa attaaaaatg aagttttaaa tcaatctaaa    1560
gtatatatga gtaaacttgg tctgacagtt accaatgctt aatcagtgag gcacctatct    1620
cagcgatctg tctatttcgt tcatccatag ttgcctgact ccccgtcgtg tagataacta    1680
cgatacggga gggcttacca tctggcccca gtgctgcaat gataccgcga cccacgctct    1740
caccggctcc agatttatca gcaataaacc agccagccgg aagggccgag cgcagaagtg    1800
gtcctgcaac tttatccgcc tccatccagt ctattaattg ttgccgggaa gctagagtaa    1860
gtagttcgcc agttaatagt ttgcgcaacg ttgttgccat tgctgcaggc atcgtggtgt    1920
cacgctcgtc gtttggtatg gcttcattca gctccggttc ccaacgatca aggcgagtta    1980
catgatcccc catgttgtgc aaaaaagcgg ttagctcctt cggtcctccg atcgttgtca    2040
gaagtaagtt ggccgcagtg ttatcactca tggttatggc agcactgcat aattctctta    2100
gagaatagtg tatgcggcga ccgagttgct cttgcccggc gtcaatacgg gataataccg    2160
cgccacatag cagaacttta aaagtgctca tcattggaaa acgttcttcg ggcgaaaac     2220
tctcaaggat cttaccgctg ttgagatcca gttcgatgta acccactcgt gcacccaact    2280
gatcttcagc atcttttact ttcaccagcg tttctgggtg agcaaaaaca ggaaggcaaa    2340
```

```
atgccgcaaa aaagggaata agggcgacac ggaaatgttg aatactcata ctcttccttt    2400
ttcaatatta ttgaagcatt tatcagggtt attgtctcat gagcggatac atatttgaat    2460
gtatttagaa aaataaacaa ataggggttc cgcgcacatt tccccgaaaa gtgccacctg    2520
aaattgtaaa cgttaatatt ttgttaaaat tcgcgttaaa ttttttgttaa atcagctcat    2580 tttttaacca ataggccgaa atcggcaaaa tcccttataa atcaaaagaa tagaccgaga    2640
tagggttgag tgttgttcca gtttggaaca agagtccact attaaagaac gtggactcca    2700
acgtcaaagg gcgaaaaacc gtctatcagg gcgatggccc actacgtgaa ccatcaccct    2760
aatcaagttt tttggggtcg aggtgccgta aagcactaaa tcggaaccct aaagggagcc    2820
cccgatttag agcttgacgg ggaaagccgg cgaacgtggc gagaaaggaa gggaagaaag    2880
cgaaaggagc gggcgctagg gcgctggcaa gtgtagcggt cacgctgcgc gtaaccacca    2940 caccgccgc gcttaatgcg ccgctacagg gcgcgtccca ttcgcca               2987
```

<210> SEQ ID NO 10
<211> LENGTH: 29
<212> TYPE: DNA
<213> ORGANISM: Artificial Sequence
<220> FEATURE:
<223> OTHER INFORMATION: tRNA Nde

<400> SEQUENCE: 10
ctggccacgg gtgcatatga tcgtgctcc                                     29

<210> SEQ ID NO 11
<211> LENGTH: 29
<212> TYPE: DNA
<213> ORGANISM: Artificial Sequence
<220> FEATURE:
<223> OTHER INFORMATION: tRNA NdeR

<400> SEQUENCE: 11
ggagcacgat catatgcacc cgtggccag                                     29

<210> SEQ ID NO 12
<211> LENGTH: 32
<212> TYPE: DNA
<213> ORGANISM: Artificial Sequence
<220> FEATURE:
<223> OTHER INFORMATION: tRNA YXhoF
<220> FEATURE:
<221> NAME/KEY: misc_feature
<222> LOCATION: (1)..(6)
<223> OTHER INFORMATION: n is a, c, g, or t

<400> SEQUENCE: 12
nnnnnnctcg agccttcccc gcatgggcag aa                                 32

<210> SEQ ID NO 13
<211> LENGTH: 33
<212> TYPE: DNA
<213> ORGANISM: Artificial Sequence
<220> FEATURE:
<223> OTHER INFORMATION: tRNA YKR

<400> SEQUENCE: 13
gttagcaccc gccgtgccac caccataatt cac                                33

<210> SEQ ID NO 14
<211> LENGTH: 33
<212> TYPE: DNA
<213> ORGANISM: Artificial Sequence
<220> FEATURE:
<223> OTHER INFORMATION: tRNA YKF

<400> SEQUENCE: 14
gtgaattatg gtggtggcac ggcgggtgct aac         33

<210> SEQ ID NO 15
<211> LENGTH: 34
<212> TYPE: DNA
<213> ORGANISM: Artificial Sequence
<220> FEATURE:
<223> OTHER INFORMATION: tRNA KRR

<400> SEQUENCE: 15
gaacgaccgc gtctgattga ctcaccctgc cccg        34

<210> SEQ ID NO 16
<211> LENGTH: 34
<212> TYPE: DNA
<213> ORGANISM: Artificial Sequence
<220> FEATURE:
<223> OTHER INFORMATION: tRNA KRF

<400> SEQUENCE: 16
cggggcaggg tgagtcaatc agacgcggtc gttc        34

<210> SEQ ID NO 17
<211> LENGTH: 40
<212> TYPE: DNA
<213> ORGANISM: Artificial Sequence
<220> FEATURE:
<223> OTHER INFORMATION: tRNA ITR

<400> SEQUENCE: 17
ttgcataatt tgttttattg tcatcatgtt tattgcgtgg  40

<210> SEQ ID NO 18
<211> LENGTH: 40
<212> TYPE: DNA
<213> ORGANISM: Artificial Sequence
<220> FEATURE:
<223> OTHER INFORMATION: tRNA ITF

<400> SEQUENCE: 18
ccacgcaata aacatgatga caataaaaca aattatgcaa  40

<210> SEQ ID NO 19
<211> LENGTH: 36
<212> TYPE: DNA
<213> ORGANISM: Artificial Sequence
<220> FEATURE:
<223> OTHER INFORMATION: tRNA TRR

<400> SEQUENCE: 19
ccatttatgc cgggttttgg cagatttaca gtctgc      36

<210> SEQ ID NO 20
<211> LENGTH: 36
<212> TYPE: DNA
<213> ORGANISM: Artificial Sequence
<220> FEATURE:
<223> OTHER INFORMATION: tRNA TRF

<400> SEQUENCE: 20
gcagactgta aatctgccaa aacccggcat aaatgg      36

<210> SEQ ID NO 21
<211> LENGTH: 33
<212> TYPE: DNA
<213> ORGANISM: Artificial Sequence
<220> FEATURE:
<223> OTHER INFORMATION: tRNA RLR

<400> SEQUENCE: 21
atcaccagca aagccacgcg gctgtcaacg atc                                33

<210> SEQ ID NO 22
<211> LENGTH: 33
<212> TYPE: DNA
<213> ORGANISM: Artificial Sequence
<220> FEATURE:
<223> OTHER INFORMATION: tRNA RLF

<400> SEQUENCE: 22
gatcgttgac agccgcgtgg ctttgctggt gat                                33

<210> SEQ ID NO 23
<211> LENGTH: 32
<212> TYPE: DNA
<213> ORGANISM: Artificial Sequence
<220> FEATURE:
<223> OTHER INFORMATION: tRNA LNdeR
<220> FEATURE:
<221> NAME/KEY: misc_feature
<222> LOCATION: (1)..(6)
<223> OTHER INFORMATION: n is a, c, g, or t

<400> SEQUENCE: 23
nnnnnncata tgactccgga acgcgcctcc ac                                 32

<210> SEQ ID NO 24
<211> LENGTH: 5476
<212> TYPE: DNA
<213> ORGANISM: Artificial Sequence
<220> FEATURE:
<223> OTHER INFORMATION: RILYKT codon plasmid

<400> SEQUENCE: 24
gaattccgga tgagcattca tcaggcgggc aagaatgtga ataaaggccg gataaaactt     60
gtgcttattt ttctttacgg tctttaaaaa ggccgtaata tccagctgaa cggtctggtt    120
ataggtacat tgagcaactg actgaaatgc ctcaaaatgt tctttacgat gccattggga    180
tatatcaacg gtggtatatc cagtgatttt tttctccatt ttagcttcct tagctcctga    240
aaatctcgat aactcaaaaa atacgcccgg tagtgatctt atttcattat ggtgaaagtt    300
ggaacctctt acgtgccgat caacgtctca ttttcgccaa aagttgggcc agggcttccc    360
ggtatcaaca gggacaccag gatttattta ttctgcgaag tgatcttccg tcacaggtat    420
ttattcggcg caaagtgcgt cgggtgatgc tgccaactta ctgatttagt gtatgatggt    480
gtttttgagg tgctccagtg gcttctgttt ctatcagctg tccctcctgt tcagctactg    540
acggggtggt gcgtaacggc aaaagcaccg ccggacatca gcgctagcgg agtgtatact    600
ggcttactat gttggcactg atgagggtgt cagtgaagtg cttcatgtgg caggagaaaa    660
aaggctgcac cggtgcgtca gcagaatatg tgatacagga tatattccgc ttccctcgc     720 tcactgactc gctacgctcg gtcgttcgac tgcggcgagc ggaaatggct tacgaacggg    780
gcggagattt cctggaagat gccaggaaga tacttaacag ggaagtgaga gggccgcggc    840
aaagccgttt ttccataggc tccgcccccc tgacaagcat cacgaaatct gacgctcaaa    900

```
tcagtggtgg cgaaacccga caggactata aagataccag gcgttttccc ctggcggctc      960
cctcgtgcgc tctcctgttc ctgcctttcg gtttaccggt gtcattccgc tgttatggcc     1020
gcgtttgtct cattccacgc ctgacactca gttccgggta ggcagttcgc tccaagctgg     1080
actgtatgca cgaaccccc gttcagtccg accgctgcgc cttatccggt aactatcgtc      1140
ttgagtccaa cccggaaaga catgcaaaag caccactggc agcagccact ggtaattgat     1200
ttagaggagt tagtcttgaa gtcatgcgcc ggttaaggct aaactgaaag dacaagtttt     1260
ggtgactgcg ctcctccaag ccagttacct cggttcaaag agttggtagc tcagagaacc     1320
ttcgaaaaac cgccctgcaa gcggttttt tcgttttcag agcaagagat tacgcgcaga      1380
ccaaaacgat ctcaagaaga tcatcttatt aatcagataa atatttcta gatttcagtg      1440 caatttatct cttcaaatgt agcacctgaa gtcagcccca tacgatataa gttgtaattc     1500
tcatgtttga cagcttatca tcgataagct ttaatgcggt agtttatcac agttaaattg     1560
ctaacgcagt caggcaccgt gtatgaaatc taacaatgcg ctcatcgtca tcctcggcac     1620
cgtcaccctg gatgctgtac aattgacgac gacaagggcc cgggcaaact agtaatcaga     1680
cgcggtcgtt cacttgttca gcaaccagat caaaagccat tgactcagca agggttgacc     1740
gtataattca cgcgattaca ccgcattgcg gtatcaacgc gcccttagct cagttggata     1800
gagcaacgac cttctaagtc gtgggccgca ggttcgaatc ctgcagggcg cgccattaca     1860
attcaatcag ttacgccttc tttatatcct ccagccatgg ccttgaaatg gcgttagtca     1920
tgaaatatag accgccatcg agtaccccctt gtacccttaa ctcttcctga tacgtaaata    1980
atgatttggt ggcccttgct ggacttgaac cagcgaccaa gcgattatga gtcgcctgct    2040
ctaaccactg agctaaaggg ccttgagtgt gcaataacaa tactataaa ccacgcaata     2100 aacatgatga tctagagaat cccgtcgtag ccaccatctt tttttgcggg agtggcgaaa    2160
ttggtagacg caccagattt aggttctggc gccgctaggt gtgcgagttc aagtctcgcc    2220
tcccgcacca ttcaccagaa agcgttgatc ggatgccctc gagccttccc cgcatgggca    2280
gaatatttaa ttgcggattc gttgggaagt tcagggactt ttgaaagtga tggtggtggg    2340
ggaaggattc gaaccttcga agtcgatgac ggcagattta cagtctgctc cctttggccg    2400
ctcgggaacc ccaccagggg taattcaaat tttgaggtaa tgcttgagat ggtggtgggg    2460
gaaggattat tcgtcgcttc gctcctcacc cttcgggccg ttgcctgtgg caacgttctc    2520
tcgctttcgc tcgaatcgaa ccttagtcga aggttctcac ccttccccga tgagtgcaaa    2580 cttcacaat ctcaccgaag ttaccacatc gctgtggtga attatggtgg tggcacggcg     2640
ggtgctaacg tccgtcgtga agagggaaac aacccagacc gccagctaag gtcccaaagt    2700
catggttaag tgggaaacga tgtgggaagg cccagacagc caggatgttg gcttagaagc    2760
agccatcatt taaagaaagc gtaatagctc actggtcgag tcggcctgcg cggaagatgt    2820 aacgggcta aaccatgcac cgaagctgcg gcagcgacgc ttatgcgttg ttgggtaggg     2880
gagcgttctg taagcctgcg aaggtgtgct gtgaggcatg ctggaggtat cagaagtgcg    2940
aatgctgaca taagtaacga taaagcgggt gaaaagcccg ctcgccggaa gaccaagggt    3000
tcctgtccaa cgttaatcgg ggcagggtga gtcaatcaga cgcggtcgtt cacttgttca    3060
gcaaccagat caaaagccat tgactcagca agggttgacc gtataattca cgcgattaca    3120
ccgcattgcg gtatcaacgc gcccttagct cagttggata gagcaacgac cttctaagtc    3180
gtgggccgca ggttcgaatc ctgcagggcg cgccattaca attcaatcag ttacgccttc    3240
```

```
tttatatcct ccagccatgg ccttgaaatg gcgttagtca tgaaatatag accgccatcg   3300
agtaccccTT gtacccttaa ctcttcctga tacgtaaata atgatttggt ggcccttgct   3360
ggacttgaac cagcgaccaa gcgattatga gtcgcctgct ctaaccactg agctaaaggg   3420
ccttgagtgt gcaataacaa tactataaa ccacgcaata aacatgatga caataaaaca    3480
aattatgcaa tttttagtt gcatgaactc gcatgtctcc atagaatgcg cgctacttga    3540
tgccgactta gctcagtagg tagagcaact gacttgtaat cagtaggtca ccagttcgat   3600
tccggtagtc ggcaccatca agtccggtgg ggttcccgag cggccaaagg gagcagactg   3660
taaatctgcc aaaacccggc ataaatggcg agggtttaag caatcgagcg gcagcgtact   3720
taccccgcac tccattagcg ggtatactca tgccgcattg tcctcttagt taaatggata   3780
taacgagccc ctcctaaggg ctaattgcag gttcgattcc tgcaggggac accatttatc   3840
agttcgctcc catccgtacc agtccgcaaa atccctgaa tatcaagcat tccgtagatt    3900
tacagttcgt catggttcgc ttcagatcgt tgacagccgc gtggctttgc tggtgattaa   3960
aaattaagga gggtgtaacg acaagttgca ggcacaaaaa aaccacccga aggtgggttc   4020
acgacactgc ttattgcttt gatttattc ttatctttcc catggtaccc ggagcgggac    4080
ttgaacccgc acagcgcgaa cgccgaggga ttttaaatcc cttgtgtcta ccgattccac   4140
catccgggct cgggaagaaa gtggaggcgc gttccggagt catatgatcg tgctcctgtc   4200
gttgaggacc cggctaggct ggcggggttg ccttactggt tagcagaatg aaatcaccga   4260
tacgcgagcg aacgtgaagc gactgctgct gcaaaacgtc tgcgacctga gcaacaacat   4320
gaatggtctt cggtttccgt gtttcgtaaa gtctggaaac gcggaagtcc cctacgtgct   4380
gctgaagttg cccgcaacag agagtggaac caaccggtga taccacgata ctatgactga   4440
gagtcaacgc catgagcggc ctcatttctt attctgagtt acaacagtcc gcaccgctgc   4500
cggtagctcc ttccggtggg cgcggggcat gactatcgtc gccgcactta tgactgtctt   4560
ctttatcatg caactcgtag acaggtgcc ggcagcgccc aacagtcccc cggccacggg    4620
gcctgccacc atacccacgc cgaaacaagc gccctgcacc attatgttcc ggatctgcat   4680
cgcaggatgc tgctggctac cctgtggaac acctacatct gtattaacga agcgctaacc   4740
gtttttatca ggctctggga ggcagaataa atgatcatat cgtcaattat tacctccacg   4800
gggagagcct gagcaaactg gcctcaggca tttgagaagc acacggtcac actgcttccg   4860
gtagtcaata aaccggtaaa ccagcaatag acataagcgg ctatttaacg accctgccct   4920
gaaccgacga ccgggtcgaa tttgctttcg aatttctgcc attcatccgc ttattatcac   4980
ttattcaggc gtagcaacca ggcgtttaag ggcaccaata actgccttaa aaaaattacg   5040
ccccgccctg ccactcatcg cagtactgtt gtaattcatt aagcattctg ccgacatgga   5100
agccatcaca aacggcatga tgaacctgaa tcgccagcgg catcagcacc ttgtcgcctt   5160
gcgtataata tttgcccatg gtgaaaacgg gggcgaagaa gttgtccata ttggccacgt   5220
ttaaatcaaa actggtgaaa ctcacccagg gattggctga gacgaaaaac atattctcaa   5280
taaacccttt agggaaatag gccaggtttt caccgtaaca cgccacatct gcgaatata    5340
tgtgtagaaa ctgccggaaa tcgtcgtggt attcactcca gagcgatgaa aacgtttcag   5400
tttgctcatg gaaaacggtg taacaagggt gaacactatc ccatatcacc agctcaccgt   5460
ctttcattgc catacg                                                   5476
```

<210> SEQ ID NO 25
<211> LENGTH: 33

```
<212> TYPE: DNA
<213> ORGANISM: Artificial Sequence
<220> FEATURE:
<223> OTHER INFORMATION: A523RF

<400> SEQUENCE: 25
ataaatgcta agcaaagagt attgaaaata ata                                    33

<210> SEQ ID NO 26
<211> LENGTH: 33
<212> TYPE: DNA
<213> ORGANISM: Artificial Sequence
<220> FEATURE:
<223> OTHER INFORMATION: A523RR

<400> SEQUENCE: 26
tattattttc aatactcttt gcttagcatt tat                                    33

<210> SEQ ID NO 27
<211> LENGTH: 33
<212> TYPE: DNA
<213> ORGANISM: Artificial Sequence
<220> FEATURE:
<223> OTHER INFORMATION: N540RF

<400> SEQUENCE: 27
tatatgggtt tcccaagagc gagatgggat tgc                                    33

<210> SEQ ID NO 28
<211> LENGTH: 33
<212> TYPE: DNA
<213> ORGANISM: Artificial Sequence
<220> FEATURE:
<223> OTHER INFORMATION: N540RR

<400> SEQUENCE: 28
gcaatcccat ctcgctcttg ggaaacccat ata                                    33

<210> SEQ ID NO 29
<211> LENGTH: 33
<212> TYPE: DNA
<213> ORGANISM: Artificial Sequence
<220> FEATURE:
<223> OTHER INFORMATION: S185DF

<400> SEQUENCE: 29
gatatagaag tttacgatga ggctttccct aat                                    33

<210> SEQ ID NO 30
<211> LENGTH: 33
<212> TYPE: DNA
<213> ORGANISM: Artificial Sequence
<220> FEATURE:
<223> OTHER INFORMATION: S185DR

<400> SEQUENCE: 30
attagggaaa gcctcatcgt aaacttctat atc                                    33

<210> SEQ ID NO 31
<211> LENGTH: 2808
<212> TYPE: DNA
<213> ORGANISM: Artificial Sequence
<220> FEATURE:
<223> OTHER INFORMATION: Neq HS M1 DNA polymerase

<400> SEQUENCE: 31
```

```
atgttacacc aactccccac gatggttgta gaagaaaagg cggtaaaaga ggaagaaggg      60
tatagcgtgc taaaatgtta ttggattaat atagagaaca cccctttaga cgaggtaatt     120
ttaataggta aagacgaaaa taatagagct tgtgaagtta taattccata caaatggtat     180
ttctattttg aaggcgatat aaaggattta gaagaattcg ctaacaacaa aaaaataaaa     240
atcgaatata caaaggagca aaagaaatat atagaaaaac caaagatgt ttataaagta      300
tatgttttgc ataacatta tccaatacta aagaattca ttaaagaaaa gggctataaa       360
aaatacgaaa ccgatataaa tgtttatagg aagttttta tagataaagg gatagagcct      420
tttgaatggt ttgaggtaga aggcaaaatt ttattatcta cctctaacaa agttagaata     480
aaagcacaaa gtataaaaag attgtatgaa aagactaagc catcggtttt agcttttgat     540
atagaagttt acagtgaggc tttccctaat cctgaaaaag acaaaataat atctatagcc     600
ctttatggag acaattacga aggggttatc tcttacaaag gagaaccaac tataaaagtt     660
aataccgaat atgaattaat tgagaaattt gtcgaaataa tagaaagctt aaaaccagac     720
ataatagtta catacaatgg ggataatttc gatatagact ttttagtgaa aagggcttct     780
ttatacaata taaggctacc aataaaattg gttaacaaaa aagagcctac ttataatttt     840
agggaaagcg cacatgtaga tttgtataaa acaattacta ccatatataa aacccaattg     900
tctacccaaa catattcatt aaatgaagta gctaaagaaa tcttggaga ggagaaaatt      960
tatgattatg aaaacatgtt atatgattgg gccataggca attataacaa agtgttcgaa    1020
tacaatttaa aagatgccga attaacatat aagctattca atactatga aaatgattta     1080
ttggaattag caagattggt taaccaacca ttatttgatg tatctaggtt tagctatagt    1140
aatatagttg aatggtatct aatcaaaaaa agcagaaaat ataatgaaat tgtgcctaac    1200
aaaccaaaaa tggaagaagt agagagaaga aaattaaata cctatgcagg agcattcgtt    1260
tacgaaccaa aacccggttt gtatgagaat ttagctgtac tggatttcgc ttctctgtat    1320
ccttcaatta tattagagca taatgttttct ccaggcacaa tatattgtga gcatgatgat   1380
tgtaaacaaa atggggtaga agcgataata aataatgaga aaaaatatgt gtggttttgc    1440
aaaaaagtaa aagggtttat tccaacggta ttagagcatt tgtatacaaa aaggctagaa    1500
cttaagagaa aactgaaaga actagatagg gatagtgaag aatataaaat tataaatgct    1560
aagcaaagag tattgaaaat aataattaat gcaacctatg gctatatggg tttcccaaat    1620
gcgagatggt attgcataga ctgtgctgcg gcagtagcag cttggggcag gaaatacatt    1680
aattatatat taaaagggc cgaagaagaa ggattcaaag taatttatgg agattctata    1740
atggatactg aaatagaggt tatagaaaat ggtataaaaa agaaagaaaa gctaagcgat    1800
ttgtttaaca aatactatgc cggttttcaa ataggggaga acattatgc tttccctcca     1860
gatttgtatg tatatgatgg agaaagatgg gttaaagtat attcaataat aaaacatgaa    1920
accgagaccg atttatatga aataaatggg ataacattaa gtgcaaacca tttagtttta    1980
agcaaaggca attgggttaa agccaaggaa tatgaaaata aaaataatca ccatcaccat    2040
caccacatgc gctatcttgg caaaaagaga gttattttat atgatttatc tactgaatcg    2100
ggtaaatttt atgttaatgg gctagtttta cacaataccg attcattatt catttctggg    2160
gacaaagaca agtattagaa attttagag aaagtaaata agaattacc cggtaaaata     2220
caattagatt tagaagattt ctatgttaga gggatattcg taaaaagag gggtgaacaa    2280
aagggggcaa aaagaaata tgctttatta agcgaacaag gttacataaa gctaggggc     2340
ttcgaagcag taagaacaga ctgggctccc atagttaaag aagtccaaac aaagctattg    2400
```

-continued

```
gaaattttgc taaagaagg  taacatagaa  aaagcaagac  aatacataaa  agaaattatt  2460
agaaagctaa gaatagaga  ataccatgg   gagaagcttt  taattacaga  aacgataaga  2520
aagcctttag aaaatacaa  agttgaagct  cctcatgtgg  cagcagcaaa  aaatataaa   2580 aggttgggct ataagttat  gcctggcttt  agagttagat  atttagtggt  aggtagcact  2640
ggaagggttt cagatagaat taaaatagac  aaagaagtta  ggggtaatga  atatgacccc  2700
gaatactaca tagaaaaaca actattgcct  gcagtagagc  aaatattaga  atctgtaggt  2760
attaaagaca cattcacagg caaaaaacta acagatttct  ttaaatga                 2808
```

<210> SEQ ID NO 32
<211> LENGTH: 935
<212> TYPE: PRT
<213> ORGANISM: Artificial Sequence
<220> FEATURE:
<223> OTHER INFORMATION: Neq HS M1 DNA polymerase

<400> SEQUENCE: 32

```
Met Leu His Gln Leu Pro Thr Met Val Val Glu Lys Ala Val Lys
1               5                   10                  15

Glu Glu Glu Gly Tyr Ser Val Leu Lys Cys Tyr Trp Ile Asn Ile Glu
            20                  25                  30

Asn Thr Pro Leu Asp Glu Val Ile Leu Ile Gly Lys Asp Glu Asn Asn
        35                  40                  45

Arg Ala Cys Glu Val Ile Ile Pro Tyr Lys Trp Tyr Phe Tyr Phe Glu
    50                  55                  60

Gly Asp Ile Lys Asp Leu Glu Glu Phe Ala Asn Asn Lys Lys Ile Lys
65                  70                  75                  80

Ile Glu Tyr Thr Lys Glu Gln Lys Lys Tyr Ile Glu Lys Pro Lys Asp
                85                  90                  95

Val Tyr Lys Val Tyr Val Leu His Lys His Tyr Pro Ile Leu Lys Glu
            100                 105                 110

Phe Ile Lys Glu Lys Gly Tyr Lys Lys Tyr Glu Thr Asp Ile Asn Val
        115                 120                 125

Tyr Arg Lys Phe Leu Ile Asp Lys Gly Ile Glu Pro Phe Glu Trp Phe
    130                 135                 140

Glu Val Glu Gly Lys Ile Leu Leu Ser Thr Ser Asn Lys Val Arg Ile
145                 150                 155                 160

Lys Ala Gln Ser Ile Lys Arg Leu Tyr Glu Lys Thr Lys Pro Ser Val
                165                 170                 175

Leu Ala Phe Asp Ile Glu Val Tyr Ser Glu Ala Phe Pro Pro Asn Glu
            180                 185                 190

Lys Asp Lys Ile Ile Ser Ile Ala Leu Tyr Gly Asp Asn Tyr Glu Gly
        195                 200                 205

Val Ile Ser Tyr Lys Gly Glu Pro Thr Ile Lys Val Asn Thr Glu Tyr
    210                 215                 220

Glu Leu Ile Glu Lys Phe Val Glu Ile Ile Glu Ser Leu Lys Pro Asp
225                 230                 235                 240

Ile Ile Val Thr Tyr Asn Gly Asp Asn Phe Asp Ile Asp Phe Leu Val
                245                 250                 255

Lys Arg Ala Ser Leu Tyr Asn Ile Arg Leu Pro Ile Lys Leu Val Asn
            260                 265                 270

Lys Lys Glu Pro Thr Tyr Asn Phe Arg Glu Ser Ala His Val Asp Leu
        275                 280                 285
```

```
Tyr Lys Thr Ile Thr Thr Ile Tyr Lys Thr Gln Leu Ser Thr Gln Thr
        290                 295                 300

Tyr Ser Leu Asn Glu Val Ala Lys Glu Ile Leu Gly Glu Glu Lys Ile
305                 310                 315                 320

Tyr Asp Tyr Glu Asn Met Leu Tyr Asp Trp Ala Ile Gly Asn Tyr Asn
                325                 330                 335

Lys Val Phe Glu Tyr Asn Leu Lys Asp Ala Glu Leu Thr Tyr Lys Leu
            340                 345                 350

Phe Lys Tyr Tyr Glu Asn Asp Leu Glu Leu Ala Arg Leu Val Asn
        355                 360                 365

Gln Pro Leu Phe Asp Val Ser Arg Phe Ser Tyr Ser Asn Ile Val Glu
370                 375                 380

Trp Tyr Leu Ile Lys Lys Ser Arg Lys Tyr Asn Glu Ile Val Pro Asn
385                 390                 395                 400

Lys Pro Lys Met Glu Glu Val Glu Arg Arg Lys Leu Asn Thr Tyr Ala
                405                 410                 415

Gly Ala Phe Val Tyr Glu Pro Lys Pro Gly Leu Tyr Glu Asn Leu Ala
            420                 425                 430

Val Leu Asp Phe Ala Ser Leu Tyr Pro Ser Ile Ile Leu Glu His Asn
        435                 440                 445

Val Ser Pro Gly Thr Ile Tyr Cys Glu His Asp Asp Cys Lys Gln Asn
450                 455                 460

Gly Val Glu Ala Ile Ile Asn Asn Glu Lys Lys Tyr Val Trp Phe Cys
465                 470                 475                 480

Lys Lys Val Lys Gly Phe Ile Pro Thr Val Leu Glu His Leu Tyr Thr
                485                 490                 495

Lys Arg Leu Glu Leu Lys Arg Lys Leu Lys Glu Leu Asp Arg Asp Ser
            500                 505                 510

Glu Glu Tyr Lys Ile Ile Asn Ala Lys Gln Arg Val Leu Lys Ile Ile
        515                 520                 525

Ile Asn Ala Thr Tyr Gly Tyr Met Gly Phe Pro Asn Ala Arg Trp Tyr
530                 535                 540

Cys Ile Asp Cys Ala Ala Ala Val Ala Ala Trp Gly Arg Lys Tyr Ile
545                 550                 555                 560

Asn Tyr Ile Leu Lys Arg Ala Glu Glu Glu Gly Phe Lys Val Ile Tyr
                565                 570                 575

Gly Asp Ser Ile Met Asp Thr Glu Ile Glu Val Ile Glu Asn Gly Ile
            580                 585                 590

Lys Lys Lys Glu Lys Leu Ser Asp Leu Phe Asn Lys Tyr Tyr Ala Gly
        595                 600                 605

Phe Gln Ile Gly Glu Lys His Tyr Ala Phe Pro Pro Asp Leu Tyr Val
610                 615                 620

Tyr Asp Gly Glu Arg Trp Val Lys Val Tyr Ser Ile Ile Lys His Glu
625                 630                 635                 640

Thr Glu Thr Asp Leu Tyr Glu Ile Asn Gly Ile Thr Leu Ser Ala Asn
                645                 650                 655

His Leu Val Leu Ser Lys Gly Asn Trp Val Lys Ala Lys Glu Tyr Glu
            660                 665                 670

Asn Lys Asn Asn His His His His His Met Arg Tyr Leu Gly Lys
        675                 680                 685

Lys Arg Val Ile Leu Tyr Asp Leu Ser Thr Glu Ser Gly Lys Phe Tyr
690                 695                 700

Val Asn Gly Leu Val Leu His Asn Thr Asp Ser Leu Phe Ile Ser Gly
```

Asp Lys Asp Lys Val Leu Glu Phe Leu Glu Lys Val Asn Lys Glu Leu
705                 710                 715                 720
                725                 730                 735

Pro Gly Lys Ile Gln Leu Asp Leu Glu Asp Phe Tyr Val Arg Gly Ile
                740                 745                 750

Phe Val Lys Arg Gly Glu Gln Gly Ala Lys Lys Tyr Ala
                755                 760                 765

Leu Leu Ser Glu Gln Gly Tyr Ile Lys Leu Arg Gly Phe Glu Ala Val
770                 775                 780

Arg Thr Asp Trp Ala Pro Ile Val Lys Glu Val Gln Thr Lys Leu Leu
785                 790                 795                 800

Glu Ile Leu Leu Lys Glu Gly Asn Ile Glu Lys Ala Arg Gln Tyr Ile
                805                 810                 815

Lys Glu Ile Ile Arg Lys Leu Arg Asn Arg Glu Ile Pro Trp Glu Lys
                820                 825                 830

Leu Leu Ile Thr Glu Thr Ile Arg Lys Pro Leu Glu Lys Tyr Lys Val
                835                 840                 845

Glu Ala Pro His Val Ala Ala Ala Lys Lys Tyr Lys Arg Leu Gly Tyr
850                 855                 860

Lys Val Met Pro Gly Phe Arg Val Arg Tyr Leu Val Val Gly Ser Thr
865                 870                 875                 880

Gly Arg Val Ser Asp Arg Ile Lys Ile Asp Lys Glu Val Arg Gly Asn
                885                 890                 895

Glu Tyr Asp Pro Glu Tyr Tyr Ile Glu Lys Gln Leu Leu Pro Ala Val
                900                 905                 910

Glu Gln Ile Leu Glu Ser Val Gly Ile Lys Asp Thr Phe Thr Gly Lys
                915                 920                 925

Lys Leu Thr Asp Phe Phe Lys
                930                 935

<210> SEQ ID NO 33
<211> LENGTH: 2808
<212> TYPE: DNA
<213> ORGANISM: Artificial Sequence
<220> FEATURE:
<223> OTHER INFORMATION: Neq HS M2 DNA polymerase

<400> SEQUENCE: 33

```
atgttacacc aactccccac gatggttgta aagaaaaagg cggtaaaaga ggaagaaggg    60
tatagcgtgc taaatgttat ttggattaat atagagaaca ccccctttaga cgaggtaatt  120
ttaataggta agacgaaaa taatagagct tgtgaagtta taattccata caaatggtat   180
ttctattttg aaggcgatat aaaggattta gaagaattcg ctaacaacaa aaaaataaaa   240
atcgaatata caaaggagca aagaaatat atagaaaaac aaaagatgt ttataaagta    300
tatgttttgc ataacatta tccaatacta aagaattca ttaagaaaa gggctataaa     360
aaatacgaaa ccgatataaa tgtttatagg aagtttttaa tagataaagg atagagcct    420
tttgaatggt ttgaggtaga aggcaaaatt ttattatcta cctctaacaa agttagaata   480
aaagcacaaa gtaaaaaag attgtatgaa aagactaagc catcggtttt agcttttgat   540
atagaagttt acagtgaggc tttccctaat cctgaaaaag acaaaataat atctatagcc   600
ctttatggag acaattacga agggttatc tcttacaaag gagaaccaac tataaaagtt    660
aataccgaat atgaattaat tgagaaattt gtcgaaataa tagaaagctt aaaaccagac   720
ataatagtta catacaatgg ggataatttc gatatagact ttttagtgaa aagggcttct   780
```

```
ttatacaata taaggctacc aataaaattg gttaacaaaa aagagcctac ttataatttt      840
agggaaagcg cacatgtaga tttgtataaa acaattacta ccatatataa aacccaattg      900
tctacccaaa catattcatt aaatgaagta gctaaagaaa ttcttggaga ggagaaaatt      960
tatgattatg aaaacatgtt atatgattgg gccataggca attataacaa agtgttcgaa     1020
tacaatttaa aagatgccga attaacatat aagctattca aatactatga aaatgattta     1080
ttggaattag caagattggt taaccaacca ttatttgatg tatctaggtt tagctatagt     1140
aatatagttg aatggtatct aatcaaaaaa agcagaaaat aaatgaaat tgtgcctaac      1200 aaaccaaaaa tggaagaagt agagagaaga aaattaaata cctatgcagg agcattcgtt     1260
tacgaaccaa aacccggttt gtatgagaat ttagctgtac tggatttcgc ttctctgtat     1320
ccttcaatta tattagagca taatgttct ccaggcacaa tatattgtga gcatgatgat      1380
tgtaaacaaa atggggtaga agcgataata aataatgaga aaaaatatgt gtggttttgc     1440
aaaaaagtaa aagggtttat tccaacggta ttagagcatt tgtatacaaa aaggctagaa     1500
cttaagagaa aactgaaaga actagatagg gatagtgaag aatataaaat tataaatgct     1560
aagcaaagag tattgaaaat aataattaat gcaacctatg gctatatggg tttcccaaga     1620
gcgagatggt attgcataga ctgtgctgcg gcagtagcag cttggggcag gaaatacatt     1680
aattatatat taaaagggc cgaagaagaa ggattcaaag taatttatgg agattctata     1740
atggatactg aaatagaggt tatagaaaat ggtataaaaa agaaagaaaa gctaagcgat     1800
ttgtttaaca aatactatgc cggttttcaa atagggagga aacattatgc tttccctcca     1860
gatttgtatg tatatgatgg agaaagatgg gttaaagtat attcaataat aaaacatgaa     1920
accgagaccg atttatatga aataaatggg ataacattaa gtgcaaacca tttagtttta     1980
agcaaaggca attgggttaa agccaaggaa tatgaaaata aaaataatca ccatcaccat     2040
caccacatgc gctatcttgg caaaagagaa gttattttat atgatttatc tactgaatcg     2100
ggtaaatttt atgttaatgg gctagtttta cacaataccg attcattatt catttctggg     2160
gacaaagaca aagtattaga atttttagag aaagtaaata aagaattacc cggtaaaata     2220
caattagatt tagaagattt ctatgttaga gggatattcg taaaaagag gggtgaacaa     2280 aaggggcaa aaaagaaata tgctttatta agcgaacaag gttacataaa gctaaggggc     2340
ttcgaagcag taagaacaga ctgggctccc atagttaaag aagtccaaac aaagctattg     2400
gaaattttgc taaagaagg taacatagaa aaagcaagac aatacataaa agaaattatt     2460
agaaagctaa gaaatagaga aataccatgg gagaagcttt taattacaga aacgataaga     2520
aagcctttag aaaatacaa agttgaagct cctcatgtgg cagcagcaaa aaaatataaa     2580
aggttgggct ataagttat gcctggcttt agagttagat atttagtggt aggtagcact     2640
ggaagggttt cagatagaat taaaatagac aaagaagtta ggggtaatga atatgacccc     2700
gaatactaca tagaaaaaca actattgcct gcagtagagc aaatattaga atctgtaggt     2760
attaaagaca cattcacagg caaaaaacta acagatttct ttaaatga                 2808
```

<210> SEQ ID NO 34
<211> LENGTH: 935
<212> TYPE: PRT
<213> ORGANISM: Artificial Sequence
<220> FEATURE:
<223> OTHER INFORMATION: Neq HS M2 DNA polymerase

<400> SEQUENCE: 34

```
Met Leu His Gln Leu Pro Thr Met Val Val Glu Glu Lys Ala Val Lys
1               5                   10                  15
Glu Glu Glu Gly Tyr Ser Val Leu Lys Cys Tyr Trp Ile Asn Ile Glu
            20                  25                  30
Asn Thr Pro Leu Asp Glu Val Ile Leu Ile Gly Lys Asp Glu Asn Asn
            35                  40                  45
Arg Ala Cys Glu Val Ile Ile Pro Tyr Lys Trp Tyr Phe Tyr Phe Glu
    50                  55                  60
Gly Asp Ile Lys Asp Leu Glu Glu Phe Ala Asn Asn Lys Lys Ile Lys
65                  70                  75                  80
Ile Glu Tyr Thr Lys Glu Gln Lys Lys Tyr Ile Glu Lys Pro Lys Asp
                85                  90                  95
Val Tyr Lys Val Tyr Val Leu His Lys His Tyr Pro Ile Leu Lys Glu
            100                 105                 110
Phe Ile Lys Glu Lys Gly Tyr Lys Lys Tyr Glu Thr Asp Ile Asn Val
            115                 120                 125
Tyr Arg Lys Phe Leu Ile Asp Lys Gly Ile Glu Pro Phe Glu Trp Phe
    130                 135                 140
Glu Val Glu Gly Lys Ile Leu Leu Ser Thr Ser Asn Lys Val Arg Ile
145                 150                 155                 160
Lys Ala Gln Ser Ile Lys Arg Leu Tyr Glu Lys Thr Lys Pro Ser Val
                165                 170                 175
Leu Ala Phe Asp Ile Glu Val Tyr Ser Glu Ala Phe Pro Asn Pro Glu
            180                 185                 190
Lys Asp Lys Ile Ile Ser Ile Ala Leu Tyr Gly Asp Asn Tyr Glu Gly
            195                 200                 205
Val Ile Ser Tyr Lys Gly Glu Pro Thr Ile Lys Val Asn Thr Glu Tyr
    210                 215                 220
Glu Leu Ile Glu Lys Phe Val Glu Ile Ile Glu Ser Leu Lys Pro Asp
225                 230                 235                 240
Ile Ile Val Thr Tyr Asn Gly Asp Asn Phe Asp Ile Asp Phe Leu Val
                245                 250                 255
Lys Arg Ala Ser Leu Tyr Asn Ile Arg Leu Pro Ile Lys Leu Val Asn
            260                 265                 270
Lys Lys Glu Pro Thr Tyr Asn Phe Arg Glu Ser Ala His Val Asp Leu
            275                 280                 285
Tyr Lys Thr Ile Thr Thr Ile Tyr Lys Thr Gln Leu Ser Thr Gln Thr
    290                 295                 300
Tyr Ser Leu Asn Glu Val Ala Lys Glu Ile Leu Gly Glu Glu Lys Ile
305                 310                 315                 320
Tyr Asp Tyr Glu Asn Met Leu Tyr Asp Trp Ala Ile Gly Asn Tyr Asn
                325                 330                 335
Lys Val Phe Glu Tyr Asn Leu Lys Asp Ala Glu Leu Thr Tyr Lys Leu
            340                 345                 350
Phe Lys Tyr Tyr Glu Asn Asp Leu Leu Glu Leu Ala Arg Leu Val Asn
    355                 360                 365
Gln Pro Leu Phe Asp Val Ser Arg Phe Ser Tyr Ser Asn Ile Val Glu
    370                 375                 380
Trp Tyr Leu Ile Lys Lys Ser Arg Lys Tyr Asn Glu Ile Val Pro Asn
385                 390                 395                 400
Lys Pro Lys Met Glu Glu Val Glu Arg Arg Lys Leu Asn Thr Tyr Ala
                405                 410                 415
Gly Ala Phe Val Tyr Glu Pro Lys Pro Gly Leu Tyr Glu Asn Leu Ala
```

```
                420             425             430
Val Leu Asp Phe Ala Ser Leu Tyr Pro Ser Ile Ile Leu Glu His Asn
            435                 440                 445
Val Ser Pro Gly Thr Ile Tyr Cys Glu His Asp Asp Cys Lys Gln Asn
        450                 455                 460
Gly Val Glu Ala Ile Ile Asn Asn Glu Lys Lys Tyr Val Trp Phe Cys
465                 470                 475                 480
Lys Lys Val Lys Gly Phe Ile Pro Thr Val Leu Glu His Leu Tyr Thr
                485                 490                 495
Lys Arg Leu Glu Leu Lys Arg Lys Leu Lys Glu Leu Asp Arg Asp Ser
            500                 505                 510
Glu Glu Tyr Lys Ile Ile Asn Ala Lys Gln Arg Val Leu Lys Ile Ile
        515                 520                 525
Ile Asn Ala Thr Tyr Gly Tyr Met Gly Phe Pro Arg Ala Arg Trp Tyr
        530                 535                 540
Cys Ile Asp Cys Ala Ala Ala Val Ala Ala Trp Gly Arg Lys Tyr Ile
545                 550                 555                 560
Asn Tyr Ile Leu Lys Arg Ala Glu Glu Gly Phe Lys Val Ile Tyr
                565                 570                 575
Gly Asp Ser Ile Met Asp Thr Glu Ile Glu Val Ile Glu Asn Gly Ile
            580                 585                 590
Lys Lys Lys Glu Lys Leu Ser Asp Leu Phe Asn Lys Tyr Tyr Ala Gly
            595                 600                 605
Phe Gln Ile Gly Glu Lys His Tyr Ala Phe Pro Pro Asp Leu Tyr Val
        610                 615                 620
Tyr Asp Gly Glu Arg Trp Val Lys Val Tyr Ser Ile Ile Lys His Glu
625                 630                 635                 640
Thr Glu Thr Asp Leu Tyr Glu Ile Asn Gly Ile Thr Leu Ser Ala Asn
                645                 650                 655
His Leu Val Leu Ser Lys Gly Asn Trp Val Lys Ala Lys Glu Tyr Glu
            660                 665                 670
Asn Lys Asn Asn His His His His His Met Arg Tyr Leu Gly Lys
        675                 680                 685
Lys Arg Val Ile Leu Tyr Asp Leu Ser Thr Glu Ser Gly Lys Phe Tyr
        690                 695                 700
Val Asn Gly Leu Val Leu His Asn Thr Asp Ser Leu Phe Ile Ser Gly
705                 710                 715                 720
Asp Lys Asp Lys Val Leu Glu Phe Leu Glu Lys Val Asn Lys Glu Leu
                725                 730                 735
Pro Gly Lys Ile Gln Leu Asp Leu Glu Asp Phe Tyr Val Arg Gly Ile
            740                 745                 750
Phe Val Lys Arg Gly Glu Gln Lys Gly Ala Lys Lys Tyr Ala
            755                 760                 765
Leu Leu Ser Glu Gln Gly Tyr Ile Lys Leu Arg Gly Phe Glu Ala Val
        770                 775                 780
Arg Thr Asp Trp Ala Pro Ile Val Lys Glu Val Gln Thr Lys Leu Leu
785                 790                 795                 800
Glu Ile Leu Leu Lys Glu Gly Asn Ile Glu Lys Ala Arg Gln Tyr Ile
                805                 810                 815
Lys Glu Ile Ile Arg Lys Leu Arg Asn Arg Glu Ile Pro Trp Glu Lys
            820                 825                 830
Leu Leu Ile Thr Glu Thr Ile Arg Lys Pro Leu Glu Lys Tyr Lys Val
            835                 840                 845
```

Glu Ala Pro His Val Ala Ala Lys Lys Tyr Lys Arg Leu Gly Tyr
        850                 855                 860

Lys Val Met Pro Gly Phe Arg Val Arg Tyr Leu Val Val Gly Ser Thr
865                 870                 875                 880

Gly Arg Val Ser Asp Arg Ile Lys Ile Asp Lys Glu Val Arg Gly Asn
                885                 890                 895

Glu Tyr Asp Pro Glu Tyr Tyr Ile Glu Lys Gln Leu Leu Pro Ala Val
                900                 905                 910

Glu Gln Ile Leu Glu Ser Val Gly Ile Lys Asp Thr Phe Thr Gly Lys
        915                 920                 925

Lys Leu Thr Asp Phe Phe Lys
        930                 935

<210> SEQ ID NO 35
<211> LENGTH: 2808
<212> TYPE: DNA
<213> ORGANISM: Artificial Sequence
<220> FEATURE:
<223> OTHER INFORMATION: Neq HS M3 DNA polymerase

<400> SEQUENCE: 35

```
atgttacacc aactccccac gatggttgta gaagaaaagg cggtaaaaga ggaagaaggg      60
tatagcgtgc taaaatgtta ttggattaat atagagaaca ccccctttaga cgaggtaatt    120
ttaataggta agacgaaaaa taatagagct tgtgaagtta taattccata caaatggtat    180
ttctattttg aaggcgatat aaaggattta gaagaattcg ctaacaacaa aaaaataaaa    240
atcgaatata caaggagca aagaaatat atagaaaaac aaaagatgt ttataaagta       300
tatgttttgc ataaacatta tccaatacta aagaattca ttaaagaaaa gggctataaa      360
aaatacgaaa ccgatataaa tgtttatagg aagttttaa tagataaagg atagagcct       420
tttgatggt ttgaggtaga aggcaaaatt ttattatcta cctctaacaa agttagaata      480
aaagcacaaa gtataaaaag attgtatgaa aagactaagc catcggtttt agcttttgat    540
atagaagttt acgatgaggc tttccctaat cctgaaaaag acaaaataat atctatagcc    600
ctttatggag acaattacga aggggttatc tcttacaaag gagaaccaac tataaaagtt    660
aataccgaat atgaattaat tgagaaattt gtcgaaataa tagaaagctt aaaaccagac    720
ataatagtta catacaatgg ggataatttc gatatagact ttttagtgaa aagggcttct    780
ttatacaata taaggctacc aataaaattg gttaacaaaa agagcctac ttataatttt      840
agggaaagcg cacatgtaga tttgtataaa acaattacta ccatatataa aacccaattg    900
tctacccaaa catattcatt aaatgaagta gctaagaaa ttcttggaga ggagaaaatt       960
tatgattatg aaaacatgtt atatgattgg gccataggca attataacaa agtgttcgaa   1020
tacaatttaa agatgccga ttaacatat aagctattca atactatga aatgattta       1080
ttggaattag caagattggt taaccaacca ttatttgatg tatctaggtt tagctatagt   1140
aatatagttg aatggtatct aatcaaaaaa agcagaaat ataatgaaat tgtgcctaac    1200
aaaccaaaaa tggaagaagt agagagaaga aaattaaata cctatgcagg agcattcgtt   1260
tacgaaccaa aacccggttt gtatgagaat ttagctgtac tggatttcgc ttctctgtat   1320
ccttcaatta tattagagca taatgtttct ccaggcacaa tatattgtga gcatgatgat   1380
tgtaaacaaa atggggtaga agcgataata aataatgaga aaaatatgt gtggttttgc    1440
aaaaaagtaa aagggtttat tccaacggta ttagagcatt tgtatacaaa aggctagaa    1500
```

```
cttaagagaa aactgaaaga actagatagg gatagtgaag aatataaaat tataaatgct   1560
aagcaaagag tattgaaaat aataattaat gcaacctatg gctatatggg tttcccaaga   1620
gcgagatggt attgcataga ctgtgctgcg gcagtagcag cttggggcag gaaatacatt   1680
aattatatat taaaaaggc cgaagaagaa ggattcaaag taatttatgg agattctata    1740
atggatactg aaatagaggt tatagaaaat ggtataaaaa agaaagaaaa gctaagcgat   1800
ttgtttaaca aatactatgc cggttttcaa atagggggaga acattatgc tttccctcca    1860 gatttgtatg tatatgatgg agaaagatgg gttaaagtat attcaataat aaaacatgaa   1920
accgagaccg attttatatga aataaatggg ataacattaa gtgcaaacca tttagtttta   1980
agcaaaggca attgggttaa agccaaggaa tatgaaaata aaaataatca ccatcaccat   2040
caccacatgc gctatcttgg caaaaagaga gttattttat atgatttatc tactgaatcg   2100
ggtaaatttt atgttaatgg gctagtttta cacaataccg attcattatt catttctggg   2160
gacaaagaca aagtattaga attttttagag aaagtaaata aagaattacc cggtaaaata   2220
caattagatt tagaagattt ctatgttaga gggatattcg taaaaaagag gggtgaacaa   2280 aaggggggcaa aaaagaaata tgctttatta agcgaacaag gttacataaa gctaaggggc   2340
ttcgaagcag taagaacaga ctgggctccc atagttaaag aagtccaaac aaagctattg   2400
gaaattttgc taaagaagg taacatagaa aaagcaagac aatacataaa agaaattatt   2460
agaaagctaa gaaatagaga aataccatgg gagaagcttt taattacaga aacgataaga   2520
aagcctttag aaaaatacaa agttgaagct cctcatgtgg cagcagcaaa aaaatataaa   2580
aggttgggct ataagttat gcctggcttt agagttagat atttagtggt aggtagcact   2640
ggaagggttt cagatagaat taaaatagac aaagaagtta ggggtaatga atatgacccc   2700
gaatactaca tagaaaaaca actattgcct gcagtagagc aaatattaga atctgtaggt   2760
attaaagaca cattcacagg caaaaaacta acagatttct ttaaatga                2808
```

<210> SEQ ID NO 36
<211> LENGTH: 935
<212> TYPE: PRT
<213> ORGANISM: Artificial Sequence
<220> FEATURE:
<223> OTHER INFORMATION: Neq HS M3 DNA polymerase

<400> SEQUENCE: 36

```
Met Leu His Gln Leu Pro Thr Met Val Val Glu Lys Ala Val Lys
1               5                   10                  15

Glu Glu Glu Gly Tyr Ser Val Leu Lys Cys Tyr Trp Ile Asn Ile Glu
                20                  25                  30

Asn Thr Pro Leu Asp Glu Val Ile Leu Ile Gly Lys Asp Glu Asn Asn
            35                  40                  45

Arg Ala Cys Glu Val Ile Ile Pro Tyr Lys Trp Tyr Phe Tyr Phe Glu
        50                  55                  60

Gly Asp Ile Lys Asp Leu Glu Glu Phe Ala Asn Asn Lys Lys Ile Lys
65                  70                  75                  80

Ile Glu Tyr Thr Lys Glu Gln Lys Tyr Ile Glu Lys Pro Lys Asp
                85                  90                  95

Val Tyr Lys Val Tyr Val Leu His Lys His Tyr Pro Ile Leu Lys Glu
            100                 105                 110

Phe Ile Lys Glu Lys Gly Tyr Lys Lys Tyr Glu Thr Asp Ile Asn Val
        115                 120                 125

Tyr Arg Lys Phe Leu Ile Asp Lys Gly Ile Glu Pro Phe Glu Trp Phe
```

```
            130                 135                 140
Glu Val Glu Gly Lys Ile Leu Leu Ser Thr Ser Asn Lys Val Arg Ile
145                 150                 155                 160
Lys Ala Gln Ser Ile Lys Arg Leu Tyr Glu Lys Thr Lys Pro Ser Val
                165                 170                 175
Leu Ala Phe Asp Ile Glu Val Tyr Asp Glu Ala Phe Pro Asn Pro Glu
            180                 185                 190
Lys Asp Lys Ile Ile Ser Ile Ala Leu Tyr Gly Asp Asn Tyr Glu Gly
        195                 200                 205
Val Ile Ser Tyr Lys Gly Glu Pro Thr Ile Lys Val Asn Thr Glu Tyr
    210                 215                 220
Glu Leu Ile Glu Lys Phe Val Glu Ile Ile Glu Ser Leu Lys Pro Asp
225                 230                 235                 240
Ile Ile Val Thr Tyr Asn Gly Asp Asn Phe Asp Ile Asp Phe Leu Val
                245                 250                 255
Lys Arg Ala Ser Leu Tyr Asn Ile Arg Leu Pro Ile Lys Leu Val Asn
            260                 265                 270
Lys Lys Glu Pro Thr Tyr Asn Phe Arg Glu Ser Ala His Val Asp Leu
        275                 280                 285
Tyr Lys Thr Ile Thr Thr Ile Tyr Lys Thr Gln Leu Ser Thr Gln Thr
    290                 295                 300
Tyr Ser Leu Asn Glu Val Ala Lys Glu Ile Leu Gly Glu Glu Lys Ile
305                 310                 315                 320
Tyr Asp Tyr Glu Asn Met Leu Tyr Asp Trp Ala Ile Gly Asn Tyr Asn
                325                 330                 335
Lys Val Phe Glu Tyr Asn Leu Lys Asp Ala Glu Leu Thr Tyr Lys Leu
            340                 345                 350
Phe Lys Tyr Tyr Glu Asn Asp Leu Leu Glu Leu Ala Arg Leu Val Asn
        355                 360                 365
Gln Pro Leu Phe Asp Val Ser Arg Phe Ser Tyr Ser Asn Ile Val Glu
    370                 375                 380
Trp Tyr Leu Ile Lys Lys Ser Arg Lys Tyr Asn Glu Ile Val Pro Asn
385                 390                 395                 400
Lys Pro Lys Met Glu Glu Val Glu Arg Arg Lys Leu Asn Thr Tyr Ala
                405                 410                 415
Gly Ala Phe Val Tyr Glu Pro Lys Pro Gly Leu Tyr Glu Asn Leu Ala
            420                 425                 430
Val Leu Asp Phe Ala Ser Leu Tyr Pro Ser Ile Ile Leu Glu His Asn
        435                 440                 445
Val Ser Pro Gly Thr Ile Tyr Cys Glu His Asp Asp Cys Lys Gln Asn
    450                 455                 460
Gly Val Glu Ala Ile Ile Asn Asn Glu Lys Lys Tyr Val Trp Phe Cys
465                 470                 475                 480
Lys Lys Val Lys Gly Phe Ile Pro Thr Val Leu Glu His Leu Tyr Thr
                485                 490                 495
Lys Arg Leu Glu Leu Lys Arg Lys Leu Lys Glu Leu Asp Arg Asp Ser
            500                 505                 510
Glu Glu Tyr Lys Ile Ile Asn Ala Lys Gln Arg Val Leu Lys Ile Ile
        515                 520                 525
Ile Asn Ala Thr Tyr Gly Tyr Met Gly Phe Pro Arg Ala Arg Trp Tyr
    530                 535                 540
Cys Ile Asp Cys Ala Ala Ala Val Ala Ala Trp Gly Arg Lys Tyr Ile
545                 550                 555                 560
```

Asn Tyr Ile Leu Lys Arg Ala Glu Glu Gly Phe Lys Val Ile Tyr
            565                 570                 575

Gly Asp Ser Ile Met Asp Thr Glu Ile Glu Val Ile Glu Asn Gly Ile
        580                 585                 590

Lys Lys Lys Glu Lys Leu Ser Asp Leu Phe Asn Lys Tyr Tyr Ala Gly
    595                 600                 605

Phe Gln Ile Gly Glu Lys His Tyr Ala Phe Pro Pro Asp Leu Tyr Val
610                 615                 620

Tyr Asp Gly Glu Arg Trp Val Lys Val Tyr Ser Ile Ile Lys His Glu
625                 630                 635                 640

Thr Glu Thr Asp Leu Tyr Glu Ile Asn Gly Ile Thr Leu Ser Ala Asn
                645                 650                 655

His Leu Val Leu Ser Lys Gly Asn Trp Val Lys Ala Lys Glu Tyr Glu
            660                 665                 670

Asn Lys Asn Asn His His His His His His Met Arg Tyr Leu Gly Lys
        675                 680                 685

Lys Arg Val Ile Leu Tyr Asp Leu Ser Thr Glu Ser Gly Lys Phe Tyr
690                 695                 700

Val Asn Gly Leu Val Leu His Asn Thr Asp Ser Leu Phe Ile Ser Gly
705                 710                 715                 720

Asp Lys Asp Lys Val Leu Glu Phe Leu Glu Lys Val Asn Lys Glu Leu
                725                 730                 735

Pro Gly Lys Ile Gln Leu Asp Leu Glu Asp Phe Tyr Val Arg Gly Ile
            740                 745                 750

Phe Val Lys Lys Arg Gly Glu Gln Lys Gly Ala Lys Lys Lys Tyr Ala
        755                 760                 765

Leu Leu Ser Glu Gln Gly Tyr Ile Lys Leu Arg Gly Phe Glu Ala Val
770                 775                 780

Arg Thr Asp Trp Ala Pro Ile Val Lys Glu Val Gln Thr Lys Leu Leu
785                 790                 795                 800

Glu Ile Leu Leu Lys Glu Gly Asn Ile Glu Lys Ala Arg Gln Tyr Ile
                805                 810                 815

Lys Glu Ile Ile Arg Lys Leu Arg Asn Arg Glu Ile Pro Trp Glu Lys
            820                 825                 830

Leu Leu Ile Thr Glu Thr Ile Arg Lys Pro Leu Glu Lys Tyr Lys Val
        835                 840                 845

Glu Ala Pro His Val Ala Ala Lys Tyr Lys Arg Leu Gly Tyr
850                 855                 860

Lys Val Met Pro Gly Phe Arg Val Arg Tyr Leu Val Val Gly Ser Thr
865                 870                 875                 880

Gly Arg Val Ser Asp Arg Ile Lys Ile Asp Lys Glu Val Arg Gly Asn
                885                 890                 895

Glu Tyr Asp Pro Glu Tyr Tyr Ile Glu Lys Gln Leu Leu Pro Ala Val
            900                 905                 910

Glu Gln Ile Leu Glu Ser Val Gly Ile Lys Asp Thr Phe Thr Gly Lys
        915                 920                 925

Lys Leu Thr Asp Phe Phe Lys
930                 935

<210> SEQ ID NO 37
<211> LENGTH: 32
<212> TYPE: DNA
<213> ORGANISM: Artificial Sequence
<220> FEATURE:

<223> OTHER INFORMATION: In-Pfu-CR

<400> SEQUENCE: 37
accatcagta ttgtgtaaaa ctagcccatt aa                                      32

<210> SEQ ID NO 38
<211> LENGTH: 35
<212> TYPE: DNA
<213> ORGANISM: Artificial Sequence
<220> FEATURE:
<223> OTHER INFORMATION: In-Pfu-C

<400> SEQUENCE: 38
gttttacaca atactgatgg tctctatgca actat                                   35

<210> SEQ ID NO 39
<211> LENGTH: 35
<212> TYPE: DNA
<213> ORGANISM: Artificial Sequence
<220> FEATURE:
<223> OTHER INFORMATION: Pfu-Xho
<220> FEATURE:
<221> NAME/KEY: misc_feature
<222> LOCATION: (1)..(6)
<223> OTHER INFORMATION: n is a, c, g, or t

<400> SEQUENCE: 39
nnnnnnctcg agctaggatt ttttaatgtt aagcc                                   35

<210> SEQ ID NO 40
<211> LENGTH: 2841
<212> TYPE: DNA
<213> ORGANISM: Artificial Sequence
<220> FEATURE:
<223> OTHER INFORMATION: Nefu HS DNA polymerase

<400> SEQUENCE: 40
atgttacacc aactccccac gatggttgta gaagaaaagg cggtaaaaga ggaagaaggg      60
tatagcgtgc taaaatgtta ttggattaat atagagaaca ccccttttaga cgaggtaatt     120
ttaataggta aagacgaaaa taatagagct tgtgaagtta taattccata caaatggtat     180
ttctattttg aaggcgatat aaaggattta gaagaattcg ctaacaacaa aaaaataaaa     240
atcgaatata caaaggagca aaagaaatat atagaaaaac caaagatgt ttataaagta      300
tatgttttgc ataaacatta tccaatacta aaagaattca ttaaagaaaa gggctataaa     360
aaatacgaaa ccgatataaa tgtttatagg aagttttta tagataaagg atagagcct       420
tttgaatggt ttgaggtaga aggcaaaatt ttattatcta cctctaacaa agttagaata     480
aaagcacaaa gtataaaaag attgtatgaa aagactaagc catcggtttt agcttttgat     540
atagaagttt acagtgaggc tttccctaat cctgaaaaag acaaaataat atctatagcc     600
ctttatggag acaattacga agggttatc tcttacaaag gagaaccaac tataaaagtt      660
aataccgaat atgaattaat tgagaaattt gtcgaaataa tagaaagctt aaaaccagac     720
ataatagtta catacaatgg ggataatttc gatatagact ttttagtgaa aagggcttct     780
ttatacaata taaggctacc aataaaaattg gttaacaaaa aagagcctac ttataatttt     840
agggaaagcg cacatgtaga tttgtataaa acaattacta ccatatataa aacccaattg      900
tctacccaaa catattcatt aaatgaagta gctaaagaaa ttcttggaga ggagaaaatt     960
tatgattatg aaaacatgtt atatgattgg gccataggca attataacaa agtgttcgaa    1020
tacaatttaa aagatgccga attaacatat aagctattca aatactatga aaatgattta    1080

```
ttggaattag caagattggt taaccaacca ttatttgatg tatctaggtt tagctatagt     1140
aatatagttg aatggtatct aatcaaaaaa agcagaaaat ataatgaaat tgtgcctaac     1200
aaaccaaaaa tggaagaagt agagagaaga aaattaaata cctatgcagg agcattcgtt     1260
tacgaaccaa aacccggttt gtatgagaat ttagctgtac tggatttcgc ttctctgtat     1320
ccttcaatta tattagagca taatgttttct ccaggcacaa tatattgtga gcatgatgat     1380
tgtaaacaaa tggggtaga agcgataata aataatgaga aaaatatgt gtggttttgc       1440 aaaaaagtaa aagggtttat tccaacggta ttagagcatt tgtatacaaa aaggctagaa     1500
cttaagagaa aactgaaaga actagatagg gatagtgaag aatataaaat tataaatgct     1560
aagcaagcag tattgaaaat aataattaat gcaacctatg gctatatggg tttcccaaat     1620
gcgagatggt attgcataga ctgtgctgcg gcagtagcag cttggggcag gaaatacatt     1680
aattatatat taaaagggc cgaagaagaa ggattcaaag taatttatgg agattctata     1740
atggatactg aaatagaggt tatagaaaat ggtataaaaa agaaagaaaa gctaagcgat     1800
ttgtttaaca aatactatgc cggttttcaa atagggggaga acattatgc tttccctcca     1860 gatttgtatg tatatgatgg agaaagatgg gttaaagtat attcaataat aaaacatgaa     1920
accgagaccg atttatatga aataaatggg ataacattaa gtgcaaacca tttagtttta     1980
agcaaaggca attgggttaa agccaaggaa tatgaaaata aaaataatca ccatcaccat     2040
caccacatgc gctatcttgg caaaaagaga gttattttat atgatttatc tactgaatcg     2100
ggtaaatttt atgttaatgg gctagtttta cacaatactg atggtctcta tgcaactatc     2160
ccaggaggag aaagtgagga aataaagaaa aaggctctag aatttgtaaa atacataaat     2220
tcaaagctcc ctggactgct agagcttgaa tatgaagggt tttataagag gggattcttc     2280
gttacgaaga agaggtatgc agtaatagat gaagaaggaa aagtcattac tcgtggttta     2340
gagatagtta ggagagattg gagtgaaatt gcaaaagaaa ctcaagctag agttttggag     2400
acaatactaa aacacggaga tgttgaagaa gctgtgagaa tagtaaaaga agtaatacaa     2460
aagcttgcca attatgaaat tccaccagag aagctcgcaa tatatgagca gataacaaga     2520
ccattacatg agtataaggc gataggtcct cacgtagctg ttgcaaagaa actagctgct     2580
aaaggagtta aaataaagcc aggaatggta attggataca tagtacttag aggcgatggt     2640
ccaattagca ataggggcaat tctagctgag gaatacgatc ccaaaaagca caagtatgac     2700
gcagaatatt acattgagaa ccaggttctt ccagcggtac ttaggatatt ggagggattt     2760
ggatacagaa aggaagacct cagataccaa aagacaagac aagtcggcct aacttcctgg     2820
cttaacatta aaaaatccta g                                               2841
```

<210> SEQ ID NO 41
<211> LENGTH: 946
<212> TYPE: PRT
<213> ORGANISM: Artificial Sequence
<220> FEATURE:
<223> OTHER INFORMATION: Nefu HS DNA polymerase

<400> SEQUENCE: 41

```
Met Leu His Gln Leu Pro Thr Met Val Val Glu Glu Lys Ala Val Lys
1               5                   10                  15

Glu Glu Glu Gly Tyr Ser Val Leu Lys Cys Tyr Trp Ile Asn Ile Glu
            20                  25                  30

Asn Thr Pro Leu Asp Glu Val Ile Leu Ile Gly Lys Asp Glu Asn Asn
        35                  40                  45
```

```
Arg Ala Cys Glu Val Ile Ile Pro Tyr Lys Trp Tyr Phe Tyr Phe Glu
     50                  55                  60

Gly Asp Ile Lys Asp Leu Glu Glu Phe Ala Asn Asn Lys Lys Ile Lys
 65                  70                  75                  80

Ile Glu Tyr Thr Lys Glu Gln Lys Lys Tyr Ile Glu Lys Pro Lys Asp
                 85                  90                  95

Val Tyr Lys Val Tyr Val Leu His Lys His Tyr Pro Ile Leu Lys Glu
            100                 105                 110

Phe Ile Lys Glu Lys Gly Tyr Lys Lys Tyr Glu Thr Asp Ile Asn Val
        115                 120                 125

Tyr Arg Lys Phe Leu Ile Asp Lys Gly Ile Glu Pro Phe Glu Trp Phe
    130                 135                 140

Glu Val Glu Gly Lys Ile Leu Leu Ser Thr Ser Asn Lys Val Arg Ile
145                 150                 155                 160

Lys Ala Gln Ser Ile Lys Arg Leu Tyr Glu Lys Thr Lys Pro Ser Val
                165                 170                 175

Leu Ala Phe Asp Ile Glu Val Tyr Ser Glu Ala Phe Pro Asn Pro Glu
            180                 185                 190

Lys Asp Lys Ile Ile Ser Ile Ala Leu Tyr Gly Asp Asn Tyr Glu Gly
        195                 200                 205

Val Ile Ser Tyr Lys Gly Glu Pro Thr Ile Lys Val Asn Thr Glu Tyr
    210                 215                 220

Glu Leu Ile Glu Lys Phe Val Glu Ile Ile Glu Ser Leu Lys Pro Asp
225                 230                 235                 240

Ile Ile Val Thr Tyr Asn Gly Asp Asn Phe Asp Ile Asp Phe Leu Val
                245                 250                 255

Lys Arg Ala Ser Leu Tyr Asn Ile Arg Leu Pro Ile Lys Leu Val Asn
            260                 265                 270

Lys Lys Glu Pro Thr Tyr Asn Phe Arg Glu Ser Ala His Val Asp Leu
        275                 280                 285

Tyr Lys Thr Ile Thr Thr Ile Tyr Lys Thr Gln Leu Ser Thr Gln Thr
    290                 295                 300

Tyr Ser Leu Asn Glu Val Ala Lys Glu Ile Leu Gly Glu Glu Lys Ile
305                 310                 315                 320

Tyr Asp Tyr Glu Asn Met Leu Tyr Asp Trp Ala Ile Gly Asn Tyr Asn
                325                 330                 335

Lys Val Phe Glu Tyr Asn Leu Lys Asp Ala Glu Leu Thr Tyr Lys Leu
            340                 345                 350

Phe Lys Tyr Tyr Glu Asn Asp Leu Leu Glu Leu Ala Arg Leu Val Asn
        355                 360                 365

Gln Pro Leu Phe Asp Val Ser Arg Phe Ser Tyr Ser Asn Ile Val Glu
    370                 375                 380

Trp Tyr Leu Ile Lys Lys Ser Arg Lys Tyr Asn Glu Ile Val Pro Asn
385                 390                 395                 400

Lys Pro Lys Met Glu Glu Val Glu Arg Arg Lys Leu Asn Thr Tyr Ala
                405                 410                 415

Gly Ala Phe Val Tyr Glu Pro Lys Pro Gly Leu Tyr Glu Asn Leu Ala
            420                 425                 430

Val Leu Asp Phe Ala Ser Leu Tyr Pro Ser Ile Ile Leu Glu His Asn
        435                 440                 445

Val Ser Pro Gly Thr Ile Tyr Cys Glu His Asp Asp Cys Lys Gln Asn
    450                 455                 460
```

Gly Val Glu Ala Ile Ile Asn Asn Glu Lys Lys Tyr Val Trp Phe Cys
465                 470                 475                 480

Lys Lys Val Lys Gly Phe Ile Pro Thr Val Leu Glu His Leu Tyr Thr
            485                 490                 495

Lys Arg Leu Glu Leu Lys Arg Lys Leu Lys Glu Leu Asp Arg Asp Ser
        500                 505                 510

Glu Glu Tyr Lys Ile Ile Asn Ala Lys Gln Ala Val Leu Lys Ile Ile
        515                 520                 525

Ile Asn Ala Thr Tyr Gly Tyr Met Gly Phe Pro Asn Ala Arg Trp Tyr
530                 535                 540

Cys Ile Asp Cys Ala Ala Ala Val Ala Ala Trp Gly Arg Lys Tyr Ile
545                 550                 555                 560

Asn Tyr Ile Leu Lys Arg Ala Glu Glu Gly Phe Lys Val Ile Tyr
                565                 570                 575

Gly Asp Ser Ile Met Asp Thr Glu Ile Glu Val Ile Glu Asn Gly Ile
                580                 585                 590

Lys Lys Lys Glu Lys Leu Ser Asp Leu Phe Asn Lys Tyr Tyr Ala Gly
        595                 600                 605

Phe Gln Ile Gly Glu Lys His Tyr Ala Phe Pro Pro Asp Leu Tyr Val
    610                 615                 620

Tyr Asp Gly Glu Arg Trp Val Lys Val Tyr Ser Ile Ile Lys His Glu
625                 630                 635                 640

Thr Glu Thr Asp Leu Tyr Glu Ile Asn Gly Ile Thr Leu Ser Ala Asn
                645                 650                 655

His Leu Val Leu Ser Lys Gly Asn Trp Val Lys Ala Lys Glu Tyr Glu
            660                 665                 670

Asn Lys Asn Asn His His His His His Met Arg Tyr Leu Gly Lys
            675                 680                 685

Lys Arg Val Ile Leu Tyr Asp Leu Ser Thr Glu Ser Gly Lys Phe Tyr
    690                 695                 700

Val Asn Gly Leu Val Leu His Asn Thr Asp Gly Leu Tyr Ala Thr Ile
705                 710                 715                 720

Pro Gly Gly Glu Ser Glu Glu Ile Lys Lys Lys Ala Leu Glu Phe Val
                725                 730                 735

Lys Tyr Ile Asn Ser Lys Leu Pro Gly Leu Leu Glu Leu Glu Tyr Glu
            740                 745                 750

Gly Phe Tyr Lys Arg Gly Phe Phe Val Thr Lys Lys Arg Tyr Ala Val
        755                 760                 765

Ile Asp Glu Glu Gly Lys Val Ile Thr Arg Gly Leu Glu Ile Val Arg
770                 775                 780

Arg Asp Trp Ser Glu Ile Ala Lys Glu Thr Gln Ala Arg Val Leu Glu
785                 790                 795                 800

Thr Ile Leu Lys His Gly Asp Val Glu Glu Ala Val Arg Ile Val Lys
            805                 810                 815

Glu Val Ile Gln Lys Leu Ala Asn Tyr Glu Ile Pro Pro Glu Lys Leu
                820                 825                 830

Ala Ile Tyr Glu Gln Ile Thr Arg Pro Leu His Glu Tyr Lys Ala Ile
            835                 840                 845

Gly Pro His Val Ala Val Ala Lys Lys Leu Ala Lys Gly Val Lys
        850                 855                 860

Ile Lys Pro Gly Met Val Ile Gly Tyr Ile Val Leu Arg Gly Asp Gly
865                 870                 875                 880

Pro Ile Ser Asn Arg Ala Ile Leu Ala Glu Glu Tyr Asp Pro Lys Lys

```
                      885                 890                 895
His Lys Tyr Asp Ala Glu Tyr Tyr Ile Glu Asn Gln Val Leu Pro Ala
                900                 905                 910

Val Leu Arg Ile Leu Glu Gly Phe Gly Tyr Arg Lys Glu Asp Leu Arg
        915                 920                 925

Tyr Gln Lys Thr Arg Gln Val Gly Leu Thr Ser Trp Leu Asn Ile Lys
    930                 935                 940

Lys Ser
945
```

<210> SEQ ID NO 42
<211> LENGTH: 30
<212> TYPE: DNA
<213> ORGANISM: Artificial Sequence
<220> FEATURE:
<223> OTHER INFORMATION: MP_beta_globin_F

<400> SEQUENCE: 42
tccctctcaa ccctacagtc acccatttgg                                    30

<210> SEQ ID NO 43
<211> LENGTH: 30
<212> TYPE: DNA
<213> ORGANISM: Artificial Sequence
<220> FEATURE:
<223> OTHER INFORMATION: MP_beta_globin_R

<400> SEQUENCE: 43
cagtcatgga caataaccct cctcccaggt                                    30

<210> SEQ ID NO 44
<211> LENGTH: 22
<212> TYPE: DNA
<213> ORGANISM: Artificial Sequence
<220> FEATURE:
<223> OTHER INFORMATION: Hgb194_F

<400> SEQUENCE: 44
acatttgctt ctgacacaac tg                                            22

<210> SEQ ID NO 45
<211> LENGTH: 21
<212> TYPE: DNA
<213> ORGANISM: Artificial Sequence
<220> FEATURE:
<223> OTHER INFORMATION: Hgb194_R

<400> SEQUENCE: 45
tccacatgcc cagtttctat t                                             21

<210> SEQ ID NO 46
<211> LENGTH: 24
<212> TYPE: DNA
<213> ORGANISM: Artificial Sequence
<220> FEATURE:
<223> OTHER INFORMATION: HGPRT_F2

<400> SEQUENCE: 46
tgtggcagaa gcagtgagta actg                                          24

<210> SEQ ID NO 47
<211> LENGTH: 30
<212> TYPE: DNA
<213> ORGANISM: Artificial Sequence

```
<220> FEATURE:
<223> OTHER INFORMATION: beta_globin_F

<400> SEQUENCE: 47
tctaatctcc ctctcaaccc tacagtcacc                                  30

<210> SEQ ID NO 48
<211> LENGTH: 27
<212> TYPE: DNA
<213> ORGANISM: Artificial Sequence
<220> FEATURE:
<223> OTHER INFORMATION: beta_globin_R

<400> SEQUENCE: 48
tggaaatgat caggcttgga ttcaaag                                     27

<210> SEQ ID NO 49
<211> LENGTH: 27
<212> TYPE: DNA
<213> ORGANISM: Artificial Sequence
<220> FEATURE:
<223> OTHER INFORMATION: Epo_F

<400> SEQUENCE: 49
ttggggatgg caaaaacctg acctgtg                                     27

<210> SEQ ID NO 50
<211> LENGTH: 28
<212> TYPE: DNA
<213> ORGANISM: Artificial Sequence
<220> FEATURE:
<223> OTHER INFORMATION: Epo_R

<400> SEQUENCE: 50
gcatccactt ctccggccaa acttcaat                                    28

<210> SEQ ID NO 51
<211> LENGTH: 30
<212> TYPE: DNA
<213> ORGANISM: Artificial Sequence
<220> FEATURE:
<223> OTHER INFORMATION: Hgb400_F

<400> SEQUENCE: 51
tcaaacagac accatggtgc atctgactcc                                  30

<210> SEQ ID NO 52
<211> LENGTH: 28
<212> TYPE: DNA
<213> ORGANISM: Artificial Sequence
<220> FEATURE:
<223> OTHER INFORMATION: Hgb400_R

<400> SEQUENCE: 52
aaggtgccct tgagcttgtc caggtgag                                    28

<210> SEQ ID NO 53
<211> LENGTH: 26
<212> TYPE: DNA
<213> ORGANISM: Artificial Sequence
<220> FEATURE:
<223> OTHER INFORMATION: beta_actin_F

<400> SEQUENCE: 53
tcttgtcctt tccttcccag ggcgtg                                      26
```

```
<210> SEQ ID NO 54
<211> LENGTH: 27
<212> TYPE: DNA
<213> ORGANISM: Artificial Sequence
<220> FEATURE:
<223> OTHER INFORMATION: beta_actin_R

<400> SEQUENCE: 54
ctggggtctt gggatgggga gtctgtt                                              27

<210> SEQ ID NO 55
<211> LENGTH: 13
<212> TYPE: PRT
<213> ORGANISM: Artificial Sequence
<220> FEATURE:
<223> OTHER INFORMATION: Neq N-extein junction region

<400> SEQUENCE: 55

Lys Val Ile Tyr Gly Asp Ser Ile Met Asp Thr Glu Ile
1               5                   10

<210> SEQ ID NO 56
<211> LENGTH: 14
<212> TYPE: PRT
<213> ORGANISM: Artificial Sequence
<220> FEATURE:
<223> OTHER INFORMATION: Neq C-extein junction region

<400> SEQUENCE: 56

Val Asn Gly Leu Val Leu His Asn Thr Asp Ser Leu Phe Ile
1               5                   10

<210> SEQ ID NO 57
<211> LENGTH: 6
<212> TYPE: PRT
<213> ORGANISM: Artificial Sequence
<220> FEATURE:
<223> OTHER INFORMATION: Pfu N-extein junction region

<400> SEQUENCE: 57

Lys Val Leu Tyr Ile Asp
1               5

<210> SEQ ID NO 58
<211> LENGTH: 6
<212> TYPE: PRT
<213> ORGANISM: Artificial Sequence
<220> FEATURE:
<223> OTHER INFORMATION: Pfu C-extein junction region

<400> SEQUENCE: 58

Thr Asp Ser Leu Phe Ile
1               5
```